US011208442B2

(12) United States Patent
Ito et al.

(10) Patent No.: US 11,208,442 B2
(45) Date of Patent: Dec. 28, 2021

(54) ENDO-BETA-N-ACETYLGLUCOSAMINIDASE

(71) Applicant: Daiichi Sankyo Company, Limited, Tokyo (JP)

(72) Inventors: Hanako Ito, Edogawa-ku (JP); Yasunori Ono, Ichikawa (JP); Kensuke Nakamura, Bunkyo-ku (JP)

(73) Assignee: Daiichi Sankyo Company, Limited, Tokyo (JP)

(*) Notice: Subject to any disclaimer, the term of this patent is extended or adjusted under 35 U.S.C. 154(b) by 0 days.

(21) Appl. No.: 16/465,930

(22) PCT Filed: Dec. 1, 2017

(86) PCT No.: PCT/JP2017/043219
§ 371 (c)(1),
(2) Date: May 31, 2019

(87) PCT Pub. No.: WO2018/101454
PCT Pub. Date: Jun. 7, 2018

(65) Prior Publication Data

US 2019/0309028 A1 Oct. 10, 2019

(30) Foreign Application Priority Data

Dec. 2, 2016 (JP) ............................ JP2016-234808

(51) Int. Cl.

| | |
|---|---|
| ***C12N 9/24*** | (2006.01) |
| ***C12N 15/09*** | (2006.01) |
| ***C12P 21/02*** | (2006.01) |
| ***C07K 14/37*** | (2006.01) |
| ***C12N 1/20*** | (2006.01) |
| *C12R 1/19* | (2006.01) |

(52) U.S. Cl.
CPC .............. *C07K 14/37* (2013.01); *C12N 1/205* (2021.05); *C12N 9/2402* (2013.01); *C12N 15/09* (2013.01); *C12P 21/02* (2013.01); *C12R 2001/19* (2021.05)

(58) Field of Classification Search
CPC .............................. C12N 9/3434; C12N 15/00
See application file for complete search history.

(56) References Cited

U.S. PATENT DOCUMENTS

| | | | |
|---|---|---|---|
| 6,815,191 | B1 | 11/2004 | Kobayashi et al. |
| 2018/0208915 | A1 | 7/2018 | Kawaguchi et al. |

FOREIGN PATENT DOCUMENTS

| | | | |
|---|---|---|---|
| GB | 2 431 156 | A | 4/2007 |
| JP | 11-332568 | A | 12/1999 |
| WO | 2004/035740 | A2 | 4/2004 |
| WO | 2005/000404 | A2 | 1/2005 |
| WO | 2008/116129 | A2 | 9/2008 |
| WO | 2009/034386 | A1 | 3/2009 |
| WO | 2009/045174 | A1 | 4/2009 |
| WO | 2009/045175 | A1 | 4/2009 |
| WO | 2009/053716 | A1 | 4/2009 |
| WO | 2009/100406 | A2 | 8/2009 |
| WO | 2009/146406 | A1 | 12/2009 |
| WO | 2010/005558 | A2 | 1/2010 |
| WO | 2010/044401 | A1 | 4/2010 |
| WO | 2010/114494 | A1 | 10/2010 |
| WO | 2010/136491 | A1 | 12/2010 |
| WO | 2010/138589 | A1 | 12/2010 |
| WO | 2011/058027 | A2 | 5/2011 |
| WO | 2012/007493 | A1 | 1/2012 |
| WO | 2012/037226 | A1 | 3/2012 |
| WO | 2012082997 | A1 | 6/2012 |
| WO | 2012/104776 | A1 | 8/2012 |
| WO | 2012/107465 | A1 | 8/2012 |
| WO | 2016/136984 | A1 | 1/2016 |
| WO | 2017/010559 | A1 | 4/2018 |

OTHER PUBLICATIONS

Eshima, Y., et al., "Transglycosylation Activity of Glycosynthase Mutants of Endo-β-N-Acetylglucosaminidase From Coprinopsis cinerea," PLOS One 10(7):e0132859, Jul. 2015, 15 pages.

Fujita, K., et al., "Molecular Cloning of Mucor hiemalis Endo-β-N-acetylglucosaminidase and Some Properties of the Recombinant Enzyme," Archives of Biochemistry and Biophysics 432(1):41-49, Dec. 2004.

Goodfellow, J.J., et al., "An Endoglycosidase With Alternative Glycan Specificity Allows Broadened Glycoprotein Remodelling," Journal of the American Chemical Society 134(19):8030-8033, May 2012.

International Preliminary Report on Patentability dated Jun. 4, 2019, issued in corresponding International Application No. PCT/JP2017/043219, filed Dec. 1, 2017, 8 pages.

International Search Report and Written Opinion dated Mar. 6, 2018, issued in corresponding International Application No. PCT/JP2017/043219, filed Dec. 1, 2017, 13 pages.

Le Parc, A., et al., "A Novel Endo-β-N-Acetylglucosaminidase Releases Specific N-Glycans Depending on Different Reaction Conditions," Biotechnology Progress 31(5):1323-1330, Sep./Oct. 2015.

Tarentino, A.L., et al., "Multiple Endoglycosidase F Activities Expressed by Flavobacterium meningosepticum Endoglycosidases $F_2$ and $F_3$," Journal of Biological Chemistry 268(13):9702-9708, May 1993.

Extended European Search Report dated Apr. 30, 2020, issued in corresponding Application No. EP 17 87 6284.5, filed Dec. 1, 2017, 10 pages.

Kobayashi, K., et al., "KR 1020007012943-A/3: Endo-beta-N-acetylglucosaminidase gene," retrieved from EBI, Accession No. KPOP:DI522624, Feb. 21, 2008, Database KPOP [Online], 1 page.

(Continued)

*Primary Examiner* — Maryam Monshipouri
(74) *Attorney, Agent, or Firm* — Christensen O'Connor Johnson Kindness PLLC

(57) ABSTRACT

The present invention provides a novel endo-β-N-acetylglucosaminidase that is isolated from a fungus belonging to the genus *Rhizomucor* and is active under high-temperature conditions; various mutant enzymes thereof; genes encoding the enzymes; a recombinant plasmid; a transformant transformed with the plasmid; and the like.

12 Claims, 5 Drawing Sheets

Specification includes a Sequence Listing.

(56) References Cited

OTHER PUBLICATIONS

Yamamoto, K., and T. Katoh, "Mucor hiemalis mutant endo-b-N-acetylglucosaminidase (endo-M) Q128A," retrieved from EBI, Accession No. GS_PROT:BDE42800, Oct. 20, 2016, Database Geneseq [Online],1 page.

Figure 4

```
Endo-Rp             1 MPSLELQQAADTRLFESMPLQTMNELGSWEPSNASRANIATIPLHQRSNLDPAEPRLIVTHDMAGGYKEDSNIQGNTYDT 80
Endo-Rp2            1 MPSLELQQAADTRLFESMPLQTMNELGSWEPSNASRANIATIPLHQRSNLDPAEPRLIVTHDMAGGYKEDSNIQGNTYDT 80
Endo-Rp3            1 MPSLELQQAADTRLFESMPLQTMNELGSWEPSNASRANIATIPLHQRSNLDPAEPRLIVTHDMAGGYKEDSNIQGNTYDT 80
Endo-Rp4            1 MPSLELQQAADTRLFESMPLQTMNELGSWEPSNASRANIATIPLHQRSNLDPAEPRLIVTHDMAGGYKEDSNIQGNTYDT 80
Endo-Rp5            1 MPSLELQQAADTRLFESMPLQTMNELGSWEPSNASRANIATIPLHQRSNLDPAEPRLIVTHDMAGGYKEDSNIQGNTYDT 80
Endo-Rm             1 MPSLELQQAVDTRLFESTPLMTMDELGSWDPSNALRASIATVPLHPRPSIDPTEPRLIVTHDMAGGYKEDFSIQGNAYDT 80
PUTATIVE SEQUENCE   1 MPSLELQQAADTRLFESMPLQTMNELGSWEPSNASRANIATIPLHQRSNLDPAEPRLIVTHDMAGGYKEDSNIQGNTYDT 80

Endo-Rp            81 IYSCQYWQYVDTFIYFSHHRVTIPPVNWINACHRNGVKTLGTFIVEGAAGMFALERFVYGPEPGQRNSWSPYYADKLVDI 160
Endo-Rp2           81 IYSCQYWQYVDTFIYFSHHRVTIPPVNWINACHRNGVKTLGTFIVEGTAGMFALERFVYGPEPGQRNSWSPYYADKLVDI 160
Endo-Rp3           81 IYSCQYWQYVDTFIYFSHHRVTIPPVNWINACHRNGVKTLGTFIVEGAAGMFALERFVYGPEPGQRNSWSPYYADKLVDI 160
Endo-Rp4           81 IYSCQYWQYVDTFIYFSHHRVTIPPVNWINACHRNGVKTLGTFIVEGAAGMFALERFVYGPEPGQRNSWSPYYADKLVDI 160
Endo-Rp5           81 IYSCQYWQYVDTFIYFSHHRVTIPPVNWINACHRNGVKTLGTFIVEGAAGMFALERFVYGPEPGQRNSWSPYYADKLVDI 160
Endo-Rm            81 VYTCQYWQYVDIFIYFSHHRVTIPPVNWTNACHRNGVKSLGTFIVEGAAGMFALERFVYGPNPGQRKSWSPYYADKLVDI 160
PUTATIVE SEQUENCE  81 IYSCQYWQYVDTFIYFSHHRVTIPPVNWINACHRNGVKTLGTFIVEGAAGMFALERFVYGPEPGQRNSWSPYYADKLVDI 160

Endo-Rp           161 AEFYGFDGWLLNIESDFFPLYRNPSLKAIHLA-----KLLRYLKNAMHARVPGSEIIWYDSMTTNGSVQWQNNITPKNSI 235
Endo-Rp2          161 AEFYGFDGWLLNIESDFFPLYRNPSLKAIHLA-----KLLRYLKNAMHARVPGSEIIWYDSMTTNGSVQWQNNITPKNSI 235
Endo-Rp3          161 AEFYGFDGWLLNIESDFFPLYRNPSLKAIHLA-----KLLRYLKNAMHARVPGSEIIWYDSMTTNGSVQWQNNITPKNSI 235
Endo-Rp4          161 AEFYGFDGWLLNIESDFFPLYRNPSLKAIHLA-----KLLRYLKNAMHARVPGSEIIWYDSMTTNGSVQWQNNITPKNSI 235
Endo-Rp5          161 AEFYGFDGWLLNIESDFFPLYRNPSLKAIHLA-----KLLRYLKNAMHARVPGSEIIWYDSMTTNGSVQWQNNITPKNSI 235
Endo-Rm           161 AEFYGFDGWLINIESDFFPLYRSPSMKAKHLA-----KLLLYLRNAMHARVPGSQIIWYDSMTTSGYVQWQNNITPQNEI 235
PUTATIVE SEQUENCE 161 AEFYGFDGWLLNIESDFFPLYRNPSLKAIHLANTYYIRLLRYLKNAMHARVPGSEIIWYDSMTTNGSVQWQNNITPKNSI 240

Endo-Rp           236 FFEAADGIFLNYWWNATVPPLALQVAHRLGRQGSDVYFGTDVWGRGTFGGGGFDSYLAVGTARAFKTSSALFGTAWIYEH 315
Endo-Rp2          236 FFEAADGIFLNYWWNATVPPLALQVAHRLGRQGSDVYFGTDVWGRGTFGGGGFDSYLAVGTARAFKTSSALFGTAWIYEH 315
Endo-Rp3          236 FFEAADGIFLNYWWNATVPPLALQVAHRLGRQGSDVYFGTDVWGRGTFGGGGFDSYLAVGTARAFKTSSALFGTAWIYEH 315
Endo-Rp4          236 FFEAADGIFLNYWWNATVPPLALQVAHRLGRQGSDVYFGTDVWGRGTFGGGGFDSYLAVGTARAFKTSSALFGTAWIYEH 315
Endo-Rp5          236 FFEAADGIFLNYWWNATVPPLALQVAHRLGRQGSDVYFGTDVWGRGTFGGGGFDSYLAVGTARAFKTSSALFGTAWIYEH 315
Endo-Rm           236 FFEAADGIFLNYWWNATYPPFAMQVAHYLGRQGSDVYFGSDIWGRGTFGGGGFDSYLAVATASAFKTSSALFGTAWTYEH 315
PUTATIVE SEQUENCE 241 FFEAADGIFLNYWWNATVPPLALQVAHRLGRQGSDVYFGTDVWGRGTFGGGGFDSYLAVGTARAFKTSSALFGTAWIYEH 320

Endo-Rp           316 FGKKDFELMDRLLWLGGDQSEYPAQEGEQNRTVKVTSHLGRHPGIADVSPVRSAPGKTWFATWFDRGYGTGFYYQGKKLL 395
Endo-Rp2          316 FGKKDFELMDRLLWLGGDQSEYPAQEGEQNRTVKVTSHLGRHPGIADVSPVRSAPGKTWFATWFDRGYGTGFYYQGKKLL 395
Endo-Rp3          316 FGKKDFELMDRLLWLGGGQSEYPAQEGEQNRTVKVTSHLGRHPGIADVSPVRSAPGKTWFATWFDRGYGTGFYYQGKKLL 395
Endo-Rp4          316 FGKKDFELMDRLLWLGGDQSEYPAQEGEQNRTVKVTSHLGRHPGIADVSPVRSAPGKTWFATWFDRGYGTGFYYQGKKLL 395
Endo-Rp5          316 FGKKDFELMDRLLWLGGDQSEYPAQEGEQNRTVKVTSHLGRHPGIADVSPVRSAPGKTWFATWFDRGYGTGFYYQGKKLL 395
Endo-Rm           316 FEKKDFELMDRLLWLGGDQSEYPAQAEGQESIAKSGSRLGRHPGITDVAAVRSAPGRRWFVTWFDRGHGTGFYHQGKKLL 395
PUTATIVE SEQUENCE 321 FGKKDFELMDRLLWLGGDQSEYPAQEGEQNRTVKVTSHLGRHPGIADVSPVRSAPGKTWFATWFDRGYGTGFYYQGKKLL 400

Endo-Rp           396 SQPWSHLSHQSIPPNLIARLQREENHGLSYFLADDDAYIGGTSLLIAAEITQERQLPLYQLEYDVTEGCEVQFIYKSPEP 475
Endo-Rp2          396 SQPWSHLSHQSIPPNLIARLQREENHGLSYFLADDDAYIGGTSLLIAAEITQERQLPLYQLEYDVTEGCEVQFIYKSPEP 475
Endo-Rp3          396 SQPWSHLSHQSIPPNLIARLQREENHGLSYFLADDDAYLGGTSLLIAAEITQERQLPLYQLEYDVTEGCEVQFIYKSPEP 475
Endo-Rp4          396 SQPWSHLSHQSIPPNLIARLQREENHGLSYFLADDDAYIGGTSLLIAAEITQERQLPLYQLEYDATEGCEVQFIYKSPEP 475
Endo-Rp5          396 SQPWSHLSHQSIPPNLIARLQREENHGLSYFLADDDAYIGGTSLLIAAEITQERQLPLYQLEYDVTEGCEVQFIYKSPEP 475
Endo-Rm           396 SQPWSHLSHQSIPPNLVARLQRKEDDGVSYFLADDDAYIGGTSLLIAAEGTQERQIPLYQLNYDATNGCEVQFVYKSPEP 475
PUTATIVE SEQUENCE 401 SQPWSHLSHQSIPPNLIARLQREENHGLSYFLADDDAYIGGTSLLIAAEITQERQLPLYQLEYDVTEGCEVQFIYKSPEP 480

Endo-Rp           476 DMQGKIDIYLNLQVTDILPDELAFYWQDVTDASSQADATTAMRLYLNENTVIYLKPSRKQELAEGWLLCSVRVPPTYPLG 555
Endo-Rp2          476 DMQGKIDIYLNLQVTDILPDELAFYWQDVTDASSQADATTAMRLYLNENTVIYLKPSRKQELAEGWLLCSVRVPPTYPLG 555
Endo-Rp3          476 DMQGKIDIYLNLQVTDILPDELAFYWQDVTDASSQADATTAMRLYLNENTVVYLKPSRKQELAEGWLLCSVRVPPTYPLG 555
Endo-Rp4          476 DMQGKIDIYLNLQVTDILPDELAFYWQDVTDASSQADATTAMRLYLNENTVIYLKPSRKQELAEGWLLCSVRVPPTYPLG 555
Endo-Rp5          476 DMQGKIDIYLNLQVTDILPDELAFYWQDVTDASSQADATTAMRLYLNENTVIYLKPSRKQELAEGWLLCSVRVPPTYPLG 555
Endo-Rm           476 DMQSKVQIYLNLRVTDVLPDELAYYWHDVAATSPQPQATTASRLNINEDTSVYLNTSKTQELAEGWVLCSVRVPSVHPLG 555
PUTATIVE SEQUENCE 481 DMQGKIDIYLNLQVTDILPDELAFYWQDVTDASSQADATTAMRLYLNENTVIYLKPSRKQELAEGWLLCSVRVPPTYPLG 560

Endo-Rp           556 IATIKELGIHVDGKETVLFRLGLLTIIPLGDAPSAL-SRITQVQLQRDEDIHSKCPSSSCELWATLSWMMEHNSKEDWDQ 634
Endo-Rp2          556 IATIKELGIHVDGTETVLFRLGLLTIIPLGDAPSAL-SRITQVQLQRDEDIHSKCPSSSCELWATLSWMMEHNSKEDWDQ 634
Endo-Rp3          556 IATIKELGIHVDGTETVLFRLGLLTIIPLGDAPSAL-SRITQVQLQRDEDIHSKCSSSSCELWATLSWMMERNSKEDWDQ 634
Endo-Rp4          556 IATIKELGIHVDGTETVLFRLGLLTIIPLGDAPSAL-SRITQVQLQRDEDIHSKCPSSSCELWATLSWMMEHNSKEDWDQ 634
Endo-Rp5          556 IATIKELGIHVDGTETVLFRLGLLTIIPLGDAPSAL-SRITQVQLQRDEDIHSKCPSSSCELWATLSWMMEHNSKEDWDQ 634
Endo-Rm           556 EAAIEELGIYLDGTEDVLFRLGLLTIVPYTDTSSTLASKITHIQLQRDADVSSKCLSSSCELWATLSWMMESNSSEEWNQ 635
PUTATIVE SEQUENCE 561 IATIKELGIHVDGTETVLFRLGLLTIIPLGDAPSAL-SRITQVQLQRDEDIHSKCPSSSCELWATLSWMMEHNSKEDWDQ 639

Endo-Rp           635 VDHYMIFFKNVDSKAEPIFLGTSFSTEYRISGLEIKKHGNSIEIWAVNRLGTVIARQDIDIQ 696
Endo-Rp2          635 VDHYMIFFKNVDSKAEPIFLGTSFSTEYRISGLEIKKHGNSIEIWAVNRLGTVIARQDIDIQ 696
Endo-Rp3          635 VDHYMIFFKNVDSKAEPIFLGTSFSTEYRISGLEIKKHGNSIEIWAVNRLGTVIARQDIDIQ 696
Endo-Rp4          635 VDHYMIFFKNVDSKAEPIFLGTSFSTEYRISGLEIKKHGNSIEIWAVNRLGTVIARQDIDIQ 696
Endo-Rp5          635 VDHYMIFFKNVDSKAEPIFLGTSFSTEYRISGLEIKKHGNSIEIWAVNRLGTVIARQDIDIQ 696
Endo-Rm           636 VDHYLISYGDINADGAATFLGTTFTTEYRISGLEMKNDIDYIQISAVSRLGNILAQQTIGIQ 697
PUTATIVE SEQUENCE 640 VDHYMIFFKNVDSKAEPIFLGTSFSTEYRISGLEIKKHGNSIEIWAVNRLGTVIARQDIDIQ 701
```

ENDO-BETA-N-ACETYLGLUCOSAMINIDASE

TECHNICAL FIELD

The present invention relates to an endo-β-N-acetylglucosaminidase that is active under high-temperature conditions, a gene encoding the enzyme, a recombinant plasmid, a transformant transformed with the plasmid, and the like.

BACKGROUND ART

Glycoproteins are widely found in tissues of animals and plants, cell membranes and the walls of eukaryotic microorganisms, and the like. Recently, it has been revealed that sugar chains in glycoproteins have important roles in mechanisms such as cell differentiation, carcinogenesis, and intercellular recognition. To elucidate these mechanisms, studies on the correlation between the structure and function of sugar chains have been pursued. In drug discovery studies, attempts such as remodeling of sugar chains, in which sugar chains in glycoproteins including antibodies are substituted with a uniform structure of sugar chain, and glycosylation of peptides or small molecules has been pursued. Such drug discovery studies often use sugar chains cleaved from naturally-occurring glycoproteins/glycopeptides with a uniform sugar chain using an enzyme such as endo-β-N-acetylglucosaminidase.

Representative sugar chains in animal glycoproteins include N-linked sugar chains attached to asparagine side chains. N-linked sugar chains are classified into high-mannose, hybrid, and complex types depending on their structure but have a chitobiose structure having two GlcNAc residues linked to the reducing end as a common structure. Endo-β-N-acetylglucosaminidase is an enzyme having both an activity that hydrolyzes the glycosidic linkage in chitobiose structures and transglycosylation activity that transfers the cleaved sugar chain onto an acceptor having a specific structure. Endo-β-N-acetylglucosaminidases, which have been isolated from various biological species, have respective different substrate specificities. Different endo-β-N-acetylglucosaminidases have been used for different purposes. Among these, endo-β-N-acetylglucosaminidases that use complex-type sugar chains as substrates have been reported to include those as described below.

Endo-M, which is an enzyme derived from *Mucor hiemalis*, has a substrate specificity that is an activity of 4.4% on a complex-type biantennary sugar chain (agalacto biantennary PAsugar) when the activity on high-mannose-type Man8GlcNAc2 was set to 100% (Non Patent Literature 1: Fujita et al., (2004) Arch Biochem Biophy. 432: p 41-49). It is reported in the same literature that Endo-M was expressed as an insoluble aggregate in all of the inductions of expression at 37° C. in *Escherichia coli* and the induction temperature being changed to 20° C. resulted in low enzymatic activity in a soluble fraction and thus the expression of Endo-M was attempted in yeast. Thus, it is believed that it is difficult to express Endo-M suitably in *E. coli*. Endo-M is also known to inactivate at 40° C. or more.

It has been reported that Endo-Om, which is an enzyme derived from the yeast *Ogataea minuta* (Patent Literature 1: WO2013/051608 or US2014-0313246), uses complex-type sugar chains as substrates and has an optimum temperature of 50° C. in a hydrolytic reaction. The expression of Endo-Om in organisms except yeast is unknown.

Endo-F2 and Endo-F3 are enzymes derived from *Elizabethkingia miricola* (Non Patent Literature 2: Tarentino A L et al., (1993) J Biol Chem. 268: p 9702-9708). Endo-F2 hydrolyzes high-mannose-type and biantennary complex-type sugar chains and has no hydrolytic activity on hybrid-type sugar chains. On the other hand, Endo-F3 hydrolyzes biantennary or triantennary complex-type sugar chains and has no hydrolytic activity on high-mannose-type and hybrid-type sugar chains.

Endo-S, which is an enzyme derived from *Streptococcus pyogenes*, hydrolyzes only biantennary complex-type sugar chains and has no hydrolytic activity on high-mannose-type and hybrid-type sugar chains (Non Patent Literature 3: Goodfellow J J et al., (2012) J Am Chem Sci. 134: p 8030-8033).

Endo-CE, which is an enzyme derived from *Caenorhabditis elegans*, hydrolyzes high-mannose-type and biantennary complex-type sugar chains and it is unknown whether Endo-CE can cleave hybrid-type sugar chains (Non Patent Literature 4: Kato T et al., (2002) Glycobiology 12: p 581-587). Endo-CE is reported to have an optimum temperature of 20° C. in a hydrolytic reaction.

In contrast to Endo-M and Endo-Om known so far, Endo-CC is an enzyme that reportedly can be expressed in *E. coli*. Non Patent Literature 5 (Y. Eshima et al., (2015) PLoS One. 21; 10(7): e0132859) describes that Endo-CC was expressed in *E. coli* in an amount of 0.1 mg/250 mL of culture (=0.4 mg/L of culture). Endo-CC is reported to have an optimum temperature of 35° C. in a hydrolytic reaction.

In the light of improvement of reaction efficiency and prevention of contamination, enzymes that are active at a high temperature of around 50° C. are desired when cleaved sugar chains are used as raw materials of pharmaceuticals. It is also said that when a plurality of recombinant materials are used as raw materials of pharmaceuticals, the same host species should be used to reduce safety concerns in pharmaceuticals. It is desirable to have an ability to produce in an amount greater than a usual amount in *E. coli* because *E. coli* is often selected as a host for producing such raw materials. However, an enzyme that is active at a high temperature and has the ability to be produced in a high yield in *E. coli* remains undiscovered among known endo-β-N-acetylglucosaminidases that use complex-type sugar chains as substrates.

*Rhizomucor pusillus* (*R. pusillus*), which is a species of thermophilic fungi, has an optimal growth temperature of 35-45° C. and is known to be a fungus that produces rennet for cheese production. The genomic sequence of *R. pusillus* including sequence information from *R. pusillus* strain CBS 183.67 is published in the database provided by The Genozymes Project (Concordia University). This database includes a gene having 41.56% homology to Endo-M and the amino acid sequence (SEQ ID NO: 7) encoded by the gene but does not include annotation about the activity of the amino acid sequence. There is no report so far of actually obtaining endo-β-N-acetylglucosaminidase derived from *R. pusillus*. The amino acid sequence from positions 191-198 of the amino acid sequence of SEQ ID NO: 7 (hereinafter referred to as the "known putative sequence") assumed to be endo-β-N-acetylglucosaminidase in the database is Leu-Ala-Asn-Thr-Tyr-Tyr-Ile-Arg (LANTYYIR).

CITATION LIST

Patent Literature

Patent Literature 1: WO2013/051608 or US2014-0313246

Non Patent Literature

Non Patent Literature 1: Fujita et al., (2004) Arch Biochem Biophy. 432: p 41-49

Non Patent Literature 2: Tarentino A L et al., (1993) J Biol Chem. 268: p 9702-9708

Non Patent Literature 3: Goodfellow J J et al., (2012) J Am Chem Sci. 134: p 8030-8033

Non Patent Literature 4: Kato T et al., (2002) Glycobiology 12: p 581-587

Non Patent Literature 5: Y. Eshima et al., (2015) PLoS One. 21; 10(7): e0132859

SUMMARY OF INVENTION

Technical Problem

The present invention aims to provide a novel endo-β-N-acetylglucosaminidase that can be produced by *E. coli* and has hydrolytic activity on complex-type sugar chains under high-temperature conditions.

Solution to Problem

The present inventors have conducted intensive studies directed towards achieving the aforementioned object. As a result, the inventors have found that culture supernatants from a plurality of strains belonging to *Rhizomucor pusillus* have good hydrolytic activity on complex sugar chains under high-temperature conditions and that endo-β-N-acetylglucosaminidase cloned from the strains exhibits good expression efficiency in an *E. coli* production system and the produced enzyme has the aforementioned hydrolytic activity. The present inventors further pursued the study, thereby completing the present invention.

The present invention provides the following aspects of the invention.

(1) A polypeptide having the following properties (A) and (B):

(A) the polypeptide comprises an amino acid sequence having 75% or more identity and 95% or more similarity to the amino acid sequence shown in SEQ ID NO: 1 and is an amino acid sequence different from the amino acid sequence of SEQ ID NO: 7; and (B) the polypeptide exhibits, at any temperature from 45 to 60° C., 40% or more of the maximal activity value of hydrolytic activity and/or transglycosylation activity on complex sugar chains.

(2) The polypeptide according to (1), having the following properties (A) and (B):

(A) the polypeptide comprises an amino acid sequence having 75% or more identity and 95% or more similarity to the amino acid sequence shown in SEQ ID NO: 1 and an amino acid sequence of Leu-Ala-Lys-Leu-Leu (LAKLL) at positions corresponding to the amino acid sequence from amino acid positions 191 to 195 of SEQ ID NO: 1;

(B) the polypeptide exhibits, at any temperature from 45 to 60° C., 40% or more of the maximal activity value of hydrolytic activity on complex sugar chains.

(3) The polypeptide according to (1), wherein the hydrolytic activity on complex sugar chains at 50° C. is 60% or more of the maximal activity value.

(4) The polypeptide according to any of (1) to (3), wherein, in addition to having the properties (A) and (B), (C) the polypeptide is produced in an amount of 10 mg/L of culture or more in recombinant expression in *E. coli.*

(5) The polypeptide according to any of (1) to (4), wherein the polypeptide has 85% or more sequence identity to the region from amino acid positions 54 to 341 of the amino acid sequence of SEQ ID NO: 1.

(6) The polypeptide according to any of (1) to (5), wherein at least one of amino acids D276, V223, W225, Y247, and W248 remains unchanged and preferably at least D276 remains unchanged.

(7) The polypeptide according to any of (1) to (3), wherein the polypeptide is a polypeptide consisting of the amino acid sequence of SEQ ID NO: 1 or a polypeptide consisting of an amino acid sequence having at least one mutation selected from the group consisting of A128T, D333G, I434L, V460A, I527V, K569T, P610S, and H626R in the amino acid sequence of SEQ ID NO: 1.

(8) The polypeptide according to (1), wherein the polypeptide consists of an amino acid sequence of any of SEQ ID NOS: 1 to 6.

(9) The polypeptide according to any of (1) to (6), wherein the polypeptide has an amino acid sequence satisfying the property (A) and has at least one of the mutations contained in SEQ ID NO: 23.

(10) The polypeptide according to (9), wherein the polypeptide has a mutation in at least one amino acid selected from N172, D176, Y214, 5216, L245, N246, T275, L306, F307, and A310 and has increased transglycosylation activity.

(11) The polypeptide according to (7), wherein the polypeptide has at least one mutation selected from the group of: a mutation in which N172 is substituted with Gln, Asp, Gly, Ala, Phe, Cys, His, Ile, Ser, Thr, Val, or Met; a mutation in which D176 is substituted with Arg; a mutation in which Y214 is substituted with Phe; a mutation in which 5216 is substituted with Val; a mutation in which L245 is substituted with Ser; a mutation in which N246 is substituted with Asp; a mutation in which T275 is substituted with Ile; a mutation in which F283 is substituted with Ser; a mutation in which L306 is substituted with Ile; a mutation in which F307 is substituted with Tyr; a mutation in which A310 is substituted with Asp; and a mutation in which E314 is substituted with Gln.

(12) The polypeptide according to any of (9) to (11), wherein the polypeptide has a mutation in which W278 is substituted with Phe or Tyr. The polypeptide according to (11), wherein, more specifically, the polypeptide has mutation N172Q, N172D, W278F, N172Q/W278F, N172D/W278F, or Y214/L3061/L307Y in the amino acid sequence of any of SEQ ID NOS: 1 to 6.

(13) A polynucleotide encoding the polypeptide according to any of (1) to (12).

(14) The polynucleotide according to (13), having a nucleotide sequence of any of the nucleotide sequences from nucleotide positions 1 to 2088 of SEQ ID NOS: 8 to 17 and the nucleotide sequences from nucleotide positions 1 to 2091 of SEQ ID NOS: 18 to 19.

(15) An expression plasmid comprising the polynucleotide according to (13) or (14).

(16) A host cell transformed with the plasmid according to (15).

(17) The host cell according to (16), wherein the host cell is *E. coli* transformed with a plasmid comprising a polynucleotide comprising the nucleotide sequence from nucleotide positions 1 to 2088 of SEQ ID NO: 9, 11, 13, 15, or 17 or the nucleotide sequence from nucleotide positions 1 to 2091 of SEQ ID NO: 19.

(18) A method of producing the polypeptide according to any of (1) to (12), comprising culturing the host cells according to (16) or (17) and collecting the polypeptide according to any of (1) to (12) from the resulting culture.

(19) A reagent comprising the polypeptide according to any of (1) to (12).

Advantageous Effects of Invention

The novel endo-β-N-acetylglucosaminidases of the present invention have good hydrolytic activity on complex-type sugar chains under high-temperature reaction conditions of 50° C. or more so that they can safely and efficiently provide sugar chains under high-temperature conditions, which can prevent bacterial growth, in the manufacture of pharmaceuticals using these enzymes and can lead to high reaction efficiency. The enzymes of the present invention can be produced in a heterologous expression system using *E. coli* in high yield. In cases where biological raw materials (such as a bioactive peptide/protein and other enzymes) other than the present enzymes are produced by *E. coli* in the manufacture of pharmaceuticals, use of the same host species in production of the present enzymes can facilitate assessment of the effect of the host species, from which the biological raw materials originate, on the safety of the final product.

BRIEF DESCRIPTION OF DRAWINGS

FIG. 4 shows the alignment of amino acid sequences of Endo-Rp and various homologs thereof, Endo-Rm and the known putative sequence.

DESCRIPTION OF EMBODIMENTS

Figure 1:
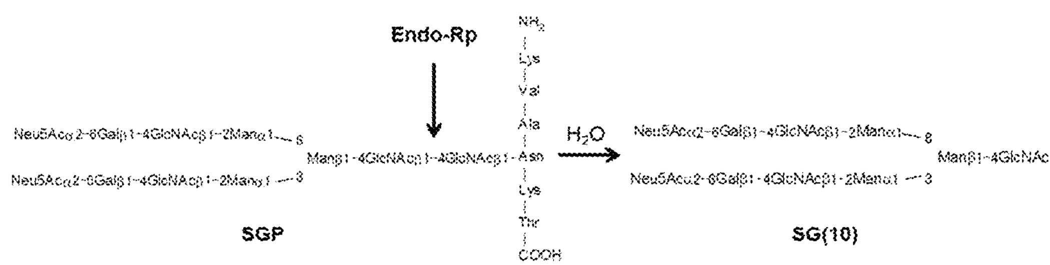
FIG. 1 is a schematic representation showing a hydrolytic reaction in which Endo-Rp uses SGP as a substrate.

The present invention will now be described in detail.

The present invention provides an endo-β-N-acetylglucosaminidase which is a polypeptide having properties (A) and (B):

(A) the polypeptide comprises an amino acid sequence having 75% or more identity and 95% or more similarity to the amino acid sequence shown in SEQ ID NO: 1 (Endo-Rp amino acid sequence) and is an amino acid sequence different from the amino acid sequence of SEQ ID NO: 7; and (B) the polypeptide exhibits 40% or more of the maximal activity value of hydrolytic activity and/or transglycosylation activity on complex-type sugar chains at a temperature ranging from 45 to 60° C.

In the present invention, "complex-type sugar chain" means a sugar chain that is among human N-linked sugar chains and has a basic structure consisting of formulae (I) or (II) as described below. The complex-type sugar chain has a structure in which each of two branched chains (1-3 chain and 1-6 chain), branched from mannose (β mannose) near the reducing end, has GlcNAc. The structure will vary depending on the presence or absence of galactose and sialic acid at the non-reducing end as well as its valence isomerism and position isomerism. As long as the complex-type sugar chain has this basic structure, it may also have another branched structure or a structure that has been chemically modified at some of the hydroxy groups of a carbohydrate or a carbonyl group of sialic acid at the non-reducing end. It is reported that, as an example of such a chemically modified complex-type sugar chain, SGP modified by oximation after oxidative cleavage of diol in the sialic acid of SGP can be used as an Endo-M substrate (Org. Biomol. Chem, 2016, 14, 9501-9518).

[Formula (I)]

(I)

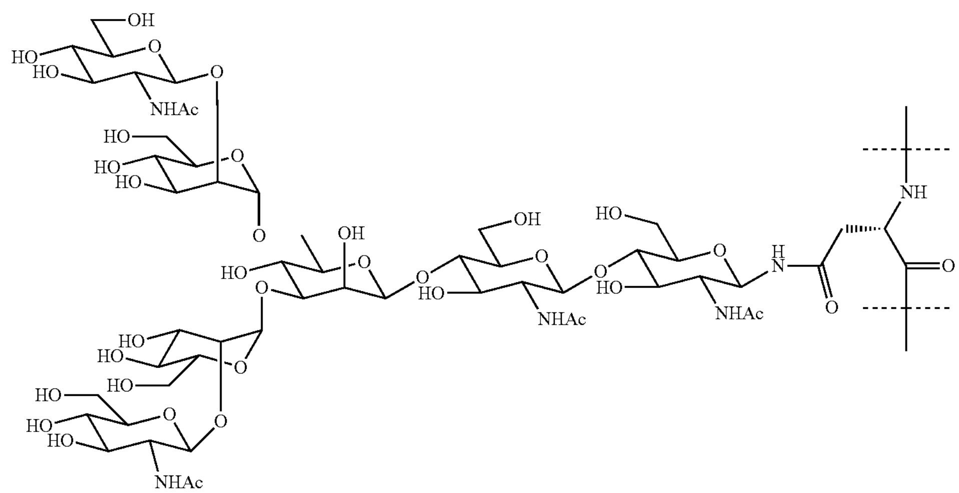

[Formula (II)]

(II)

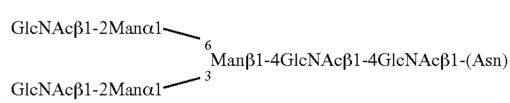

Complex-type sugar chains can typically include a sialylglycan (SG) included in sialylglycopeptide (SGP: formula (III) and (IV) below) extracted from chicken egg yolk. SGP can be purified from avian egg yolk but purified SGP is commercially available and can be purchased, for example, from Tokyo Chemical Industry Co., Ltd. or the like.

[Formula (III)]

(III)

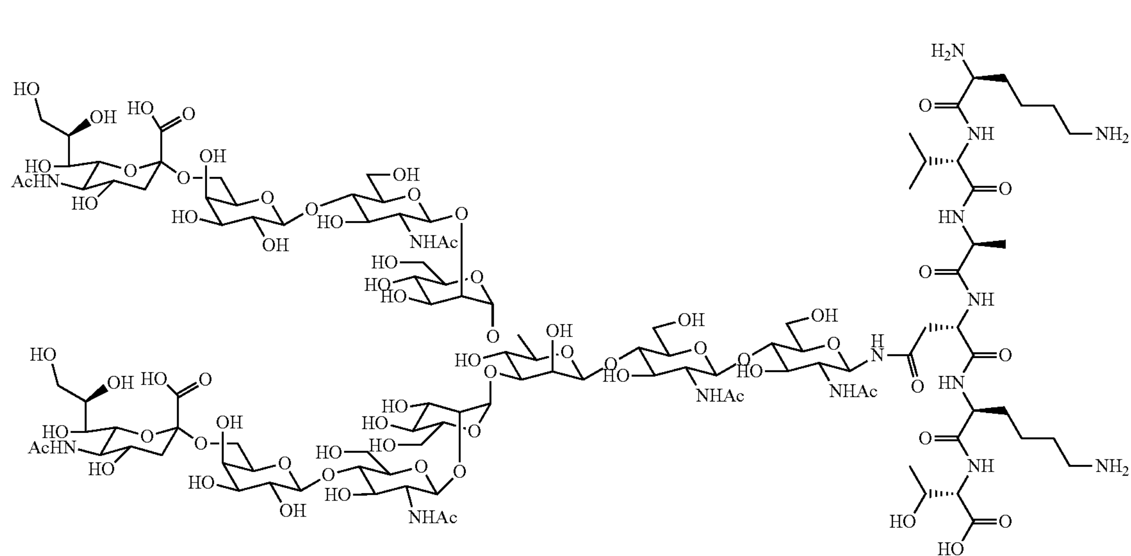

-continued

[Formula (IV)]

(IV)

```
                                                              NH2
                                                               |
                                                              Lys
                                                               |
                                                              Val
                                                               |
                                                              Ala
Neu5Acα2-6Galβ1-4GlcNAcβ1-2Manα1—                              |
                                  6                            |
                                    Manβ1-4GlcNAcβ1-4GlcNAcβ1-Asn
                                  3                            |
Neu5Acα2-6Galβ1-4GlcNAcβ1-2Manα1—                             Lys
                                                               |
                                                              Thr
                                                               |
                                                              COOH
```

In the present invention, "endo-β-N-acetylglucosaminidase" is an enzyme that recognizes a sugar chain as its substrate and has both hydrolytic activity and transglycosylation activity. The amino acid sequence of naturally-occurring endo-β-N-acetylglucosaminidase, which has both of these activities, can be modified to generate a mutant adjusted to enhance or reduce either one of the activities and an enzyme that has only hydrolytic activity or transglycosylation activity by allowing either one of the activities to disappear. The present invention includes not only the naturally-occurring enzymes but also such mutant enzymes.

The hydrolytic activity of the enzymes of the present invention is an activity that specifically hydrolyzes a β1,4 glycosidic linkage in core chitobiose consisting of two consecutive GlcNAc units at the reducing end of the complex-type sugar chain described above (as used herein, "hydrolytic activity" means this activity unless stated otherwise). For example, as shown in FIG. 1, in a hydrolytic reaction in which endo-β-N-acetylglucosaminidase uses SGP as a substrate, SG(10) (structures of formula (V) and (VI) below) consisting of a structure without one GlcNAc at the reducing end of SG is produced.

[Formula (V)]

(V)

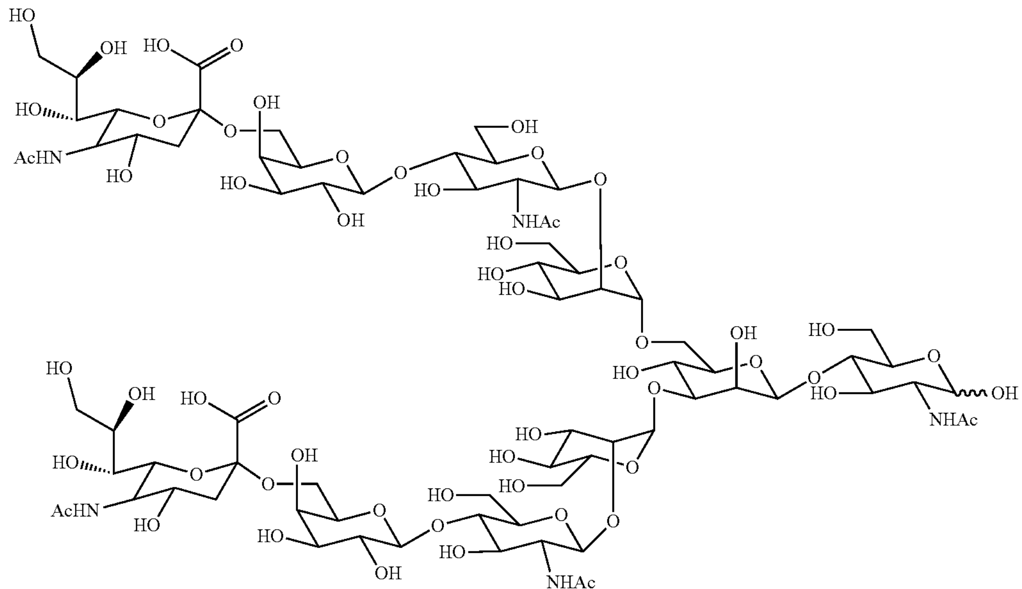

[Formula 6]

(VI)

```
Neu5Acα2-6Galβ1-4GlcNAcβ1-2Manα1—
                                  6
                                    Manβ1-4GlcNAc
                                  3
Neu5Acα2-6Galβ1-4GlcNAcβ1-2Manα1—
```

The transglycosylation activity of the present enzymes is an activity (hereinafter referred to as "transglycosylation activity") that forms β1,4 glycosidic linkage by binding the reducing end of the sugar chain derived from a sugar chain donor, wherein the reducing end has GlcNAc, to a molecule having only GlcNAc as a carbohydrate unit or a molecule comprising a sugar chain having GlcNAc at the non-reducing end (hereinafter referred to as "acceptor molecule"). For example, in a transglycosylation reaction that uses (GlcNAc-)Asn having the structure represented by formula (VII) below as an acceptor molecule and SGP as a donor molecule, SG(10) derived from SGP is transferred to GlcNAc unit of the acceptor molecule to produce (SG-)Asn represented by formula (VIII) below. Similarly, in a transglycosylation reaction that uses GlcNAc-AcA having the structure represented by formula (IX) below as an acceptor molecule and SGP as a donor molecule, SG-A represented by formula (X) below is produced.

[Formula (VII)]

(VII)

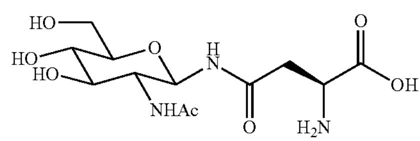

[Formula (VIII)]

(VIII)

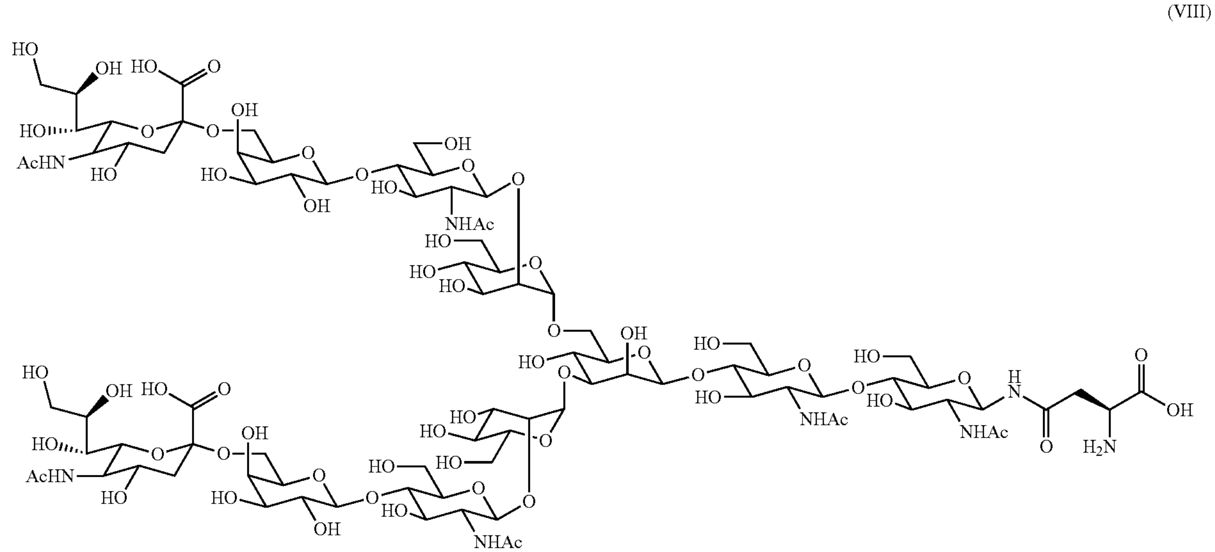

[Formula (IX)]

(IX)

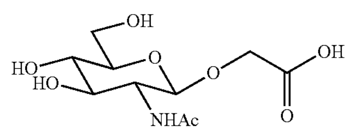

-continued

[Formula (X)]

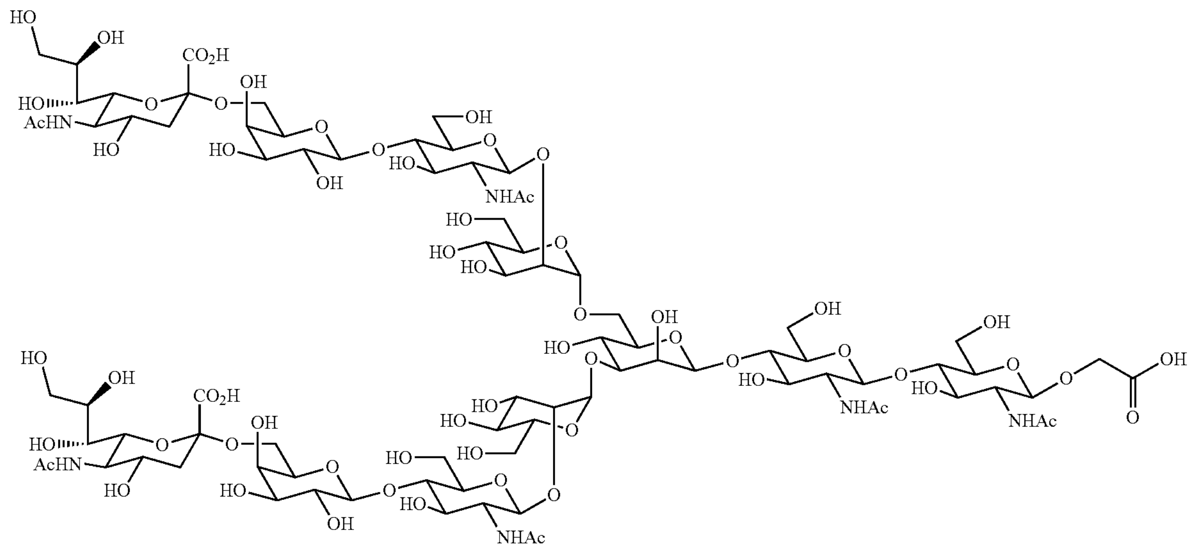

Enzymes and Amino Acid Sequences

The enzymes of the present invention are not limited to enzymes that were obtained in the Examples and have specific sequences as long as they have properties as described above. The enzymes of the present invention may be isolated from naturally occurring sources or artificially produced or modified based on the sequence information of the enzymes of the present invention. For isolation from naturally occurring sources, biological species that are used as isolation sources preferably include, but are not particularly limited to, fungi, more preferably thermophilic fungi, still more preferably fungi belonging to the genus *Rhizomucor*, yet still more preferably fungi belonging to *Rhizomucor pusillus* or *Rhizomucor miehei*.

In the present invention, endo-β-N-acetylglucosaminidases having the present properties are cloned from a plurality of strains belonging to *Rhizomucor pusillus* (*R. pusillus*) which are thermophilic fungi. The enzyme derived from *R. pusillus* strain NBRC 9742 is named as Endo-Rp (amino acid sequence: SEQ ID NO: 1, nucleic acid sequence derived from the strain: SEQ ID NO: 8); the enzyme derived from strain NBRC 9740 is named as Endo-Rp2 (amino acid sequence: SEQ ID NO: 2, nucleic acid sequence derived from the strain: SEQ ID NO: 10); the enzyme derived from strain NBRC 9741 is named as Endo-Rp3 (amino acid sequence: SEQ ID NO: 3, nucleic acid sequence derived from the strain: SEQ ID NO: 12); and the enzyme derived from strain NBRC 9743 is named as Endo-Rp4 (amino acid sequence: SEQ ID NO: 4, nucleic acid sequence derived from the strain: SEQ ID NO: 14). All of the strains of *R. pusillus* described above are available from NBRC. The place of origin of each of the strains is Japan.

The amino acid sequence of SEQ ID NO: 7 (its putative nucleic acid sequence being: SEQ ID NO: 20) is published as the putative amino acid sequence of endo-β-N-acetylglucosaminidase based on the sequence information of the *R. pusillus* strain with its published genome. Optimization of the nucleic acid sequence for an *E. coli* expression system to express it in *E. coli* resulted in little expression and very low enzymatic activity of the enzyme (Example 3). In the amino acid sequence of SEQ ID NO: 7, the amino acid corresponding to Lys at position 193 of SEQ ID NO: 1 is substituted with amino acids Asn-Thr-Tyr-Tyr-Ile-Arg (see FIG. 4). An enzyme consisting of the amino acid sequence (SEQ ID NO: 5) in which the Asn-Thr-Tyr-Tyr-Ile-Arg from positions 193 to 198 in SEQ ID NO: 7 has been substituted with Lys as in SEQ ID NO: 1 showed adequate expression and hydrolytic activity in *E. coli* and the enzyme having this amino acid sequence is named as Endo-Rp5. In conclusion, the sequence corresponding to positions 191 to 195 of SEQ ID NO: 1 is identified as a region very important for the properties of the enzymes of the present invention.

Based on the sequence information of Endo-Rp identified in the present invention, a related sequence was also identified from the published genomic information (*R. miehei* strain CAU432) of *Rhizomucor miehei* (*R. miehei*), a related species of *R. pusillus*. Optimization of the nucleic acid sequence for *E. coli* expression to express the protein in question in *E. coli* resulted in production of the enzyme having the enzymatic activity of the present invention to some degree. This enzyme was named as Endo-Rm (amino acid sequence: SEQ ID NO: 6, nucleic acid sequence derived from the fungus: SEQ ID NO: 18).

Amino acid sequence identity between Endo-Rp and its homologs, Endo-Rp2, Endo-Rp3, Endo-Rp4, and Endo-Rp5 is 99% or more. Endo-Rp2 is a homolog having the mutations A128T and K569T in SEQ ID NO: 1. Endo-Rp3 is a homolog having the mutations D333G, I434L, I527V, K569T, P610S, and H626R in SEQ ID NO: 1. Endo-Rp4 is a homolog having the mutations V460A and K569T in SEQ ID NO: 1. Endo-Rp5 is a homolog having the mutation K569T in SEQ ID NO: 1. The amino acid sequence of Endo-Rm has 96% similarity and 77% identity to the amino acid sequence of SEQ ID NO: 1. The region from positions 54 to 340 in this sequence has a high level of identity (identity: 89%, similarity: 97%)) and the region from positions 190 to 195, His-Leu-Ala-Lys-Leu-Leu (HLAKLL) is completely identical, which satisfies property (A) of the enzymes of the present invention.

When the enzyme of the present invention is an enzyme derived from fungi, the protein may be isolated from culture supernatants of fungi or fungi homogenates or expressed using a heterologous expression system such as *E. coli* or yeast. It is known that many known endo-β-N-acetylglucosaminidases are produced in a low yield using a heterologous expression system in *E. coli*, whereas the amino acid sequence of the enzyme of the present invention has the property of showing excellent production efficiency in an *E. coli* expression system. Nucleic acid sequences of fungi-derived proteins are generally optimized for *E. coli* expression if the proteins are to be expressed in *E. coli*. Even when such optimization was performed, for example, Endo-M N175Q (single amino acid mutant) was produced in *E. coli* in a yield of only 3.7 mg/L of culture. It is also reported that Endo-CC was produced in a yield of 0.4 mg/L of culture. In contrast to this, the enzyme of the present invention is expressed in *E. coli* in an amount of 10 mg/L of culture or more (preferably 12 mg/L of culture or more, and more preferably 15 mg/L of culture or more) and shows a good production efficiency in *E. coli* as compared with conventional enzymes. As shown in Example 4, from the results of production efficiencies of the known putative sequence (SEQ ID NO: 7) and Endo-Rp5 (SEQ ID NO: 5) in *E. coli*, this property seems to be a property imparted by a certain amino acid sequence (particularly, a region comprising amino acid positions 191 to 195 of SEQ ID NO: 1, among others, the sequence from positions 192 to 194, and more particularly, Lys at position 193).

The amino acid sequences of the enzymes of the present invention are each an amino acid sequence that comprises an amino acid sequence that has 75% or more identity and 95% or more similarity to the full-length amino acid sequence of SEQ ID NO: 1 and is different from SEQ ID NO: 7 (preferably the amino acid corresponding to amino acid position 193 of SEQ ID NO: 1 is Lys; preferably the amino acid sequence corresponding to the amino acid sequence from amino acid positions 192 to 194 is Ala-Lys-Leu (AKL); more preferably the amino acid sequence corresponding to the amino acid sequence from amino acid positions 191 to 195 is Leu-Ala-Lys-Leu-Leu (LAKLL)).

The identity of the amino acid sequence refers to a numeric value quantified from the match rate of amino acids, wherein if an amino acid exactly matches with the amino acid present at the corresponding position in the full-length sequence, these amino acids are considered to be the same amino acid. On the other hand, the similarity of amino acid sequence refers to a numeric value quantified from the relationship between two amino acid sequences, wherein if an amino acid has a property similar to that of the amino acid present at the corresponding position, these amino acids are considered to have similarity. Sequence identity and similarity in the present invention are calculated by the sequence analysis software GENETYX-SV/RC (manufactured by GENETYX CORPORATION). This algorithm is commonly used in the art.

The active domain of Endo-Rp is expected to be a region from amino acid positions 1 to 374 of SEQ ID NO: 1 based on the alignment with Endo-A that has been analyzed for its crystal structure (Zhenlian Ling et al, Journal of Molecular Biology (2009), Vol. 389, No. 1, Pages 1-9). In fact, the amino acid sequences of the enzymes of the present invention (Endo-Rp1 to 5 and Endo-Rm) have a sequence identity of 75% or more to SEQ ID NO: 1 for the full-length alignment. The sequence from amino acid positions 54 to 341 of SEQ ID NO: 1 in the region expected to be the active domain has a very high identity of 89%. The full-length amino acid sequence has an identity of preferably 80% or more, more preferably 90% or more, still more preferably 95% or more, and most preferably 99% or more. The region from amino acid positions 54 to 341 of SEQ ID NO: 1 has an identity of preferably 85% or more, more preferably 90% or more, further preferably 95% or more, even more preferably 98% or more, and most preferably is completely identical to the amino acid sequence in this region.

In the specification, the notation of amino acids included in a molecule follows the practice in the art. A mutation site is represented by using one-letter notation of the wild-type amino acid (or nucleic acid) and the position of the mutation (for example, Asn at position 172 is referred to as "N172"). A mutation is also represented by using one-letter notation of the wild-type amino acid (or nucleic acid), the position of the mutation, and one-letter notation of the amino acid (or nucleic acid) after mutation (for example, the mutation in which Asn at position 172 is substituted with Gln is referred to as "N172Q"). A mutant having a particular mutation is represented by using the molecule name and mutation (for example, the mutant having Asn at position 172 of Endo-Rp substituted with Gln is referred to as "Endo-Rp N172Q"). A mutant having a plurality of mutations is represented by the expression delimited by "/" between the plurality of mutations (for example, the Endo-Rp N172Q mutant having an additional mutation in which Trp at position 278 is substituted with Phe is referred to as "Endo-Rp N172Q/W278F").

The enzymes of the present invention may include an amino acid mutation (substitution), deletion, insertion, and/or addition as long as they have a certain level or more of identity or similarity to SEQ ID NO: 1, provided that, at least in SEQ ID NO: 1, the sequence corresponding to positions 193 to 198 of SEQ ID NO: 7 is a sequence different from Asn-Thr-Tyr-Tyr-Ile-Arg and preferably the site corresponding to the amino acid at position 193 (preferably positions 192 to 194, more preferably positions 191 to 195) of SEQ ID NO: 1 has an amino acid sequence completely identical to SEQ ID NO: 1. The results of Example 8 showed that both hydrolytic activity and transglycosylation activity almost disappeared when the D276 amino acid in SEQ ID NO: 1 was mutated and that each of the mutants E126A, V223R, W225H, Y247F, and W248N greatly reduced both of the activities. This indicates that these amino acids in the enzyme of the present invention are preferably amino acids similar or identical to those in SEQ ID NO: 1. Thus, the region in the enzyme of the present invention having the amino acid sequence completely identical to SEQ ID NO: 1 is preferably the region from amino acid positions 118 to 332, more preferably the region from positions 54 to 341, and further preferably the region from positions 1 to 374.

The enzymes of the present invention may include substitution, deletion, insertion, and/or addition of some (preferably 10 or fewer, more preferably 7 or fewer, and still more preferably 5, 4, 3, 2, or 1) amino acids per site in some sites (preferably 5 sites or fewer, more preferably 3, 2, or 1 site) in any region in the amino acid sequences of SEQ ID NOS: 1 to 6, except completely identical regions described above, as long as they have the sequence identity/similarity described above. Such amino acid deletion may provide polypeptides having the properties of the enzymes of the present invention even when, for example, several amino acids are deleted from the N- and/or C-terminus of any of the amino acid sequences of SEQ ID NOS: 1 to 6. Particularly, the region ranging from position 375 to the C-terminus of SEQ ID NO: 1 is not an active domain and therefore accepts many amino acid modifications (substitution, deletion, insertion, and/or addition). Polypeptides with an amino acid addition include those that have amino acids or peptides that are known not to affect the aforementioned activities added to the N- and/or C-terminus of any of the amino acid sequences of SEQ ID NOS: 1 to 6. Such peptides to be added include a tag peptide (such as a His tag and a GST tag) to be added for protein purification.

For the position of an amino acid mutation in the enzymes of the present invention, it has been confirmed that an enzyme having a mutation in at least one position represented by Xaa in SEQ ID NO: 23 retains hydrolytic activity and/or transglycosylation activity. The present enzymes are expected to have the active domain at amino acid positions 1 to 374 in SEQ ID NO: 1. Mutants that keep original activities or are engineered to have the desired activities can be designed by making mutations in the active domain based on the findings of structure-activity relationships in known endo-enzymes and the disclosure of the present invention.

The results from various homologs indicate that the enzymes of the present invention accept amino acid substitutions at A128, D333, 1434, V460, 1527, K569, F610, and H626 in SEQ ID NO: 1. Also, as shown in Example 8, many mutants with substitution of amino acids in the active domain were generated. Many of these mutants were confirmed to reduce apparent activities as compared with wild-type Endo-Rp but to have a certain level of hydrolytic activity and/or transglycosylation activity sufficient to be available for transglycosylation (the specific activity value of any one of the activities is at least 0.5% or more of that of wild-type Endo-Rp). It was also confirmed that certain amino acid substitutions are acceptable in this region. Specifically, the amino acid mutations described below are acceptable.

Although N172 seems to be an active residue which contacts with the substrate, substitution with any amino acid except Trp, Arg, and Tyr allows the activities to be maintained and therefore substitution with any amino acid except amino acids with bulky side chains is widely acceptable. It has been confirmed that substitution with an amino acid having a highly polar side chain such as Gln and Asp; and Gly, Ala, Phe, Cys, His, Ile, Ser, Thr, Val, Met, or the like can increase the transglycosylation activity ratio (transglycosylation activity value/hydrolytic activity value).

The substitution of D176 with Arg allowed the activities to be maintained and therefore the substitution with many amino acids may be acceptable. The substitution of D176 with Arg is also useful for generating mutants with an increased transglycosylation activity ratio.

The substitution of Y214 with an amino acid having a small side chain like Ala greatly reduces both of the activities and therefore Y214 will accept substitution with amino acids having a relatively large side chain. The substitution of Y214 with Phe is useful for generating mutants with an increased transglycosylation activity ratio.

The substitution of 5216 with an amino acid having a small side chain (preferably Ala or Val) allows transglycosylation activity to be maintained and hydrolytic activity to be reduced. This mutation is useful for generating mutants with an increased transglycosylation activity ratio.

The substitution of L245 with Ser maintained the activities and therefore the substitution of L245 with many amino acids may be acceptable. The substitution of L245 with Ser is also useful for generating mutants with an increased transglycosylation activity ratio.

Although N246 seems to resist acceptance of major change, the substitution of N246 with Asp greatly reduced hydrolytic activity while maintaining transglycosylation activity. Such a mutation is useful for generating mutants with an increased transglycosylation activity ratio.

The substitution of T275 with Ile maintained the activities and therefore the substitution of T275 with many amino acids may be acceptable. The substitution of T275 with Ile is also useful for generating mutants with an increased transglycosylation activity ratio.

It is believed that the hydrophobic interaction between W278 and the substrate sugar chain contributes to the activities. W278 may accept amino acids with a highly hydrophobic side chain, such as Tyr, Phe, Ala, Leu, and Ile.

The substitution of F283 with Ser allowed the activities to be maintained and therefore F283 may accept substitution with many amino acids. The substitution of F283 with Ser is also useful for generating mutants with an increased transglycosylation activity ratio.

The substitution of L306 with Ile causes less significant changes in the activities but tends to maintain transglycosylation activity and reduce hydrolytic activity and therefore the substitution may be useful for generating mutants with an increased transglycosylation activity ratio. The predicted conformation of the substitution product indicates that substitution with an amino acid with a bulky side chain or charged side chain may be unfavorable.

F307 may accept various amino acids such as His and Tyr. The substitution of F307 with His or Tyr greatly reduces hydrolytic activity rather than transglycosylation activity and is useful for generating mutants with an increased transglycosylation activity ratio.

The substitution of A310 with an amino acid having a side chain with a polar residue or a charged residue (preferably Asp, Glu, Lys, Ser, or the like) greatly reduces hydrolytic activity rather than transglycosylation activity. These mutations are useful for generating mutants with an increased transglycosylation activity ratio.

The substitution of E314 with Gln causes no large variation of the activities and may be acceptable.

As regards the amino acid substitution/mutation, the enzymes of the present invention include an amino acid sequence that preferably satisfies the property (A) of the present invention and has one or more amino acid substitutions selected from the mutations shown in SEQ ID NO: 23 (A128, N172, D176, Y214, 5216, L245, N246, T275, W278, F283, L306, F307, A310, E314, D333, 1434, V460, 1527, K569, P610, and H626 in SEQ ID NO: 1); more preferably an amino acid sequence that has at least one mutation selected from A128T (Rp2), D333G (Rp3), I434L (Rp3), V460A (Rp4), I527V (Rp3), K569T (Rp2-4), P610S (Rp3) and H626R (Rp3) in SEQ ID NO: 1; or an amino acid sequence that further has mutation at at least one amino acid of N172, D176, Y214, 5216, L245, N246, T275, W278, F283, L306, F307, A310, and E314 in the amino acid sequence, wherein a plurality of mutations may simultaneously occur and all of the mutations may occur.

Endo-β-N-acetylglucosaminidases have both hydrolytic activity and transglycosylation activity. The enzymes having high hydrolytic activity also hydrolyze, as substrates, the sugar chain that has been transferred to the acceptor molecule due to its transglycosylation activity. This may prevent such enzymes from appropriately producing the desired transglycosylated molecule. For this reason, such mutated enzymes for transglycosylation are also important in the synthesis of glycosylated compounds.

As mentioned above, it has been confirmed that some mutations at N172, D176, Y214, 5216, L245, N246, T275, F283, L306, F307, A310, and E314 in SEQ ID NO: 1 increase the transglycosylation activity of the enzymes of the present invention or greatly reduce the hydrolytic activity relative to the transglycosylation activity. Thus, these mutations are useful for designing a mutated enzyme for transglycosylation with an increased transglycosylation activity ratio (transglycosylation activity/hydrolytic activity). The present invention also provides such a mutated enzyme for transglycosylation. Specific mutations in the mutated enzyme for transglycosylation include a mutation in which N172 is substituted with Gln or Asp; a mutation in which D176 is substituted with Arg; a mutation in which Y214 is substituted with Phe; a mutation in which 5216 is substituted with Val; a mutation in which L245 is substituted with Ser; a mutation in which T275 is substituted with Ile; a mutation in which W278 is substituted with Phe or Tyr; a mutation in which F283 is substituted with Ser; a mutation in which L306 is substituted with Ile; a mutation in which F307 is substituted with Tyr; a mutation in which A310 is substituted with Asp; and a mutation in which E314 is substituted with Gln in SEQ ID NO: 1. The mutations introduced into the mutated enzymes for transglycosylation of the present invention may be at least one of these mutations. The mutations may be a single mutation or multiple mutations comprising some of these mutations. Preferable mutations are N172Q, N172D, W278F, N172Q/W278F, N172D/W278F, or Y214/L3061/F307Y.

Hydrolytic Activity and Transglycosylation Activity

The enzymes of the present invention have hydrolytic activity and/or transglycosylation activity on complex-type sugar chains. The activities represent a property exhibiting, at any temperature from 45 to 60° C., 40% or more of the maximal activity value.

The enzymes of the present invention have an activity of hydrolyzing various complex-type sugar chains as substrates. The enzymes are identified by assessing the activity of hydrolyzing SGP as a substrate to provide SG (10) according to the method described below.

In a hydrolytic reaction, a reaction solution (total volume: 100 μL) containing a 200 mM potassium phosphate buffer (pH 6.25), 69 mM SGP, and 0.02 μM enzyme (for blank, an equal volume of a buffer instead of the enzyme) (all concentrations listed represent the final concentration in the reaction solution) is prepared and incubated at a predetermined temperature for 18 hours. The resulting reaction solution and blank solution were analyzed by LC-MS to quantify SGP and SG (10) and calculate the hydrolysis rate and specific activity according to the formulae described below.

LC-MS analysis condition A

MS apparatus: 6130 Quadrupole LC-MS (Agilent Technologies, Inc.)

Ionization: ESI

Mode: Positive

HPLC: 1260 Infinity LC (Agilent Technologies, Inc.)

Column: Inertsil ODS-3 3 μm φ3.0×50 mm (GL Sciences Inc.)

Column temperature: 40° C.

Mobile phase A: $H_2O$+0.1% HCOOH

Mobile phase B: Acetonitrile+0.1% HCOOH

Gradient (mobile phase B %): 0% (0 min), 10% (5 min), 30% (7 min)

Flow rate: 0.6 mL/min

Hydrolysis Rate

Hydrolysis rate is calculated according to the following formula:

Hydrolysis rate (%)=the concentration of SG(10) after reaction(*M*)/the concentration of SGP in blank(*M*)×100

Specific Activity

Specific activity is calculated according to the following formula:

Specific activity(μmol/min/μg)=the amount of SG(10) produced(μmol)/the duration of reaction (min)/the amount of enzyme(μg)

The enzymes of the present invention have the activity of recognizing various sugar chain donors and acceptor molecules and transferring sugar chains. The enzymes are identified by assessing the activity of transferring the sugar chain of SGP used as a substrate to provide SG-A according to the method described below.

In a transfer reaction, a reaction solution (total volume: 30 μL) containing a 1.6 M potassium phosphate buffer (pH 6.25), 69 mM SGP, 690 mM GlcNAc-AcA, and 1.0 μM enzyme (for blank, an equal volume of a buffer instead of the enzyme) (all concentrations listed represent the final concentration in the reaction solution) is prepared and incubated at a predetermined temperature. The reaction solutions after 1 hour, 2 hours, 4 hours, 8 hours, 24 hours, 48 hours, and 96 hours and the blank solution were analyzed by LC-MS to quantify SGP, SG(10), and SG-A and calculate the hydrolysis rate and specific activity according to the formulae described below.

LC-MS analysis condition B

MS apparatus: 6130 Quadrupole LC-MS (Agilent Technologies, Inc.)

Ionization: ESI

Mode: Positive

HPLC: 1260 Infinity LC (Agilent Technologies, Inc.)

Column: Inertsil ODS-3 2 μm 02.1×50 mm (GL Sciences Inc.)

Column temperature: 40° C.

Mobile phase A: $H_2O$+0.1% HCOOH

Mobile phase B: Acetonitrile+0.1% HCOOH

Gradient (mobile phase B %): 0.8% (0 min), 8% (0.1 min), 8% (5 min)

Flow rate: 0.7 mL/min

Transfer Rate

Transfer rate is calculated according to the following formula:

Transfer rate (%)=the concentration of SG-A after reaction(*M*)/the concentration of SGP in blank (*M*)×100

Specific Activity

Specific activity is calculated according to the following formula:

Specific activity(μmol/min/mg)=the amount of SG-A produced(μmol)/the duration of reaction(min)/ the amount of enzyme(mg)

When hydrolytic activity and/or transglycosylation activity are determined according to the method described above at temperatures appropriately varying from, for example, 10° C. to 70° C. (for example, in 2, 3, 5, or 10° C. increments) and the maximum of the activity values calculated from all of the temperature conditions is set to 100%, the enzymes of the present invention exhibit, at any temperature condition from 45° C. to 60° C. (preferably at 50° C.), a relative activity value of 40% or more, preferably 50% or more, more preferably 60% or more, still more preferably 80% or more and most preferably the maximal activity value in the temperature range.

Specific activity is generally determined under the optimum temperature condition for the enzyme. The enzymes of the present invention exhibit a high specific activity. For example, Endo-Rp exhibits a specific activity of 0.21 μmol/min/μg when it uses 69 mM SGP as a substrate at 50° C. This specific activity is an excellent activity that is 30-times more than the specific activity of Endo-M at 37° C. (0.0071 μmol/min/μg).

The enzymes of the present invention are not limited to the enzymes and mutants specifically described in the Examples herein. The enzymes of the present invention include various polypeptides as long as they satisfy properties (A) and (B). The enzymes of the present invention may be those that exhibit at least one of their hydrolytic activity and transglycosylation activity at a certain level or higher, which level is preferably 0.5% or more, more preferably 1% or more, still more preferably 5% or more, even more preferably 10% or more, and most preferably 30% or more of the activity of the enzyme consisting of the amino acid sequence of SEQ ID NO: 1 under the temperature condition as described above.

Gene

The present invention further provides genes having nucleic acid sequences encoding the enzymes of the present invention as described above.

The genes can be cloned from nature (for example, thermophilic fungi, preferably fungi belonging to the genus *Rhizomucor*, and more preferably *R. pusillus* or *R. miehei*) as a gene encoding the present enzyme based on the gene information from *R. pusillus* or *R. miehei*. The genes can also be generated as a recombinant gene based on the amino acid sequence of the enzymes according to known genetic engineering techniques.

Nucleic acid sequences encoding the enzymes of the present invention encode a polypeptide that comprises an amino acid sequence that has 75% or more identity and 95% or more similarity to the amino acid sequence shown in SEQ ID NO: 1 and is an amino acid sequence different from the amino acid sequence of SEQ ID NO: 7. Examples of the nucleic acid sequences may include, for example, nucleic acid sequences naturally occurring in fungi as shown in SEQ ID NO: 8, 10, 12, 14, 16, or 18 (including the termination codon). Nucleic acids having nucleic acid sequences optimized for expression in *E. coli* can be generated by utilizing for example, GeneArt Strings DNA Fragments (manufactured by Thermo Fisher Scientific, Inc.) based on the amino acid sequences of the enzymes. The nucleic acid sequences of SEQ ID NOS: 9, 11, 13, 15, 17, and 19 are nucleic acid sequences designed based on the amino acid sequences of SEQ ID NO: 1 (Endo-Rp), 2 (Endo-Rp2), 3 (Endo-Rp3), 4 (Endo-Rp4), 5 (Endo-Rp5), and 6 (Endo-Rm), respectively. These nucleic acid sequences are optimized for expression in *E. coli* of the enzyme with a His tag (His×6) added to the C-terminus. By referring to these nucleic acid sequences, a nucleic acid sequence efficiently expressing a polypeptide having various modified amino acids, such as for example the amino acid sequence of SEQ ID NO: 23, in *E. coli* can be designed.

Specific examples of the nucleic acid sequences encoding the enzymes of the present invention can include nucleic acid sequences having 80% or more, preferably 95% or more, more preferably 95%, even more preferably 98% or more identity to the nucleic acid sequence shown in any of nucleotide positions 1 to 2088 of SEQ ID NOs: 8 to 17 and nucleotide positions 1 to 2091 of SEQ ID NOs: 18 to 19 (preferably nucleotide positions 1 to 2088 of SEQ ID NOs: 8 to 17 encoding Endo-Rp or homologs thereof) and nucleic acids encoding Leu-Ala-Lys-Leu-Leu in a region from positions 570 to 585 in each nucleic acid sequence.

Production and Purification of Enzyme

The present invention further provides a gene construct including a plasmid and an expression vector comprising a recombinant gene encoding an enzyme of the present invention; a host cell transformed with the gene construct; and a method of producing the enzyme of the present invention comprising collecting the enzyme of the present invention from the culture of the host cells. The gene encoding the enzyme of the present invention is introduced into a suitable plasmid/expression vector depending on the host cell type (including animal cells, plant cells, *E. coli*, and yeast; any cells commonly used in protein production or other cells can be appropriately selected) to be transformed with the plasmid/expression vector. The transformed cells are cultured under suitable conditions. The enzyme of the present invention can be collected from the culture.

The gene constructs for transformation can be generated according to known techniques using a vector or plasmid that is generally known in the art of genetic engineering and is selected depending on cell type in which the vector or plasmid is expressed. For example, vectors that can be used for expression in *E. coli* include, but are not limited to, pET vector, pCold vector, pFLAG vector, and the like.

Examples of the *E. coli* can include BL21 (DE3) and Origami (DE3).

Examples of the culture conditions of *E. coli* for producing the enzyme of the present invention include a method in which transformed bacterial culture is inoculated into 25 mL of TB medium (50 μg/mL Kanamycin) in a 100 mL flask and cultured with shaking at 37° C. overnight (160 rpm, 0/N). Another method which can also be used, but which is not limiting, comprises inoculating 20 mL of the preculture medium into 1 L of TB medium (50 μg/mL Kanamycin, 0.01% antifoam 204, 2 mM $MgSO_4$) in a 2.5 L baffled flask; culturing with shaking at 37° C. (200 rpm, 2 hours); lowering the incubator temperature to 16° C. and culturing for 3 hours, and thereafter adding IPTG at a final concentration of 0.2 mM; and further culturing it for 24 hours. Media that can be used include common media such as LB medium and M9 medium, in addition to TB medium.

The enzyme of the present invention can be collected by utilizing the physical properties of the enzyme appropriately in combination with any common purification technique. For convenient collection, the gene construct is previously designed to express the enzyme linked to a tag peptide such as a His-tag or a GST-tag so as to collect the enzyme by utilizing the affinity of the tag peptide. The tag peptide may be removed after purification but the enzyme linked to the tag peptide may be directly used for reactions including hydrolysis if the tag peptide has no effect on the enzymatic activity. The enzymes of the present invention include an enzyme having an amino acid sequence linked to such a tag peptide. Specific examples of the enzyme include amino acid sequences having a His-tag (His×6) linked to the C-terminus of the amino acid sequences of SEQ ID NOS: 1 to 6.

The enzymes of the present invention have excellent production efficiency in *E. coli* due to the properties of the amino acid sequences. The enzymes of the present invention exhibit an expression efficiency of 2 mg or more per 1 L of culture, preferably 4 mg or more, more preferably 8 mg or more, further preferably 12 mg or more, and even more preferably 15 mg or more per 1 L of culture when they are produced in *E. coli* under the culture conditions described above.

EXAMPLES

Hereinafter, the present invention will be specifically described with reference to the following Examples. The description in the Examples is an example of one embodiment of the present invention. These Examples are not intended to limit the present invention.

Protein concentration as described herein was quantified using a Microvolume Spectrophotometer NanoDrop 1000 (manufactured by Thermo Fisher Scientific, Inc.) or NanoDrop 2000 (manufactured by Thermo Fisher Scientific, Inc.).

In the Examples, when the hydrolytic activity of the enzyme endo-β-N-acetylglucosaminidase was determined, SGP and SG (10) were detected in the reaction solutions using the above-mentioned LC-MS analysis condition A. Hydrolysis rate and specific activity were calculated according to the above-mentioned formulae for calculation.

Example 1 Discovery of endo-β-N-acetylglucosaminidase Derived from *R. pusillus*

*R. pusillus* strains NBRC 9740, NBRC 9741, NBRC 9742, and NBRC 9743 were inoculated on a GSYFe slant (5% Glucose, 2% Soytone, 1% Yeast extract, 0.05% $FeSO_4.7H_2O$, 1.5% agar) and cultured at 40° C. for 5 days. Fungal cells were collected and disrupted in 2 mL of a 100 mM potassium phosphate buffer (pH 6.25) using a glass homogenizer followed by filter sterilization to give a crude enzyme solution.

Figure 2:
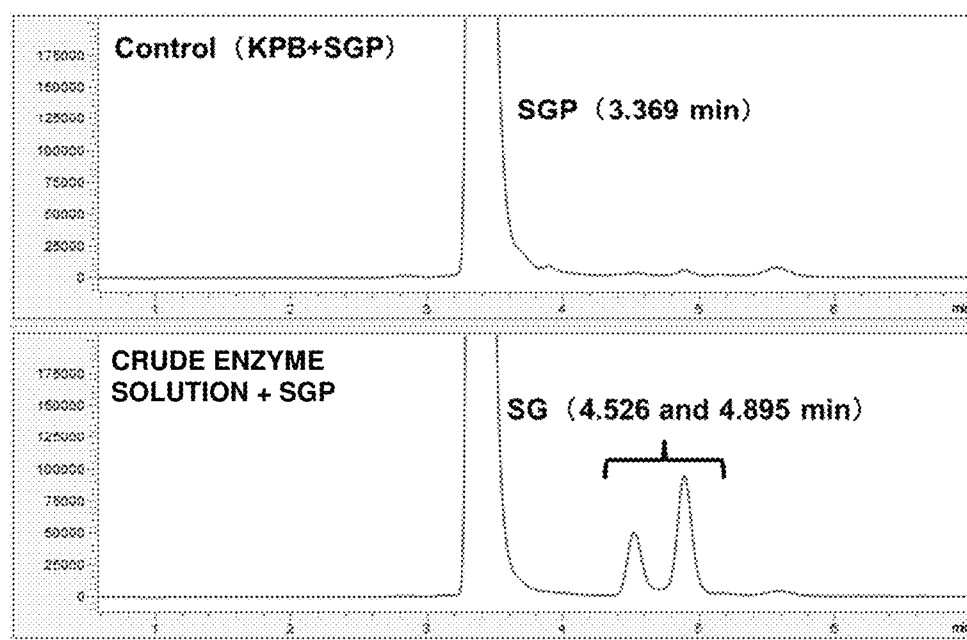
FIG. 2 represents charts showing the results of LC-MS analysis of SGP solution before enzyme treatment (upper panel) and crude solution after enzyme treatment (lower panel) under analysis condition A. The large peak detected at 3 to 4 minutes represents SGP and the peaks detected around 4.5 to 5 minutes represent SG(10).

To 50 μL of the crude enzyme solution, 3 mg of SGP was added (to a final concentration of 21 mM) and incubated at 50° C. The reaction solution was analyzed by LC-MS and disappearance of SGP and production of SG (10) were observed (FIG. 2). Thus, we considered that *R. pusillus* NBRC 9742 has an endo-β-N-acetylglucosaminidase.

Figure 3:
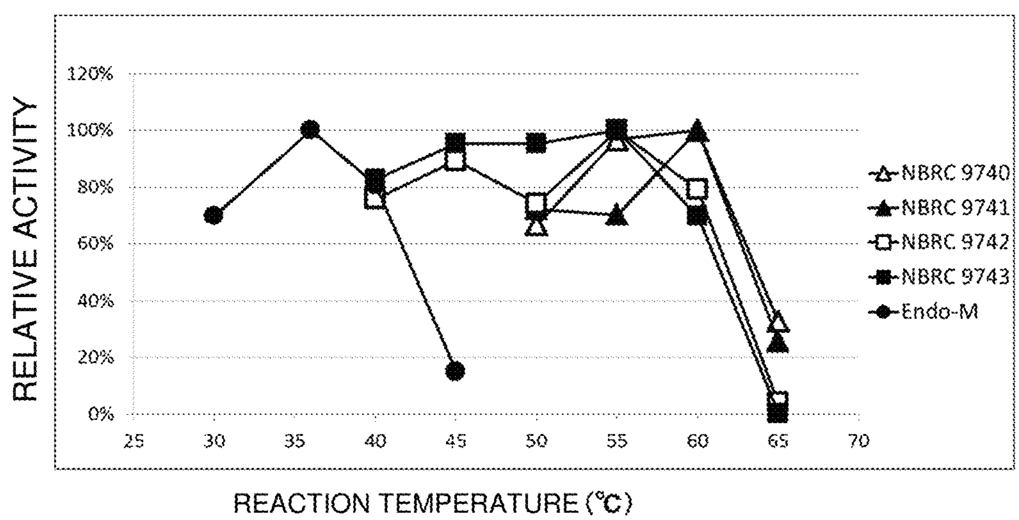
FIG. 3 is a graph showing the temperature dependence of hydrolytic activities of crude enzymes derived from various *R. pusillus* strains (NBRC 9740 (open triangle), NBRC 9741 (filled triangle), NBRC 9742 (open square), and NBRC 9743 (filled square)) and Endo-M (filled circle) on SGP. X axis represents the reaction temperature (° C.) and Y axis represents the hydrolysis rate.

Furthermore, hydrolytic reactions were performed at varying reaction temperatures. In each sample, relative activity was calculated such that the activity at the temperature at which the reaction progressed most efficiently was set as 100%. The results are shown in FIG. 3. It can be confirmed that the optimum temperature of the crude enzyme derived from *R. pusillus* is 55° C. or more although Endo-M (manufactured by Tokyo Chemical Industry Co., Ltd.) used as a comparative control was inactivated at 45° C.

Example 2 Cloning of endo-β-N-acetylglucosaminidase Gene Derived from *R. pusillus*

The method described below was used to clone an endo-β-N-acetylglucosaminidase gene from *R. pusillus* strain NBRC 9742 and extract the related sequence based on the published genomic sequence.

(1) Gene Cloning from Microorganisms

First, *R. pusillus* strain NBRC 9742 was inoculated on a GSYFe slant and cultured at 40° C. for 5 days. Fungal cells were collected together with a metalcone into a 2 mL screw-capped microtube and frozen at −80° C. The fungal cells were repeatedly disrupted using a Multi-beads Shocker (Yasui Kikai Corporation) at 2,000 rpm through 5 cycles of on-time 30 seconds and off-time 30 seconds while cooling the frozen sample at 4° C. mRNA solution was obtained from this sample using a NucleoSpin RNA Plant (MACHEREY-NAGEL GmbH & Co. KG) and an Oligotex-dT30<Super> mRNA Purification Kit (Takara Bio Inc.).

The resulting mRNA was used as a template with primer 1 (SEQ ID NO: 22) and 3'-Full RACE Core Set (Takara Bio Inc.) to amplify the gene encoding the endo-β-N-acetylglucosaminidase and the amplified product was cloned into a pUC19 vector. This gene consists of 2091 bases including the termination codon (SEQ ID NO: 8) and encodes a protein with a molecular weight of 78,874 consisting of 696 amino acid residues (SEQ ID NO: 1). This protein was named as Endo-Rp.

Endo-Rp homologs Endo-Rp2 (the amino acid sequence of SEQ ID NO: 2), Endo-Rp3 (the amino acid sequence of SEQ ID NO: 3), and Endo-Rp4 (the amino acid sequence of SEQ ID NO: 4) were also cloned from *R. pusillus* strains NBRC 9740, 9741, and 9743 in a similar manner. NBRC 9740 had only the Endo-Rp2 sequence while NBRC 9741 had the Endo-Rp2 and the Endo-Rp3 sequences and NBRC 9743 had the Endo-Rp3 and the Endo-Rp4 sequences. Each of the sequences had 99% identity to the amino acid sequence of Endo-Rp.

(2) Comparison with Published Genomic Sequence

The sequences of Endo-Rp, Endo-Rp2, Endo-Rp3, and Endo-Rp4 were compared with putative sequences published in the database provided by The Genozymes Project. The amino acid corresponding to Lys at position 193 in SEQ ID NO: 1 was substituted with Asn-Thr-Tyr-Tyr-Ile-Arg in SEQ ID NO: 7, leading to the different length of the protein (FIG. 4). Genomic DNA was extracted from *R. pusillus* strain NBRC 9742 and the full-length ORF sequence of the Endo-Rp gene was amplified by PCR and analyzed. The analysis results indicated that the putative sequence of the strain with the published genome has different predicted positions of the introns. Therefore, this could result in the difference in amino acid sequences as described above.

The amino acid sequence of Endo-Rp was also used to perform a BLAST search against the database provided by NCBI. Results from the search showed that the genomic sequence of *Rhizomucor miehei* strain CAU432 which is a related species of *R. pusillus* has the sequence corresponding to Endo-Rp. This sequence information was used to identify the nucleic acid sequence expected to encode an endo-β-N-acetylglucosaminidase (SEQ ID NO: 18) and its amino acid sequence (SEQ ID NO: 6). The protein consisting of this amino acid sequence was named as Endo-Rm. Endo-Rm was 67% homologous to Endo-Rp.

Example 3 Expression of Endo-Rp in *E. coli*

A nucleic acid sequence (SEQ ID NO: 15) optimized for heterologous expression in *E. coli* was designed from the fungus-derived endo-β-N-acetylglucosaminidase gene obtained in Example 2 using GeneArt Strings DNA Fragments provided by Thermo Fisher Scientific, Inc. The sequence was used to generate a gene encoding a polypeptide with 6×His-tag added to the C-terminus of Endo-Rp. This was cloned into a pET24b(+) vector, which was then introduced into *E. coli* BL21 (DE3) to be transformed. The bacterial culture after transformation was inoculated into 25 mL of TB medium (50 μg/mL Kanamycin) in a 100 mL flask and cultured with shaking at 37° C. overnight (160 rpm, 0/N). 20 mL of the preculture medium was inoculated into 1 L of TB medium (50 μg/mL Kanamycin, 0.01% antifoam 204, 2 mM $MgSO_4$) in a 2.5 L baffled flask and cultured with shaking at 37° C. (200 rpm, 2 hours). After lowering the incubator temperature to 16° C. and culturing for 3 hours, IPTG was added at a final concentration of 0.2 mM and additional culturing was performed for 24 hours.

Harvested bacterial cells were suspended in 100 mL of a binding buffer (50 mM HEPES (pH 8.0), 0.5 M NaCl, 20 mM Imidazole, 5% Glycerol), sonicated, and centrifuged. The supernatant from centrifugation was purified with a Ni Sepharose 6 Fast Flow and a HiLoad 16/60 Superdex 200 pg column (GE Healthcare). The yield (calculated from $A_{280}$ and extinction coefficient) was 16.9 mg/L of broth.

Similar heterologous expression was also performed for Endo-Rp homologs and Endo-Rm. Also performed was the expression of Endo-Rp homologs including the enzyme identified in Example 2 and the sequence (Endo-Rp5, SEQ ID NO: 5) that has a Lys residue substituted for Asn-Thr-Tyr-Tyr-Ile-Arg from positions 193 to 198 in SEQ ID NO: 7 as in other homologs. The Endo-Rm gene sequence optimized for *E. coli* (SEQ ID NO: 20) was obtained by utilizing GeneArt Strings DNA Fragments (Thermo Fisher Scientific, Inc.) based on the amino acid sequence of SEQ ID NO: 6. Other genes were obtained by introducing a mutation into a vector for *E. coli* expression of Endo-Rp comprising the base sequence of SEQ ID NO: 15 according to the standard protocol of the PrimeSTAR Mutagenesis Basal Kit (Takara Bio Inc.) (Endo-Rp2: SEQ ID NO: 16, Endo-Rp3: SEQ ID NO: 17, Endo-Rp4: SEQ ID NO: 18, Endo-Rp5: SEQ ID NO: 19).

The expression was induced under the above-mentioned conditions except that the main culture was in 100 mL of TB medium in a 500 mL baffled flask. Harvested bacterial cells were suspended in 6 mL of a binding buffer, sonicated, and centrifuged. The supernatant from centrifugation was purified with a His GraviTrap column (GE Healthcare).

After purification, the bands of expressed proteins except for SEQ ID NO: 7 were observed on SDS-PAGE. The yield of each protein was 2.067 mg (20.67 mg/L of culture) for Endo-Rp, 2.139 mg (21.39 mg/L of culture) for Endo-Rp2, 2.765 mg (27.65 mg/L of culture) for Endo-Rp3, 2.301 mg (23.01 mg/L of culture) for Endo-Rp4, 2.187 mg (21.87 mg/L of culture) for Endo-Rp5, and 1.650 mg (16.50 mg/L of culture) for Endo-Rm.

Example 4 Hydrolytic Activity of Endo-Rp on Complex-Type Sugar Chains

The hydrolytic activity of enzymes obtained in Example 3 was determined using the above-mentioned method. Endo-M (manufactured by Tokyo Chemical Industry Co., Ltd.), EndoS, and Endo-Om were used as a comparative control for this determination.

Figure 5:
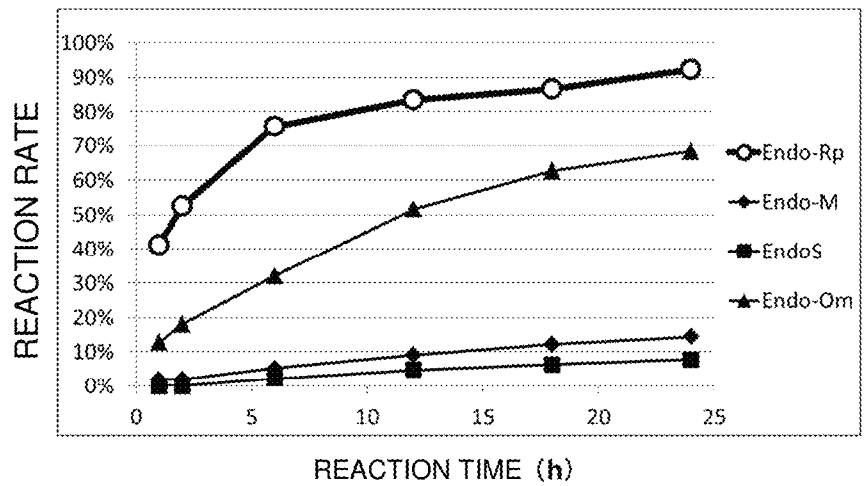
FIG. 5 is a graph showing the time-dependent change of hydrolytic activities of Endo-Rp (open circle), Endo-M (filled circle), Endo-S(filled square), and Endo-Om (filled triangle) on SGP. X axis represents the duration after the start of reaction and Y axis represents the hydrolysis rate.

Reaction solutions (total volume: 100 μL) containing a 200 mM potassium phosphate buffer (pH 6.25), 69 mM SGP, and 0.02 μM enzyme (all concentrations listed represent the final concentration in the reaction solutions) were prepared. The reaction solution containing Endo-Rp or Endo-Om was incubated at 50° C. while the reaction solution containing Endo-M or Endo-S was incubated at 37° C. The reaction solutions were sampled after 1 hour, 2 hours, 6 hours, 12 hours, 18 hours, and 24 hours and analyzed by LC-MS under the above-mentioned analysis condition A. The time-dependent change of the reaction rates is shown in FIG. 5. The specific activities were 0.21 μmol/min/μg for Endo-Rp, 0.0071 μmol/min/μg for Endo-M, 0.0022 μmol/min/μg for Endo-S, and 0.060 μmol/min/μg for Endo-Om. The specific activity of Endo-Rp was 30-times higher than that of Endo-M, 100-times higher than that of Endo-S, and 4-times higher than that of Endo-Om. This demonstrates that Endo-Rp has very high hydrolytic activity on SGP as compared with known enzymes.

Endo-Rp homologs expressed and purified in Example 3 were also determined for their activities. The reaction solutions (total volume: 30 μL) containing a 200 mM potassium phosphate buffer (pH 6.25), 69 mM SGP, and 0.2 μM enzyme (all concentrations listed represent the final concentration in the reaction solutions) were prepared and incubated at 50° C. for 1 hour. The hydrolysis rate after 1 hour was 87% for Endo-Rp, 91% for Endo-Rp2, 84% for Endo-Rp3, 79% for Endo-Rp4, 94% for Endo-Rp5, and 23% for Endo-Rm. This demonstrates that Endo-Rp2, Endo-Rp3, Endo-Rp4, and Endo-Rp5 have hydrolytic activity somewhat similar to that of Endo-Rp on SGP.

Example 5 Determination of Optimal Reaction Condition for Endo-Rp

Optimal reaction temperature and pH for Endo-Rp were determined.

Figure 6:
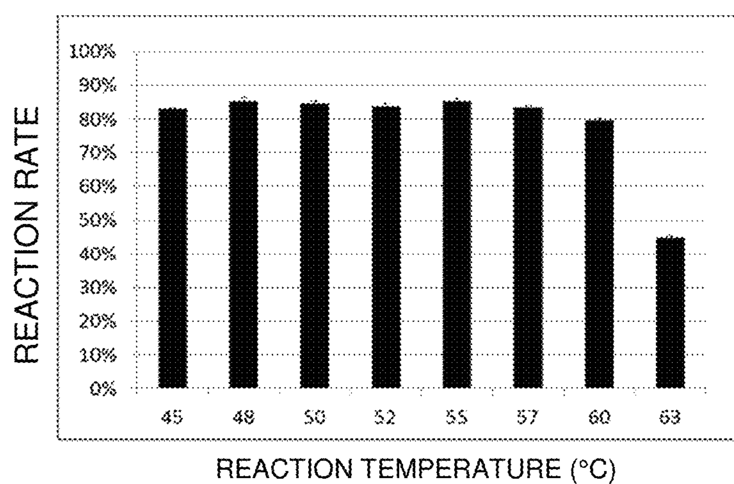
FIG. 6 is a graph showing the temperature dependence of hydrolytic activity of Endo-Rp on SGP. X axis represents the reaction temperature (° C.) and Y axis represents the hydrolysis rate.

For the determination of reaction temperature, the reaction solutions (total volume: 100 μL) containing a 200 mM potassium phosphate buffer (pH 6.25), 69 mM SGP, and 0.02 μM enzyme (all concentrations listed represent the final concentration in the reaction solutions) were prepared and incubated at a temperature of 45, 50, 52, 55, 57, 60, and 63° C. for 18 hours to calculate the hydrolysis rates. The results are shown in FIG. 6.

Figure 7:
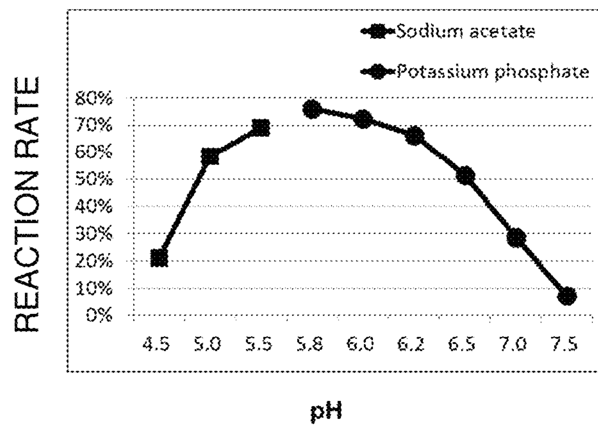
FIG. 7 is a graph showing the pH dependence of hydrolytic activity of Endo-Rp on SGP. X axis represents the pH value of the reaction solutions and Y axis represents the hydrolysis rate.

For the determination of reaction pH, the reaction solutions (volume: 100 μL) at pH 4.5, 5.0, 5.5, 5.8, 6.0, 6.2, 6.5, 7.0, and 7.5 containing a 200 mM sodium acetate buffer or potassium phosphate buffer, 69 mM SGP, and 0.02 μM enzyme (all concentrations listed represent the final concentration in the reaction solutions) were prepared and incubated at 50° C. for 23 hours to calculate the hydrolysis rates. The results are shown in FIG. 7.

The results of the determination showed that the optimal reaction temperature for Endo-Rp is around 55° C. and the optimal reaction pH is around 5.8.

Example 6 Transglycosylation Activity of Endo-Rp

Whether Endo-Rp has transglycosylation activity was determined as follows.

The reaction solutions (total volume: 30 μL) containing a 1.6 M potassium phosphate buffer (pH 6.25), 69 mM SGP, 690 mM (GlcNAc-)Asn (manufactured by WATANABE CHEMICAL INDUSTRIES, LTD.) and 0.1 μM enzyme (all concentrations listed represent the final concentration in the reaction solutions) were prepared and incubated at 50° C. for 4 hours.

The reaction solutions were analyzed by LC-MS under the conditions as described below.

MS apparatus: 6130 Quadrupole LC-MS (Agilent Technologies, Inc.)

Ionization: ESI

Mode: Positive

HPLC: 1260 Infinity LC (Agilent Technologies, Inc.)

Column: Inertsil ODS-3 2 μm 02.1×50 mm (GL Sciences Inc.)

Column temperature: 40° C.

Mobile phase A: $H_2O$+0.1% HCOOH

Mobile phase B: Acetonitrile+0.1% HCOOH

Gradient (mobile phase B %): 0.8% (0 min), 2% (5 min), 2% (6 min)

Flow rate: 0.7 mL/min

Figure 8:
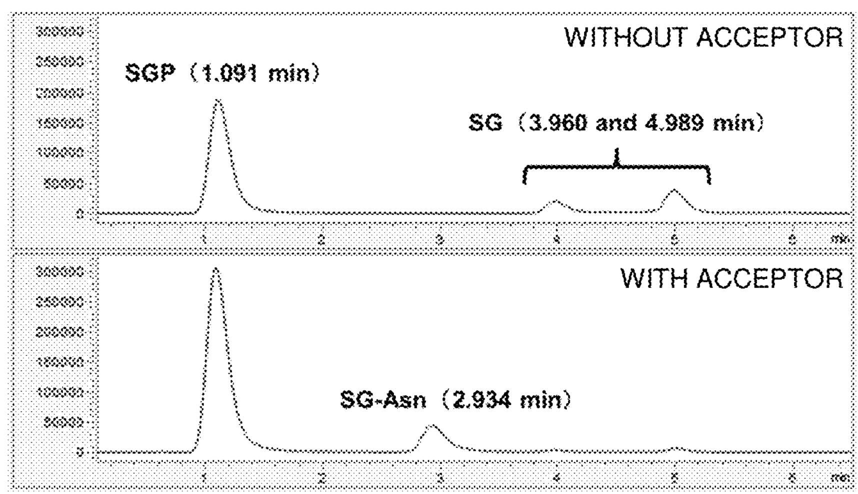
FIG. 8 represents charts showing the results of LC-MS analysis of the reaction solution of Endo-Rp in the presence of SGP alone (upper panel) or SGP+acceptor ((GlcNAc-)Asn) (lower panel). The large peak detected near 1 minute represents SGP, and the peaks detected at around 4 to 5 minutes represent SG(10), and the peak detected at around 3 minutes represents (SG-)Asn.

The results are shown in FIG. 8. The peaks of SGP, which is a donor, and SG (10), which is a hydrolysate, were only detected under a condition without an acceptor. The peaks of SG(10) and (SG-)Asn, which is a transglycosylation reaction product, were detected under the conditions with (GlcNAc-)Asn added as an acceptor. These results demonstrate that Endo-Rp has transglycosylation activity.

Example 7 Generation of Endo-Rp N172Q

To obtain an enzyme with suppressed hydrolytic activity on sugar chains while retaining transglycosylation activity of Endo-Rp, asparagine (N) at position 172, which is the active center, was substituted with glutamine (Q) to generate an N172Q variant. The N172Q variant was prepared by substituting AAC from positions 514 to 516 with CAA in the base sequence encoding Endo-Rp shown in SEQ ID NO: 9 using the method as described in Example 3.

Transglycosylation activity was assessed as follows. The reaction solution (total volume: 30 μL) containing a 1.6 M potassium phosphate buffer (pH 6.25), 69 mM SGP, 690 mM (GlcNAc-)Asn, and 1.0 μM enzyme (all concentrations listed represent the final concentration in the reaction solution) was prepared and incubated at 50° C. The reaction solution was sampled after 20 minutes, 40 minutes, 1 hour, 2 hours, 4 hours, 8 hours, 20 hours, 24 hours, and 48 hours of reaction and analyzed by LC-MS under the conditions as described in Example 6.

Figure 9:
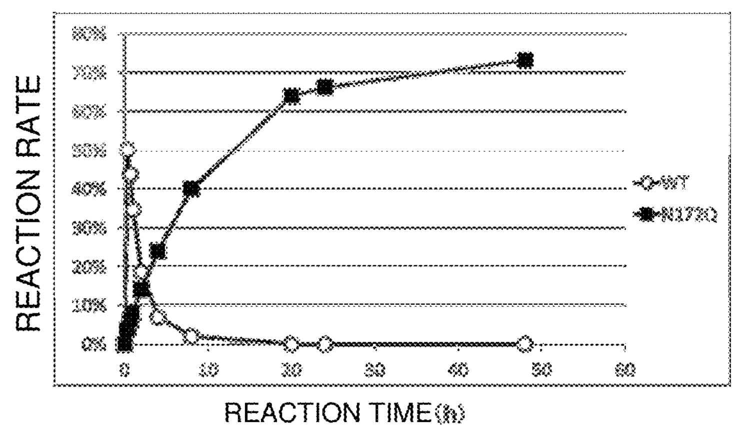
FIG. 9 is a graph showing the time-dependent change of transglycosylation activities of Endo-Rp (open circle) and Endo-Rp N172Q (filled square). X axis represents the duration (hour) after the start of reaction and Y axis represents the transglycosylation rate (%).

The time-dependent change of the reaction rates is shown in FIG. 9. Endo-Rp WT rapidly hydrolyzed a transglycosylation reaction product (SG-)Asn whereas the N172Q variant caused less hydrolysis, which demonstrated that the N172Q variant produces (SG-)Asn in a high yield.

Example 8 Modification of Endo-Rp

To obtain an enzyme with increased transglycosylation activity in comparison with that of the Endo-Rp N172Q variant, modification was attempted. Various mutants listed in Table 1 were designed based on the structures of Endo-A (PDB ID: 3FHQ) and Endo-D (PBD ID: 2W92). Hydrolytic activity and transglycosylation activity of these mutants on SGP were determined.

Transglycosylation activity was assessed as follows. The reaction solution (total volume: 30 μL) containing a 1.6 M potassium phosphate buffer (pH 6.25), 69 mM SGP, 690 mM GlcNAc-AcA, and 1.0 μM enzyme (all concentrations listed represent the final concentration in the reaction solution) was prepared and incubated at 50° C. The reaction solution was sampled after 1 hour, 2 hours, 4 hours, 8 hours, 24 hours, 48 hours, and 96 hours of reaction and analyzed by LC-MS under the above-mentioned LC-MS analysis condition B.

Hydrolytic activity was assessed as follows. The reaction solution (total volume: 20 μL) containing a 1.6 M potassium phosphate buffer (pH 6.25), 69 mM SG-A, and 0.2 μM enzyme (all concentrations listed represent the final concentration in the reaction solution) was prepared and incubated at 50° C. The reaction solution was sampled after 1 hour, 2 hours, 4 hours, 8 hours, 24 hours, 48 hours, and 72 hours of reaction and analyzed by LC-MS under the above-mentioned LC-MS analysis condition B.

Table 1 shows the relative specific activities (hydrolysis and transglycosylation) of each variant when specific activities for transfer and hydrolysis of Endo-Rp were set to 100. The results showed that variants with mutations N172A, N172C, N172D, N172E, N172G, N172H, N172I, N172M, N172S, N172T, N172V, D176R, Y214F, S216V, L245S, N246D, T275I, F283S, L3061, F307Y, F307H, A310D, and E314Q had suppressed hydrolytic activity with maintained transglycosylation activity and an increased transglycosylation activity ratio (transglycosylation activity/hydrolytic activity; the ratio of transfer/hydrolysis in the table). Variants with mutations W278F and W278Y had also both increased transglycosylation activity and hydrolytic activity but decreased the transglycosylation activity ratio.

TABLE 1

| Mutant | Relative transglycosylation activity % | Relative hydrolysis activity % | Ratio of transfer/hydrolysis |
|---|---|---|---|
| WT | 100 | 100 | 1.00 |
| N172Q | 25 | 6.7 | 3.71 |
| N172H | 16 | 4.4 | 3.59 |
| N172A | 9.5 | 2.2 | 4.27 |
| N172C | 6.2 | 3.1 | 2.01 |
| N172D | 48 | 27 | 1.81 |
| N172E | 9.2 | 5.3 | 1.74 |
| N172F | ND | 1.4 | — |
| N172G | 10 | 2.4 | 4.12 |
| N172I | 13 | 3.3 | 3.86 |
| N172K | ND | 1.5 | — |
| N172L | ND | 1.7 | — |
| N172M | 6.7 | 3.2 | 2.13 |
| N172P | 0.67 | 0.94 | 0.71 |
| N172R | ND | 0.34 | — |
| N172S | 6.7 | 5.8 | 1.16 |
| N172T | 11 | 6.2 | 1.75 |
| N172V | 12 | 6.6 | 1.83 |
| N172W | ND | 0.15 | — |
| N172Y | ND | 0.36 | — |
| N172Q/E126A | 0.15 | 0.36 | 0.42 |
| N172Q/Y214F | 5.5 | 3.1 | 1.77 |
| N172Q/Y214A | 0.16 | 0.48 | 0.33 |
| N172Q/V223R | 0.020 | 0.30 | 0.05 |
| N172Q/W225H | 0.92 | 0.54 | 1.69 |
| N172Q/W248N | 0.55 | 1.2 | 0.45 |
| N172Q/N246L | ND | 0.32 | — |
| N172Q/N246A | ND | ND | — |
| N172Q/Y247F | 2.0 | 1.0 | 1.98 |
| N172Q/W278E | 0.080 | 0.18 | 0.44 |
| N172Q/W278R | ND | 0.23 | — |
| N172Q/W278F | 28 | 8.1 | 3.46 |
| N172Q/W278Y | 29 | 9.5 | 3.02 |
| N172Q/F307Y | 4.2 | 1.5 | 2.86 |
| N172Q/A310D | 0.60 | 0.60 | 0.99 |
| W278F | 93 | 155 | 0.60 |
| W278F/D176R | 104 | 129 | 0.81 |
| W278F/Y214F | 189 | 98 | 1.92 |
| W278F/S216V | 65 | 13 | 5.17 |
| W278F/L245S | 120 | 74 | 1.63 |
| W278F/N246D | 15 | 0.60 | 24.71 |
| W278F/N246V | ND | ND | — |
| W278F/T275I | 156 | 129 | 1.21 |
| W278F/D276N | 2.2 | 0.46 | 4.83 |
| W278F/R280E | ND | 0.080 | — |
| W278F/F283S | 119 | 50 | 2.38 |
| W278F/L306I | 113 | 141 | 0.80 |
| W278F/F307Y | 207 | 62 | 3.32 |
| W278F/F307H | 22 | 9.5 | 2.31 |
| W278F/A310D | 93 | 23 | 3.98 |
| W278F/E314Q | 95 | 141 | 0.67 |
| W278F/N172D | 34 | 33 | 1.01 |
| W278F/N172D/D176R | 20 | 19 | 1.06 |
| W278F/N172D/Y214F | 15 | 6.6 | 2.34 |
| W278F/N172D/S216V | 1.3 | ND | — |
| W278F/N172D/L245S | 19 | 14 | 1.33 |
| W278F/N172D/N246D | 0.17 | ND | — |
| W278F/N172D/N246V | ND | ND | — |
| W278F/N172D/T275I | 22 | 19 | 1.19 |
| W278F/N172D/D276N | 0.11 | ND | — |
| W278F/N172D/R280E | ND | ND | — |
| W278F/N172D/F283S | 19 | 5.8 | 3.36 |
| W278F/N172D/L306I | 33 | 27 | 1.20 |

TABLE 1-continued

| Mutant | Relative transglycosylation activity % | Relative hydrolysis activity % | Ratio of transfer/ hydrolysis |
|---|---|---|---|
| W278F/N172D/F307Y | 14 | 1.5 | 9.43 |
| W278F/N172D/F307H | 2.3 | 0.16 | 14.05 |
| W278F/N172D/A31OD | 8.2 | 0.87 | 9.41 |
| W278F/N172D/E314Q | 18 | 22 | 0.79 |
| N172Q/Y214F/F307Y | 0.25 | 0.13 | 1.85 |
| Y214F/F307Y | 20 | 6.6 | 3.03 |
| Y214F/L306I/F307Y | 34 | 8.3 | 4.12 |

ND: Not detected.

The invention claimed is:

1. A polypeptide having the following properties (A) and (B):

(A) the polypeptide (1) consisting of an amino acid sequence of any one of SEQ ID NOS: 1 to 5 or (2) having substitution and/or addition of 10 or fewer amino acids in the amino acid sequence of any one of SEQ ID NOS: 1 to 5, wherein amino acids D276, V223, W225, Y247, and W248 in the sequence remain unchanged and is an amino acid sequence different from the amino acid sequence of SEQ ID NO: 7; and (B) the polypeptide exhibits, at any temperature from 45 to 60° C., endo-beta-N acetylglucosaminidase activity on complex sugar chains.

2. The polypeptide according to claim 1, wherein the polypeptide consists of an amino acid sequence of any of SEQ ID NOS: 1 to 5.

3. The polypeptide according to claim 1, wherein the polypeptide has an amino acid sequence satisfying the property (A) and wherein the polypeptide has at least one substitution selected from a group of: substitution in amino acid sequence of any one of SEQ ID NOS: 1 to 5, wherein the group of substitution consists of a substitution in which N172 is substituted with Gln, Asp, Gly, Ala, Phe, Cys, His, Ile, Ser, Thr, Val, Met, Glu, Lys, Leu, Pro, Arg, Trp, or Tyr; a substitution in which D176 is substituted with Arg; a substitution in which Y214 is substituted with Phe; a substitution in which S216 is substituted with Ala or Val; a substitution in which L245 is substituted with Ser; a substitution in which N246 is substituted with Asp; a substitution in which T275 is substituted with Ile; a substitution in which W278 is substituted with Tyr, Phe, Ala, Leu, or Ile; a substitution in which F283 is substituted with Ser; a substitution in which L306 is substituted with Ile; a substitution in which F307 is substituted with His or Tyr; a substitution in which A310 is substituted with Asp, Gln, Lys, or Ser; and a substitution in which E314 is substituted with Gln.

4. The polypeptide according to claim 3, wherein the polypeptide has a substitution in at least one amino acid selected from N172, D176, Y214, S216, L245, N246, T275, L306, F307, and A310.

5. The polypeptide according to claim 3, wherein the polypeptide has a substitution in which W278 is substituted with Phe or Tyr.

6. A polynucleotide encoding the polypeptide according to claim 1.

7. The polynucleotide according to claim 6, having a nucleotide sequence of any of the nucleotide sequences from nucleotide positions 1 to 2088 of SEQ ID NOS: 8 to 17.

8. An expression plasmid comprising the polynucleotide according to claim 6.

9. A host cell transformed with the plasmid according to claim 8.

10. The host cell according to claim 9, wherein the host cell is *E. coli* transformed with a plasmid comprising a polynucleotide comprising the nucleotide sequence from nucleotide positions 1 to 2088 of SEQ ID NO: 9, 11, 13, 15, or 17.

11. A method of producing the polypeptide according to claim 1, comprising culturing the host cells transformed with a plasmid comprising the polynucleotide encoding the polypeptide according to claim 1, and collecting the polypeptide according to claim 1 from the resulting culture.

12. A reagent comprising the polypeptide according to claim 1.

* * * * *

SEQUENCE LISTING

```
<160> NUMBER OF SEQ ID NOS: 23

<210> SEQ ID NO 1
<211> LENGTH: 696
<212> TYPE: PRT
<213> ORGANISM: Rhizomucor pusillus

<400> SEQUENCE: 1

Met Pro Ser Leu Glu Leu Gln Gln Ala Ala Asp Thr Arg Leu Phe Glu
1               5                   10                  15

Ser Met Pro Leu Gln Thr Met Asn Glu Leu Gly Ser Trp Glu Pro Ser
            20                  25                  30

Asn Ala Ser Arg Ala Asn Ile Ala Thr Ile Pro Leu His Gln Arg Ser
        35                  40                  45

Asn Leu Asp Pro Ala Glu Pro Arg Leu Ile Val Thr His Asp Met Ala
    50                  55                  60

Gly Gly Tyr Lys Glu Asp Ser Asn Ile Gln Gly Asn Thr Tyr Asp Thr
65                  70                  75                  80

Ile Tyr Ser Cys Gln Tyr Trp Gln Tyr Val Asp Thr Phe Ile Tyr Phe
                85                  90                  95

Ser His His Arg Val Thr Ile Pro Pro Val Asn Trp Ile Asn Ala Cys
            100                 105                 110

His Arg Asn Gly Val Lys Thr Leu Gly Thr Phe Ile Val Glu Gly Ala
        115                 120                 125

Ala Gly Met Phe Ala Leu Glu Arg Phe Val Tyr Gly Pro Glu Pro Gly
    130                 135                 140

Gln Arg Asn Ser Trp Ser Pro Tyr Tyr Ala Asp Lys Leu Val Asp Ile
145                 150                 155                 160

Ala Glu Phe Tyr Gly Phe Asp Gly Trp Leu Leu Asn Ile Glu Ser Asp
                165                 170                 175

Phe Phe Pro Leu Tyr Arg Asn Pro Ser Leu Lys Ala Ile His Leu Ala
            180                 185                 190

Lys Leu Leu Arg Tyr Leu Lys Asn Ala Met His Ala Arg Val Pro Gly
        195                 200                 205

Ser Glu Ile Ile Trp Tyr Asp Ser Met Thr Thr Asn Gly Ser Val Gln
    210                 215                 220

Trp Gln Asn Asn Ile Thr Pro Lys Asn Ser Ile Phe Phe Glu Ala Ala
225                 230                 235                 240

Asp Gly Ile Phe Leu Asn Tyr Trp Trp Asn Ala Thr Val Pro Pro Leu
                245                 250                 255

Ala Leu Gln Val Ala His Arg Leu Gly Arg Gln Gly Ser Asp Val Tyr
            260                 265                 270

Phe Gly Thr Asp Val Trp Gly Arg Gly Thr Phe Gly Gly Gly Gly Phe
        275                 280                 285

Asp Ser Tyr Leu Ala Val Gly Thr Ala Arg Ala Phe Lys Thr Ser Ser
```

```
    290                 295                 300

Ala Leu Phe Gly Thr Ala Trp Ile Tyr Glu His Phe Gly Lys Lys Asp
305                 310                 315                 320

Phe Glu Leu Met Asp Arg Leu Leu Trp Leu Gly Gly Asp Gln Ser Glu
                325                 330                 335

Tyr Pro Ala Gln Glu Gly Glu Gln Asn Arg Thr Val Lys Val Thr Ser
            340                 345                 350

His Leu Gly Arg His Pro Gly Ile Ala Asp Val Ser Pro Val Arg Ser
        355                 360                 365

Ala Pro Gly Lys Thr Trp Phe Ala Thr Trp Phe Asp Arg Gly Tyr Gly
    370                 375                 380

Thr Gly Phe Tyr Tyr Gln Gly Lys Lys Leu Leu Ser Gln Pro Trp Ser
385                 390                 395                 400

His Leu Ser His Gln Ser Ile Pro Pro Asn Leu Ile Ala Arg Leu Gln
                405                 410                 415

Arg Glu Glu Asn His Gly Leu Ser Tyr Phe Leu Ala Asp Asp Asp Ala
            420                 425                 430

Tyr Ile Gly Gly Thr Ser Leu Leu Ile Ala Ala Glu Ile Thr Gln Glu
        435                 440                 445

Arg Gln Leu Pro Leu Tyr Gln Leu Glu Tyr Asp Val Thr Glu Gly Cys
    450                 455                 460

Glu Val Gln Phe Ile Tyr Lys Ser Pro Glu Pro Asp Met Gln Gly Lys
465                 470                 475                 480

Ile Asp Ile Tyr Leu Asn Leu Gln Val Thr Asp Ile Leu Pro Asp Glu
                485                 490                 495

Leu Ala Phe Tyr Trp Gln Asp Val Thr Asp Ala Ser Ser Gln Ala Asp
            500                 505                 510

Ala Thr Thr Ala Met Arg Leu Tyr Leu Asn Glu Asn Thr Val Ile Tyr
        515                 520                 525

Leu Lys Pro Ser Arg Lys Gln Glu Leu Ala Glu Gly Trp Leu Leu Cys
    530                 535                 540

Ser Val Arg Val Pro Pro Thr Tyr Pro Leu Gly Ile Ala Thr Ile Lys
545                 550                 555                 560

Glu Leu Gly Ile His Val Asp Gly Lys Glu Thr Val Leu Phe Arg Leu
                565                 570                 575

Gly Leu Leu Thr Ile Ile Pro Leu Gly Asp Ala Pro Ser Ala Leu Ser
            580                 585                 590

Arg Ile Thr Gln Val Gln Leu Gln Arg Asp Glu Asp Ile His Ser Lys
        595                 600                 605

Cys Pro Ser Ser Ser Cys Glu Leu Trp Ala Thr Leu Ser Trp Met Met
    610                 615                 620

Glu His Asn Ser Lys Glu Asp Trp Asp Gln Val Asp His Tyr Met Ile
625                 630                 635                 640

Phe Phe Lys Asn Val Asp Ser Lys Ala Glu Pro Ile Phe Leu Gly Thr
                645                 650                 655

Ser Phe Ser Thr Glu Tyr Arg Ile Ser Gly Leu Glu Ile Lys Lys His
            660                 665                 670

Gly Asn Ser Ile Glu Ile Trp Ala Val Asn Arg Leu Gly Thr Val Ile
        675                 680                 685

Ala Arg Gln Asp Ile Asp Ile Gln
    690                 695

<210> SEQ ID NO 2
```

```
<211> LENGTH: 696
<212> TYPE: PRT
<213> ORGANISM: Rhizomucor pusillus

<400> SEQUENCE: 2

Met Pro Ser Leu Glu Leu Gln Gln Ala Ala Asp Thr Arg Leu Phe Glu
1               5                   10                  15

Ser Met Pro Leu Gln Thr Met Asn Glu Leu Gly Ser Trp Glu Pro Ser
            20                  25                  30

Asn Ala Ser Arg Ala Asn Ile Ala Thr Ile Pro Leu His Gln Arg Ser
        35                  40                  45

Asn Leu Asp Pro Ala Glu Pro Arg Leu Ile Val Thr His Asp Met Ala
    50                  55                  60

Gly Gly Tyr Lys Glu Asp Ser Asn Ile Gln Gly Asn Thr Tyr Asp Thr
65                  70                  75                  80

Ile Tyr Ser Cys Gln Tyr Trp Gln Tyr Val Asp Thr Phe Ile Tyr Phe
                85                  90                  95

Ser His His Arg Val Thr Ile Pro Pro Val Asn Trp Ile Asn Ala Cys
            100                 105                 110

His Arg Asn Gly Val Lys Thr Leu Gly Thr Phe Ile Val Glu Gly Thr
        115                 120                 125

Ala Gly Met Phe Ala Leu Glu Arg Phe Val Tyr Gly Pro Glu Pro Gly
    130                 135                 140

Gln Arg Asn Ser Trp Ser Pro Tyr Tyr Ala Asp Lys Leu Val Asp Ile
145                 150                 155                 160

Ala Glu Phe Tyr Gly Phe Asp Gly Trp Leu Leu Asn Ile Glu Ser Asp
                165                 170                 175

Phe Phe Pro Leu Tyr Arg Asn Pro Ser Leu Lys Ala Ile His Leu Ala
            180                 185                 190

Lys Leu Leu Arg Tyr Leu Lys Asn Ala Met His Ala Arg Val Pro Gly
        195                 200                 205

Ser Glu Ile Ile Trp Tyr Asp Ser Met Thr Thr Asn Gly Ser Val Gln
    210                 215                 220

Trp Gln Asn Asn Ile Thr Pro Lys Asn Ser Ile Phe Phe Glu Ala Ala
225                 230                 235                 240

Asp Gly Ile Phe Leu Asn Tyr Trp Trp Asn Ala Thr Val Pro Pro Leu
                245                 250                 255

Ala Leu Gln Val Ala His Arg Leu Gly Arg Gln Gly Ser Asp Val Tyr
            260                 265                 270

Phe Gly Thr Asp Val Trp Gly Arg Gly Thr Phe Gly Gly Gly Gly Phe
        275                 280                 285

Asp Ser Tyr Leu Ala Val Gly Thr Ala Arg Ala Phe Lys Thr Ser Ser
    290                 295                 300

Ala Leu Phe Gly Thr Ala Trp Ile Tyr Glu His Phe Gly Lys Lys Asp
305                 310                 315                 320

Phe Glu Leu Met Asp Arg Leu Leu Trp Leu Gly Gly Asp Gln Ser Glu
                325                 330                 335

Tyr Pro Ala Gln Glu Gly Glu Gln Asn Arg Thr Val Lys Val Thr Ser
            340                 345                 350

His Leu Gly Arg His Pro Gly Ile Ala Asp Val Ser Pro Val Arg Ser
        355                 360                 365

Ala Pro Gly Lys Thr Trp Phe Ala Thr Trp Phe Asp Arg Gly Tyr Gly
    370                 375                 380

Thr Gly Phe Tyr Tyr Gln Gly Lys Lys Leu Leu Ser Gln Pro Trp Ser
```

```
385                 390                 395                 400

His Leu Ser His Gln Ser Ile Pro Pro Asn Leu Ile Ala Arg Leu Gln
                405                 410                 415

Arg Glu Glu Asn His Gly Leu Ser Tyr Phe Leu Ala Asp Asp Asp Ala
            420                 425                 430

Tyr Ile Gly Gly Thr Ser Leu Leu Ile Ala Ala Glu Ile Thr Gln Glu
        435                 440                 445

Arg Gln Leu Pro Leu Tyr Gln Leu Glu Tyr Asp Val Thr Glu Gly Cys
    450                 455                 460

Glu Val Gln Phe Ile Tyr Lys Ser Pro Glu Pro Asp Met Gln Gly Lys
465                 470                 475                 480

Ile Asp Ile Tyr Leu Asn Leu Gln Val Thr Asp Ile Leu Pro Asp Glu
                485                 490                 495

Leu Ala Phe Tyr Trp Gln Asp Val Thr Asp Ala Ser Ser Gln Ala Asp
            500                 505                 510

Ala Thr Thr Ala Met Arg Leu Tyr Leu Asn Glu Asn Thr Val Ile Tyr
        515                 520                 525

Leu Lys Pro Ser Arg Lys Gln Glu Leu Ala Glu Gly Trp Leu Leu Cys
    530                 535                 540

Ser Val Arg Val Pro Pro Thr Tyr Pro Leu Gly Ile Ala Thr Ile Lys
545                 550                 555                 560

Glu Leu Gly Ile His Val Asp Gly Thr Glu Thr Val Leu Phe Arg Leu
                565                 570                 575

Gly Leu Leu Thr Ile Ile Pro Leu Gly Asp Ala Pro Ser Ala Leu Ser
            580                 585                 590

Arg Ile Thr Gln Val Gln Leu Gln Arg Asp Glu Asp Ile His Ser Lys
        595                 600                 605

Cys Pro Ser Ser Ser Cys Glu Leu Trp Ala Thr Leu Ser Trp Met Met
    610                 615                 620

Glu His Asn Ser Lys Glu Asp Trp Asp Gln Val Asp His Tyr Met Ile
625                 630                 635                 640

Phe Phe Lys Asn Val Asp Ser Lys Ala Glu Pro Ile Phe Leu Gly Thr
                645                 650                 655

Ser Phe Ser Thr Glu Tyr Arg Ile Ser Gly Leu Glu Ile Lys Lys His
            660                 665                 670

Gly Asn Ser Ile Glu Ile Trp Ala Val Asn Arg Leu Gly Thr Val Ile
        675                 680                 685

Ala Arg Gln Asp Ile Asp Ile Gln
    690                 695


<210> SEQ ID NO 3
<211> LENGTH: 696
<212> TYPE: PRT
<213> ORGANISM: Rhizomucor pusillus

<400> SEQUENCE: 3

Met Pro Ser Leu Glu Leu Gln Gln Ala Ala Asp Thr Arg Leu Phe Glu
1               5                   10                  15

Ser Met Pro Leu Gln Thr Met Asn Glu Leu Gly Ser Trp Glu Pro Ser
            20                  25                  30

Asn Ala Ser Arg Ala Asn Ile Ala Thr Ile Pro Leu His Gln Arg Ser
        35                  40                  45

Asn Leu Asp Pro Ala Glu Pro Arg Leu Ile Val Thr His Asp Met Ala
    50                  55                  60
```

```
Gly Gly Tyr Lys Glu Asp Ser Asn Ile Gln Gly Asn Thr Tyr Asp Thr
65                  70                  75                  80

Ile Tyr Ser Cys Gln Tyr Trp Gln Tyr Val Asp Thr Phe Ile Tyr Phe
                85                  90                  95

Ser His His Arg Val Thr Ile Pro Pro Val Asn Trp Ile Asn Ala Cys
            100                 105                 110

His Arg Asn Gly Val Lys Thr Leu Gly Thr Phe Ile Val Glu Gly Ala
        115                 120                 125

Ala Gly Met Phe Ala Leu Glu Arg Phe Val Tyr Gly Pro Glu Pro Gly
    130                 135                 140

Gln Arg Asn Ser Trp Ser Pro Tyr Tyr Ala Asp Lys Leu Val Asp Ile
145                 150                 155                 160

Ala Glu Phe Tyr Gly Phe Asp Gly Trp Leu Leu Asn Ile Glu Ser Asp
                165                 170                 175

Phe Phe Pro Leu Tyr Arg Asn Pro Ser Leu Lys Ala Ile His Leu Ala
            180                 185                 190

Lys Leu Leu Arg Tyr Leu Lys Asn Ala Met His Ala Arg Val Pro Gly
        195                 200                 205

Ser Glu Ile Ile Trp Tyr Asp Ser Met Thr Thr Asn Gly Ser Val Gln
    210                 215                 220

Trp Gln Asn Asn Ile Thr Pro Lys Asn Ser Ile Phe Phe Glu Ala Ala
225                 230                 235                 240

Asp Gly Ile Phe Leu Asn Tyr Trp Trp Asn Ala Thr Val Pro Pro Leu
                245                 250                 255

Ala Leu Gln Val Ala His Arg Leu Gly Arg Gln Gly Ser Asp Val Tyr
            260                 265                 270

Phe Gly Thr Asp Val Trp Gly Arg Gly Thr Phe Gly Gly Gly Gly Phe
        275                 280                 285

Asp Ser Tyr Leu Ala Val Gly Thr Ala Arg Ala Phe Lys Thr Ser Ser
    290                 295                 300

Ala Leu Phe Gly Thr Ala Trp Ile Tyr Glu His Phe Gly Lys Lys Asp
305                 310                 315                 320

Phe Glu Leu Met Asp Arg Leu Leu Trp Leu Gly Gly Gly Gln Ser Glu
                325                 330                 335

Tyr Pro Ala Gln Glu Gly Glu Gln Asn Arg Thr Val Lys Val Thr Ser
            340                 345                 350

His Leu Gly Arg His Pro Gly Ile Ala Asp Val Ser Pro Val Arg Ser
        355                 360                 365

Ala Pro Gly Lys Thr Trp Phe Ala Thr Trp Phe Asp Arg Gly Tyr Gly
    370                 375                 380

Thr Gly Phe Tyr Tyr Gln Gly Lys Lys Leu Leu Ser Gln Pro Trp Ser
385                 390                 395                 400

His Leu Ser His Gln Ser Ile Pro Pro Asn Leu Ile Ala Arg Leu Gln
                405                 410                 415

Arg Glu Glu Asn His Gly Leu Ser Tyr Phe Leu Ala Asp Asp Asp Ala
            420                 425                 430

Tyr Leu Gly Gly Thr Ser Leu Leu Ile Ala Ala Glu Ile Thr Gln Glu
        435                 440                 445

Arg Gln Leu Pro Leu Tyr Gln Leu Glu Tyr Asp Val Thr Glu Gly Cys
    450                 455                 460

Glu Val Gln Phe Ile Tyr Lys Ser Pro Glu Pro Asp Met Gln Gly Lys
465                 470                 475                 480

Ile Asp Ile Tyr Leu Asn Leu Gln Val Thr Asp Ile Leu Pro Asp Glu
```

```
                485                 490                 495

Leu Ala Phe Tyr Trp Gln Asp Val Thr Asp Ala Ser Ser Gln Ala Asp
            500                 505                 510

Ala Thr Thr Ala Met Arg Leu Tyr Leu Asn Glu Asn Thr Val Val Tyr
        515                 520                 525

Leu Lys Pro Ser Arg Lys Gln Glu Leu Ala Glu Gly Trp Leu Leu Cys
    530                 535                 540

Ser Val Arg Val Pro Pro Thr Tyr Pro Leu Gly Ile Ala Thr Ile Lys
545                 550                 555                 560

Glu Leu Gly Ile His Val Asp Gly Thr Glu Thr Val Leu Phe Arg Leu
                565                 570                 575

Gly Leu Leu Thr Ile Ile Pro Leu Gly Asp Ala Pro Ser Ala Leu Ser
            580                 585                 590

Arg Ile Thr Gln Val Gln Leu Gln Arg Asp Glu Asp Ile His Ser Lys
        595                 600                 605

Cys Ser Ser Ser Ser Cys Glu Leu Trp Ala Thr Leu Ser Trp Met Met
    610                 615                 620

Glu Arg Asn Ser Lys Glu Asp Trp Asp Gln Val Asp His Tyr Met Ile
625                 630                 635                 640

Phe Phe Lys Asn Val Asp Ser Lys Ala Glu Pro Ile Phe Leu Gly Thr
                645                 650                 655

Ser Phe Ser Thr Glu Tyr Arg Ile Ser Gly Leu Glu Ile Lys Lys His
            660                 665                 670

Gly Asn Ser Ile Glu Ile Trp Ala Val Asn Arg Leu Gly Thr Val Ile
        675                 680                 685

Ala Arg Gln Asp Ile Asp Ile Gln
    690                 695


<210> SEQ ID NO 4
<211> LENGTH: 696
<212> TYPE: PRT
<213> ORGANISM: Rhizomucor pusillus

<400> SEQUENCE: 4

Met Pro Ser Leu Glu Leu Gln Gln Ala Ala Asp Thr Arg Leu Phe Glu
1               5                   10                  15

Ser Met Pro Leu Gln Thr Met Asn Glu Leu Gly Ser Trp Glu Pro Ser
            20                  25                  30

Asn Ala Ser Arg Ala Asn Ile Ala Thr Ile Pro Leu His Gln Arg Ser
        35                  40                  45

Asn Leu Asp Pro Ala Glu Pro Arg Leu Ile Val Thr His Asp Met Ala
    50                  55                  60

Gly Gly Tyr Lys Glu Asp Ser Asn Ile Gln Gly Asn Thr Tyr Asp Thr
65                  70                  75                  80

Ile Tyr Ser Cys Gln Tyr Trp Gln Tyr Val Asp Thr Phe Ile Tyr Phe
                85                  90                  95

Ser His His Arg Val Thr Ile Pro Pro Val Asn Trp Ile Asn Ala Cys
            100                 105                 110

His Arg Asn Gly Val Lys Thr Leu Gly Thr Phe Ile Val Glu Gly Ala
        115                 120                 125

Ala Gly Met Phe Ala Leu Glu Arg Phe Val Tyr Gly Pro Glu Pro Gly
    130                 135                 140

Gln Arg Asn Ser Trp Ser Pro Tyr Tyr Ala Asp Lys Leu Val Asp Ile
145                 150                 155                 160
```

```
Ala Glu Phe Tyr Gly Phe Asp Gly Trp Leu Leu Asn Ile Glu Ser Asp
                165                 170                 175

Phe Phe Pro Leu Tyr Arg Asn Pro Ser Leu Lys Ala Ile His Leu Ala
            180                 185                 190

Lys Leu Leu Arg Tyr Leu Lys Asn Ala Met His Ala Arg Val Pro Gly
        195                 200                 205

Ser Glu Ile Ile Trp Tyr Asp Ser Met Thr Thr Asn Gly Ser Val Gln
    210                 215                 220

Trp Gln Asn Asn Ile Thr Pro Lys Asn Ser Ile Phe Phe Glu Ala Ala
225                 230                 235                 240

Asp Gly Ile Phe Leu Asn Tyr Trp Trp Asn Ala Thr Val Pro Pro Leu
                245                 250                 255

Ala Leu Gln Val Ala His Arg Leu Gly Arg Gln Gly Ser Asp Val Tyr
            260                 265                 270

Phe Gly Thr Asp Val Trp Gly Arg Gly Thr Phe Gly Gly Gly Gly Phe
        275                 280                 285

Asp Ser Tyr Leu Ala Val Gly Thr Ala Arg Ala Phe Lys Thr Ser Ser
    290                 295                 300

Ala Leu Phe Gly Thr Ala Trp Ile Tyr Glu His Phe Gly Lys Lys Asp
305                 310                 315                 320

Phe Glu Leu Met Asp Arg Leu Leu Trp Leu Gly Gly Asp Gln Ser Glu
                325                 330                 335

Tyr Pro Ala Gln Glu Gly Glu Gln Asn Arg Thr Val Lys Val Thr Ser
            340                 345                 350

His Leu Gly Arg His Pro Gly Ile Ala Asp Val Ser Pro Val Arg Ser
        355                 360                 365

Ala Pro Gly Lys Thr Trp Phe Ala Thr Trp Phe Asp Arg Gly Tyr Gly
    370                 375                 380

Thr Gly Phe Tyr Tyr Gln Gly Lys Lys Leu Leu Ser Gln Pro Trp Ser
385                 390                 395                 400

His Leu Ser His Gln Ser Ile Pro Pro Asn Leu Ile Ala Arg Leu Gln
                405                 410                 415

Arg Glu Glu Asn His Gly Leu Ser Tyr Phe Leu Ala Asp Asp Asp Ala
            420                 425                 430

Tyr Ile Gly Gly Thr Ser Leu Leu Ile Ala Ala Glu Ile Thr Gln Glu
        435                 440                 445

Arg Gln Leu Pro Leu Tyr Gln Leu Glu Tyr Asp Ala Thr Glu Gly Cys
    450                 455                 460

Glu Val Gln Phe Ile Tyr Lys Ser Pro Glu Pro Asp Met Gln Gly Lys
465                 470                 475                 480

Ile Asp Ile Tyr Leu Asn Leu Gln Val Thr Asp Ile Leu Pro Asp Glu
                485                 490                 495

Leu Ala Phe Tyr Trp Gln Asp Val Thr Asp Ala Ser Ser Gln Ala Asp
            500                 505                 510

Ala Thr Thr Ala Met Arg Leu Tyr Leu Asn Glu Asn Thr Val Ile Tyr
        515                 520                 525

Leu Lys Pro Ser Arg Lys Gln Glu Leu Ala Glu Gly Trp Leu Leu Cys
    530                 535                 540

Ser Val Arg Val Pro Pro Thr Tyr Pro Leu Gly Ile Ala Thr Ile Lys
545                 550                 555                 560

Glu Leu Gly Ile His Val Asp Gly Thr Glu Thr Val Leu Phe Arg Leu
                565                 570                 575

Gly Leu Leu Thr Ile Ile Pro Leu Gly Asp Ala Pro Ser Ala Leu Ser
```

```
            580                 585                 590

Arg Ile Thr Gln Val Gln Leu Gln Arg Asp Glu Asp Ile His Ser Lys
        595                 600                 605

Cys Pro Ser Ser Ser Cys Glu Leu Trp Ala Thr Leu Ser Trp Met Met
    610                 615                 620

Glu His Asn Ser Lys Glu Asp Trp Asp Gln Val Asp His Tyr Met Ile
625                 630                 635                 640

Phe Phe Lys Asn Val Asp Ser Lys Ala Glu Pro Ile Phe Leu Gly Thr
                645                 650                 655

Ser Phe Ser Thr Glu Tyr Arg Ile Ser Gly Leu Glu Ile Lys Lys His
            660                 665                 670

Gly Asn Ser Ile Glu Ile Trp Ala Val Asn Arg Leu Gly Thr Val Ile
        675                 680                 685

Ala Arg Gln Asp Ile Asp Ile Gln
    690                 695


<210> SEQ ID NO 5
<211> LENGTH: 696
<212> TYPE: PRT
<213> ORGANISM: Rhizomucor pusillus

<400> SEQUENCE: 5

Met Pro Ser Leu Glu Leu Gln Gln Ala Ala Asp Thr Arg Leu Phe Glu
1               5                   10                  15

Ser Met Pro Leu Gln Thr Met Asn Glu Leu Gly Ser Trp Glu Pro Ser
            20                  25                  30

Asn Ala Ser Arg Ala Asn Ile Ala Thr Ile Pro Leu His Gln Arg Ser
        35                  40                  45

Asn Leu Asp Pro Ala Glu Pro Arg Leu Ile Val Thr His Asp Met Ala
    50                  55                  60

Gly Gly Tyr Lys Glu Asp Ser Asn Ile Gln Gly Asn Thr Tyr Asp Thr
65                  70                  75                  80

Ile Tyr Ser Cys Gln Tyr Trp Gln Tyr Val Asp Thr Phe Ile Tyr Phe
                85                  90                  95

Ser His His Arg Val Thr Ile Pro Pro Val Asn Trp Ile Asn Ala Cys
            100                 105                 110

His Arg Asn Gly Val Lys Thr Leu Gly Thr Phe Ile Val Glu Gly Ala
        115                 120                 125

Ala Gly Met Phe Ala Leu Glu Arg Phe Val Tyr Gly Pro Glu Pro Gly
    130                 135                 140

Gln Arg Asn Ser Trp Ser Pro Tyr Tyr Ala Asp Lys Leu Val Asp Ile
145                 150                 155                 160

Ala Glu Phe Tyr Gly Phe Asp Gly Trp Leu Leu Asn Ile Glu Ser Asp
                165                 170                 175

Phe Phe Pro Leu Tyr Arg Asn Pro Ser Leu Lys Ala Ile His Leu Ala
            180                 185                 190

Lys Leu Leu Arg Tyr Leu Lys Asn Ala Met His Ala Arg Val Pro Gly
        195                 200                 205

Ser Glu Ile Ile Trp Tyr Asp Ser Met Thr Thr Asn Gly Ser Val Gln
    210                 215                 220

Trp Gln Asn Asn Ile Thr Pro Lys Asn Ser Ile Phe Phe Glu Ala Ala
225                 230                 235                 240

Asp Gly Ile Phe Leu Asn Tyr Trp Trp Asn Ala Thr Val Pro Pro Leu
                245                 250                 255
```

```
Ala Leu Gln Val Ala His Arg Leu Gly Arg Gln Gly Ser Asp Val Tyr
            260                 265                 270

Phe Gly Thr Asp Val Trp Gly Arg Gly Thr Phe Gly Gly Gly Gly Phe
        275                 280                 285

Asp Ser Tyr Leu Ala Val Gly Thr Ala Arg Ala Phe Lys Thr Ser Ser
    290                 295                 300

Ala Leu Phe Gly Thr Ala Trp Ile Tyr Glu His Phe Gly Lys Lys Asp
305                 310                 315                 320

Phe Glu Leu Met Asp Arg Leu Leu Trp Leu Gly Gly Asp Gln Ser Glu
                325                 330                 335

Tyr Pro Ala Gln Glu Gly Glu Gln Asn Arg Thr Val Lys Val Thr Ser
            340                 345                 350

His Leu Gly Arg His Pro Gly Ile Ala Asp Val Ser Pro Val Arg Ser
        355                 360                 365

Ala Pro Gly Lys Thr Trp Phe Ala Thr Trp Phe Asp Arg Gly Tyr Gly
    370                 375                 380

Thr Gly Phe Tyr Tyr Gln Gly Lys Lys Leu Leu Ser Gln Pro Trp Ser
385                 390                 395                 400

His Leu Ser His Gln Ser Ile Pro Pro Asn Leu Ile Ala Arg Leu Gln
                405                 410                 415

Arg Glu Glu Asn His Gly Leu Ser Tyr Phe Leu Ala Asp Asp Asp Ala
            420                 425                 430

Tyr Ile Gly Gly Thr Ser Leu Leu Ile Ala Ala Glu Ile Thr Gln Glu
        435                 440                 445

Arg Gln Leu Pro Leu Tyr Gln Leu Glu Tyr Asp Val Thr Glu Gly Cys
    450                 455                 460

Glu Val Gln Phe Ile Tyr Lys Ser Pro Glu Pro Asp Met Gln Gly Lys
465                 470                 475                 480

Ile Asp Ile Tyr Leu Asn Leu Gln Val Thr Asp Ile Leu Pro Asp Glu
                485                 490                 495

Leu Ala Phe Tyr Trp Gln Asp Val Thr Asp Ala Ser Ser Gln Ala Asp
            500                 505                 510

Ala Thr Thr Ala Met Arg Leu Tyr Leu Asn Glu Asn Thr Val Ile Tyr
        515                 520                 525

Leu Lys Pro Ser Arg Lys Gln Glu Leu Ala Glu Gly Trp Leu Leu Cys
    530                 535                 540

Ser Val Arg Val Pro Pro Thr Tyr Pro Leu Gly Ile Ala Thr Ile Lys
545                 550                 555                 560

Glu Leu Gly Ile His Val Asp Gly Thr Glu Thr Val Leu Phe Arg Leu
                565                 570                 575

Gly Leu Leu Thr Ile Ile Pro Leu Gly Asp Ala Pro Ser Ala Leu Ser
            580                 585                 590

Arg Ile Thr Gln Val Gln Leu Gln Arg Asp Glu Asp Ile His Ser Lys
        595                 600                 605

Cys Pro Ser Ser Ser Cys Glu Leu Trp Ala Thr Leu Ser Trp Met Met
    610                 615                 620

Glu His Asn Ser Lys Glu Asp Trp Asp Gln Val Asp His Tyr Met Ile
625                 630                 635                 640

Phe Phe Lys Asn Val Asp Ser Lys Ala Glu Pro Ile Phe Leu Gly Thr
                645                 650                 655

Ser Phe Ser Thr Glu Tyr Arg Ile Ser Gly Leu Glu Ile Lys Lys His
            660                 665                 670

Gly Asn Ser Ile Glu Ile Trp Ala Val Asn Arg Leu Gly Thr Val Ile
```

```
        675                 680                 685

Ala Arg Gln Asp Ile Asp Ile Gln
    690                 695


<210> SEQ ID NO 6
<211> LENGTH: 697
<212> TYPE: PRT
<213> ORGANISM: Rhizomucor miehei

<400> SEQUENCE: 6

Met Pro Ser Leu Glu Leu Gln Gln Ala Val Asp Thr Arg Leu Phe Glu
1               5                   10                  15

Ser Thr Pro Leu Met Thr Met Asp Glu Leu Gly Ser Trp Asp Pro Ser
            20                  25                  30

Asn Ala Leu Arg Ala Ser Ile Ala Thr Val Pro Leu His Pro Arg Pro
        35                  40                  45

Ser Ile Asp Pro Thr Glu Pro Arg Leu Ile Val Thr His Asp Met Ala
    50                  55                  60

Gly Gly Tyr Lys Glu Asp Phe Ser Ile Gln Gly Asn Ala Tyr Asp Thr
65                  70                  75                  80

Val Tyr Thr Cys Gln Tyr Trp Gln Tyr Val Asp Ile Phe Ile Tyr Phe
                85                  90                  95

Ser His His Arg Val Thr Ile Pro Pro Val Asn Trp Thr Asn Ala Cys
            100                 105                 110

His Arg Asn Gly Val Lys Ser Leu Gly Thr Phe Ile Val Glu Gly Ala
        115                 120                 125

Ala Gly Met Phe Ala Leu Glu Arg Phe Val Tyr Gly Pro Asn Pro Gly
    130                 135                 140

Gln Arg Lys Ser Trp Ser Pro Tyr Tyr Ala Asp Lys Leu Val Asp Ile
145                 150                 155                 160

Ala Glu Phe Tyr Gly Phe Asp Gly Trp Leu Ile Asn Ile Glu Ser Asp
                165                 170                 175

Phe Phe Pro Leu Tyr Arg Ser Pro Ser Met Lys Ala Lys His Leu Ala
            180                 185                 190

Lys Leu Leu Leu Tyr Leu Arg Asn Ala Met His Ala Arg Val Pro Gly
        195                 200                 205

Ser Gln Ile Ile Trp Tyr Asp Ser Met Thr Thr Ser Gly Tyr Val Gln
    210                 215                 220

Trp Gln Asn Asn Ile Thr Pro Gln Asn Glu Ile Phe Phe Glu Ala Ala
225                 230                 235                 240

Asp Gly Ile Phe Leu Asn Tyr Trp Trp Asn Ala Thr Tyr Pro Pro Phe
                245                 250                 255

Ala Met Gln Val Ala His Tyr Leu Gly Arg Gln Gly Ser Asp Val Tyr
            260                 265                 270

Phe Gly Ser Asp Ile Trp Gly Arg Gly Thr Phe Gly Gly Gly Gly Phe
        275                 280                 285

Asp Ser Tyr Leu Ala Val Ala Thr Ala Ser Ala Phe Lys Thr Ser Ser
    290                 295                 300

Ala Leu Phe Gly Thr Ala Trp Thr Tyr Glu His Phe Glu Lys Lys Asp
305                 310                 315                 320

Phe Glu Leu Met Asp Arg Leu Leu Trp Leu Gly Gly Asp Gln Ser Glu
                325                 330                 335

Tyr Pro Ala Gln Ala Glu Gly Gln Glu Ser Ile Ala Lys Ser Gly Ser
            340                 345                 350
```

```
Arg Leu Gly Arg His Pro Gly Ile Thr Asp Val Ala Ala Val Arg Ser
        355                 360                 365

Ala Pro Gly Arg Arg Trp Phe Val Thr Trp Phe Asp Arg Gly His Gly
    370                 375                 380

Thr Gly Phe Tyr His Gln Gly Lys Lys Leu Leu Ser Gln Pro Trp Ser
385                 390                 395                 400

His Leu Ser His Gln Ser Ile Pro Pro Asn Leu Val Ala Arg Leu Gln
                405                 410                 415

Arg Lys Glu Asp Asp Gly Val Ser Tyr Phe Leu Ala Asp Asp Asp Ala
            420                 425                 430

Tyr Ile Gly Gly Thr Ser Leu Leu Ile Ala Ala Glu Gly Thr Gln Glu
        435                 440                 445

Arg Gln Ile Pro Leu Tyr Gln Leu Asn Tyr Asp Ala Thr Asn Gly Cys
    450                 455                 460

Glu Val Gln Phe Val Tyr Lys Ser Pro Glu Pro Asp Met Gln Ser Lys
465                 470                 475                 480

Val Gln Ile Tyr Leu Asn Leu Arg Val Thr Asp Val Leu Pro Asp Glu
                485                 490                 495

Leu Ala Tyr Tyr Trp His Asp Val Ala Ala Thr Ser Pro Gln Pro Gln
            500                 505                 510

Ala Thr Thr Ala Ser Arg Leu Asn Ile Asn Glu Asp Thr Ser Val Tyr
        515                 520                 525

Leu Asn Thr Ser Lys Thr Gln Glu Leu Ala Glu Gly Trp Val Leu Cys
    530                 535                 540

Ser Val Arg Val Pro Ser Val His Pro Leu Gly Glu Ala Ala Ile Glu
545                 550                 555                 560

Glu Leu Gly Ile Tyr Leu Asp Gly Thr Glu Asp Val Leu Phe Arg Leu
                565                 570                 575

Gly Leu Leu Thr Ile Val Pro Tyr Thr Asp Thr Ser Ser Thr Leu Ala
            580                 585                 590

Ser Lys Ile Thr His Ile Gln Leu Gln Arg Asp Ala Asp Val Ser Ser
        595                 600                 605

Lys Cys Leu Ser Ser Ser Cys Glu Leu Trp Ala Thr Leu Ser Trp Met
    610                 615                 620

Met Glu Ser Asn Ser Ser Glu Glu Trp Asn Gln Val Asp His Tyr Leu
625                 630                 635                 640

Ile Ser Tyr Gly Asp Ile Asn Ala Asp Gly Ala Ala Thr Phe Leu Gly
                645                 650                 655

Thr Thr Phe Thr Thr Glu Tyr Arg Ile Ser Gly Leu Glu Met Lys Asn
            660                 665                 670

Asp Ile Asp Tyr Ile Gln Ile Ser Ala Val Ser Arg Leu Gly Asn Ile
        675                 680                 685

Leu Ala Gln Gln Thr Ile Gly Ile Gln
    690                 695
```

<210> SEQ ID NO 7
<211> LENGTH: 701
<212> TYPE: PRT
<213> ORGANISM: Artificial Sequence
<220> FEATURE:
<223> OTHER INFORMATION: The assumed amino acid sequence derived from publicly available genomic DNA sequence of Rhizomucor pusillus strain CBS 183.67, which has been assumed to be endo-beta-N-acetylglucosaminidase.

<400> SEQUENCE: 7

```
Met Pro Ser Leu Glu Leu Gln Gln Ala Ala Asp Thr Arg Leu Phe Glu
1               5                   10                  15

Ser Met Pro Leu Gln Thr Met Asn Glu Leu Gly Ser Trp Glu Pro Ser
            20                  25                  30

Asn Ala Ser Arg Ala Asn Ile Ala Thr Ile Pro Leu His Gln Arg Ser
        35                  40                  45

Asn Leu Asp Pro Ala Glu Pro Arg Leu Ile Val Thr His Asp Met Ala
    50                  55                  60

Gly Gly Tyr Lys Glu Asp Ser Asn Ile Gln Gly Asn Thr Tyr Asp Thr
65                  70                  75                  80

Ile Tyr Ser Cys Gln Tyr Trp Gln Tyr Val Asp Thr Phe Ile Tyr Phe
                85                  90                  95

Ser His His Arg Val Thr Ile Pro Pro Val Asn Trp Ile Asn Ala Cys
            100                 105                 110

His Arg Asn Gly Val Lys Thr Leu Gly Thr Phe Ile Val Glu Gly Ala
        115                 120                 125

Ala Gly Met Phe Ala Leu Glu Arg Phe Val Tyr Gly Pro Glu Pro Gly
    130                 135                 140

Gln Arg Asn Ser Trp Ser Pro Tyr Tyr Ala Asp Lys Leu Val Asp Ile
145                 150                 155                 160

Ala Glu Phe Tyr Gly Phe Asp Gly Trp Leu Leu Asn Ile Glu Ser Asp
                165                 170                 175

Phe Phe Pro Leu Tyr Arg Asn Pro Ser Leu Lys Ala Ile His Leu Ala
            180                 185                 190

Asn Thr Tyr Tyr Ile Arg Leu Leu Arg Tyr Leu Lys Asn Ala Met His
        195                 200                 205

Ala Arg Val Pro Gly Ser Glu Ile Ile Trp Tyr Asp Ser Met Thr Thr
    210                 215                 220

Asn Gly Ser Val Gln Trp Gln Asn Asn Ile Thr Pro Lys Asn Ser Ile
225                 230                 235                 240

Phe Phe Glu Ala Ala Asp Gly Ile Phe Leu Asn Tyr Trp Trp Asn Ala
                245                 250                 255

Thr Val Pro Pro Leu Ala Leu Gln Val Ala His Arg Leu Gly Arg Gln
            260                 265                 270

Gly Ser Asp Val Tyr Phe Gly Thr Asp Val Trp Gly Arg Gly Thr Phe
        275                 280                 285

Gly Gly Gly Gly Phe Asp Ser Tyr Leu Ala Val Gly Thr Ala Arg Ala
    290                 295                 300

Phe Lys Thr Ser Ser Ala Leu Phe Gly Thr Ala Trp Ile Tyr Glu His
305                 310                 315                 320

Phe Gly Lys Lys Asp Phe Glu Leu Met Asp Arg Leu Leu Trp Leu Gly
                325                 330                 335

Gly Asp Gln Ser Glu Tyr Pro Ala Gln Glu Gly Glu Gln Asn Arg Thr
            340                 345                 350

Val Lys Val Thr Ser His Leu Gly Arg His Pro Gly Ile Ala Asp Val
        355                 360                 365

Ser Pro Val Arg Ser Ala Pro Gly Lys Thr Trp Phe Ala Thr Trp Phe
    370                 375                 380

Asp Arg Gly Tyr Gly Thr Gly Phe Tyr Tyr Gln Gly Lys Lys Leu Leu
385                 390                 395                 400

Ser Gln Pro Trp Ser His Leu Ser His Gln Ser Ile Pro Pro Asn Leu
                405                 410                 415

Ile Ala Arg Leu Gln Arg Glu Glu Asn His Gly Leu Ser Tyr Phe Leu
```

```
            420                 425                 430

Ala Asp Asp Asp Ala Tyr Ile Gly Gly Thr Ser Leu Leu Ile Ala Ala
        435                 440                 445

Glu Ile Thr Gln Glu Arg Gln Leu Pro Leu Tyr Gln Leu Glu Tyr Asp
    450                 455                 460

Val Thr Glu Gly Cys Glu Val Gln Phe Ile Tyr Lys Ser Pro Glu Pro
465                 470                 475                 480

Asp Met Gln Gly Lys Ile Asp Ile Tyr Leu Asn Leu Gln Val Thr Asp
                485                 490                 495

Ile Leu Pro Asp Glu Leu Ala Phe Tyr Trp Gln Asp Val Thr Asp Ala
            500                 505                 510

Ser Ser Gln Ala Asp Ala Thr Thr Ala Met Arg Leu Tyr Leu Asn Glu
        515                 520                 525

Asn Thr Val Ile Tyr Leu Lys Pro Ser Arg Lys Gln Glu Leu Ala Glu
    530                 535                 540

Gly Trp Leu Leu Cys Ser Val Arg Val Pro Pro Thr Tyr Pro Leu Gly
545                 550                 555                 560

Ile Ala Thr Ile Lys Glu Leu Gly Ile His Val Asp Gly Thr Glu Thr
                565                 570                 575

Val Leu Phe Arg Leu Gly Leu Leu Thr Ile Ile Pro Leu Gly Asp Ala
            580                 585                 590

Pro Ser Ala Leu Ser Arg Ile Thr Gln Val Gln Leu Gln Arg Asp Glu
        595                 600                 605

Asp Ile His Ser Lys Cys Pro Ser Ser Ser Cys Glu Leu Trp Ala Thr
    610                 615                 620

Leu Ser Trp Met Met Glu His Asn Ser Lys Glu Asp Trp Asp Gln Val
625                 630                 635                 640

Asp His Tyr Met Ile Phe Phe Lys Asn Val Asp Ser Lys Ala Glu Pro
                645                 650                 655

Ile Phe Leu Gly Thr Ser Phe Ser Thr Glu Tyr Arg Ile Ser Gly Leu
            660                 665                 670

Glu Ile Lys Lys His Gly Asn Ser Ile Glu Ile Trp Ala Val Asn Arg
        675                 680                 685

Leu Gly Thr Val Ile Ala Arg Gln Asp Ile Asp Ile Gln
    690                 695                 700
```

<210> SEQ ID NO 8
<211> LENGTH: 2091
<212> TYPE: DNA
<213> ORGANISM: Rhizomucor pusillus

<400> SEQUENCE: 8

```
atgccttcac tcgaactaca gcaagctgct gacacgagac ttttcgagtc tatgccactt     60

cagactatga atgagcttgg ttcttgggaa cctagcaatg cctcgcgagc caacattgca    120

actattcctt tgcatcagcg atccaatctt gatccggcag agccgcgctt gatcgtaact    180

cacgatatgg ctggaggcta caaggaagac tcaaatattc agggcaatac gtatgataca    240

atttatagct gtcaatattg gcaatatgtg gatactttta tctatttctc gcatcatcga    300

gttacgatac ctcctgtcaa ttggataaat gcatgccaca gaaacggtgt caaaacgcta    360

ggaacattca ttgtggaagg agctgcgggc atgtttgcct tggagagatt cgtctacgga    420

cctgagcctg gacagagaaa cagctggagc ccttactatg ctgataagct ggtggacata    480

gccgagtttt acggtttcga cggctggctg cttaacattg agagtgattt cttcccttta    540
```

```
tatcgaaatc cgtctctgaa agcgatccat ctagcaaagc tgctgcgata tctgaagaat    600

gcaatgcacg ccagagtgcc aggttcagag atcatctggt atgacagcat gacgacaaac    660

ggaagtgtgc agtggcaaaa caatatcacg cccaaaaatt ccatattttt tgaagctgca    720

gatggcatat ttttaaatta ttggtggaac gcgacggttc cgccgttggc tttgcaagta    780

gcacatcgtc taggacgtca aggatctgat gtatactttg gaacggatgt ttggggacga    840

ggaacattcg gtggtggcgg attcgattca tatctcgctg ttggcactgc gagggcattc    900

aaaacatcat ctgcgctttt cggcacagca tggatctatg agcattttgg gaagaaagat    960

tttgagctta tggatagact tttgtggtta ggtggtgatc aatcagaata tccagctcag   1020

gaaggagagc agaatcgcac agtaaaagtt acatcccatc ttggaagaca tcctggtatc   1080

gccgatgtgt caccggtgcg aagtgctcca gggaaaacat ggttcgcaac gtggtttgat   1140

agaggttacg gaacaggttt ctattatcag ggcaagaaac tattatcaca gccgtggtcg   1200

catttatcgc atcaatctat cccgccgaat cttatagcca gattacagag agaagaaaat   1260

cacggccttt cgtatttcct ggcagacgac gatgcataca tcgggggaac ttcgctgtta   1320

atagcagccg aaatcactca agaacgccaa ttgccgctct atcaactaga gtatgacgtt   1380

actgaaggct gcgaggtgca gtttatatac aagtctccgg aaccagatat gcaaggaaaa   1440

atagatatat atttgaactt gcaagttaca gacatactgc ctgatgagct agccttttac   1500

tggcaagatg ttacggatgc ttcctcccag gccgatgcaa cgacagccat gcgtttatat   1560

ctaaacgaaa acacagttat ttatctaaag ccgtccagga aacaagagct agccgaaggc   1620

tggttgctct gttccgtgcg tgtgccacct acttatccac ttggtatcgc aacgatcaag   1680

gaactaggga tccatgtgga tggtaaagaa acagtgctat ttaggctggg tctccttaca   1740

attatacccc ttggagatgc gccgtctgcg ctttccagaa ttacccaggt ccagcttcaa   1800

agggatgagg atatccatag taaatgtcca tcctcctcat gcgaactttg ggccacactc   1860

tcgtggatga tggaacacaa ctcaaaagag gactgggacc aggtcgatca ctatatgatt   1920

ttcttcaaaa atgttgattc caaggcagaa cctattttcc ttggcaccag cttcagtacc   1980

gagtacagaa tatcaggcct ggagatcaag aaacacggaa attccatcga gatatgggca   2040

gtaaatcgct taggaaccgt cattgcacgg caagacatcg atatccaata g            2091
```

<210> SEQ ID NO 9
<211> LENGTH: 2109
<212> TYPE: DNA
<213> ORGANISM: Artificial Sequence
<220> FEATURE:
<223> OTHER INFORMATION: Optimized DNA sequence for expression of Endo-Rp in E. coli

<400> SEQUENCE: 9

```
atgccgagcc tggaactgca gcaggcagca gatacccgtc tgtttgaaag catgccgctg     60

cagaccatga atgaactggg tagctgggaa ccgagcaatg caagccgtgc aaatattgca    120

accattccgc tgcatcagcg tagcaatctg gatccggcag aaccgcgtct gattgttacc    180

catgatatgg caggcggtta taaagaagat agcaatattc agggcaacac ctatgatacc    240

atttatagct gtcagtattg gcagtatgtg gacaccttta tctattttag ccatcaccgt    300

gttaccattc ctccggttaa ttggattaat gcctgtcatc gtaatggtgt taaaaccctg    360

ggcaccttta ttgttgaagg tgcagcaggt atgtttgcac tggaacgttt tgtttatggt    420

ccggaaccgg gtcagcgtaa tagctggtca ccgtattatg cagataaact ggttgatatc    480
```

```
gccgagtttt atggttttga tggttggctg ctgaacatcg aaagcgattt ttttccgctg    540

tatcgtaatc cgagcctgaa agcaattcat ctggcaaaac tgctgcgcta tctgaaaaat    600

gcaatgcatg cacgtgttcc gggtagcgaa attatctggt atgatagcat gaccaccaat    660

ggtagcgttc agtggcagaa taacattacc ccgaaaaaca gcatcttttt tgaagcagcc    720

gatggcatct ttctgaatta ttggtggaat gcaaccgttc ctccgctggc actgcaggtt    780

gcacatcgtc tgggtcgtca gggtagtgat gtttattttg gcaccgatgt ttggggtcgt    840

ggcacctttg gtggtggtgg ctttgatagt tatctggcag ttggcaccgc acgtgcattt    900

aaaaccagca gcgcactgtt tggtacagca tggatttatg aacacttcgg caaaaaagac    960

ttcgaactga tggatcgtct gctgtggctg ggtggtgatc agagcgaata tccggcacaa   1020

gaaggtgaac agaatcgtac cgttaaagtt accagccatc tgggtcgcca tccgggtatt   1080

gcagatgtta gtccggttcg tagcgcaccg ggtaaaacct ggtttgcaac atggtttgat   1140

cgtggttatg gcaccggttt ctattatcag ggtaaaaaac tgctgagcca gccgtggtca   1200

catctgagcc atcagagcat tccgcctaat ctgattgcac gcctgcagcg tgaagaaaat   1260

catggcctga gctattttct ggcagatgat gatgcatata ttggtggcac cagcctgctg   1320

attgcagcag aaattaccca agaacgtcag ctgcctctgt atcagctgga atatgatgtt   1380

accgaaggtt gcgaagtgca gttcatctat aaaagccctg aaccggatat gcagggcaaa   1440

attgatatct atctgaatct gcaggttacc gatatcctgc cggatgaact ggcattttat   1500

tggcaggacg ttaccgatgc aagcagccag gcagatgcaa ccaccgcaat gcgtctgtat   1560

ctgaatgaaa ataccgtgat ttatctgaaa ccgagccgta aacaagaact ggcggaaggc   1620

tggctgctgt gtagcgttcg tgttccgcct acctatccgc tgggtattgc caccattaaa   1680

gaactgggca ttcatgtgga tggtaaagaa accgttctgt ttcgcctggg tctgctgacc   1740

attatcccgc tgggtgatgc accgagcgca ctgagccgta ttacccaggt tcagctgcaa   1800

cgtgatgaag atattcatag caaatgtccg agcagcagct gtgaactgtg ggcaaccctg   1860

agctggatga tggaacataa tagcaaagaa gattgggatc aggtcgatca ctacatgatc   1920

tttttcaaaa acgtggatag caaagccgaa ccgatttttc tgggcaccag ctttagcacc   1980

gaatatcgta ttagcggtct ggaaatcaaa aaacatggca acagcattga aatctgggca   2040

gttaatcgcc tgggcacagt tattgcacgt caggatattg atattcagca tcatcaccat   2100

caccattaa                                                           2109
```

```
<210> SEQ ID NO 10
<211> LENGTH: 2091
<212> TYPE: DNA
<213> ORGANISM: Rhizomucor pusillus

<400> SEQUENCE: 10

atgccttcac tcgaactaca gcaagctgct gacacgagac ttttcgagtc tatgccactt     60

cagactatga atgagcttgg ttcttgggaa cctagcaatg cctcgcgagc caacattgca    120

actattcctt tgcatcagcg atccaatctt gatccggcag agccgcgctt gatcgtaact    180

cacgatatgg ctggaggcta caaggaagac tcaaatattc agggcaatac gtatgataca    240

atttatagct gtcaatattg gcaatatgtg gatactttta tctatttctc gcatcatcga    300

gttacgatac ctcctgtcaa ttggataaat gcatgccaca gaaacggtgt caaaacgcta    360

ggaacattca ttgtggaagg aactgcgggc atgtttgcct tggagagatt cgtctacgga    420

cctgagcctg gacagagaaa cagctggagc ccttactatg ctgataagct ggtggacata    480
```

```
gccgagtttt acggtttcga cggctggctg cttaacattg agagtgattt cttcccttta    540

tatcgaaatc cgtctctgaa agcgatccat ctagcaaagc tgctgcgata tctgaagaat    600

gcaatgcacg ccagagtgcc aggttcagag atcatctggt atgacagcat gacgacaaac    660

ggaagtgtgc agtggcaaaa caatatcacg cccaaaaatt ccatattttt tgaagctgca    720

gatggcatat ttttaaatta ttggtggaac gcgacggttc cgccgttggc tttgcaagta    780

gcacatcgtc taggacgtca aggatctgat gtatactttg gaacggatgt ttggggacga    840

ggaacattcg gtggtggcgg attcgattca tatctcgctg ttggcactgc gagggcattc    900

aaaacatcat ctgcgctttt cggcacagca tggatctatg agcattttgg gaagaaagat    960

tttgagctta tggatagact tttgtggtta ggtggtgatc aatcagaata tccagctcag   1020

gaaggagagc agaatcgcac agtaaaagtt acatcccatc ttggaagaca tcctggtatc   1080

gccgatgtgt caccggtgcg aagtgctcca gggaaaacat ggttcgcaac gtggtttgat   1140

agaggttacg gaacaggttt ctattatcag ggcaagaaac tattatcaca gccgtggtcg   1200

catttatcgc atcaatctat cccgccgaat cttatagcca gattacagag agaagaaaat   1260

cacggccttt cgtatttcct ggcagacgac gatgcataca tcgggggtac ttcgctgtta   1320

atagcagccg aaatcactca agaacgccaa ttgccgctct atcaactaga gtatgacgtt   1380

actgaaggct gcgaggtgca gtttatatac aagtctccgg aaccagatat gcaaggaaaa   1440

atagatatat atttgaactt gcaagttaca gacatactgc ctgatgagct agcctttttac  1500

tggcaagatg ttacggatgc ttcctcccag gccgatgcaa cgacagccat gcgtttatat   1560

ctaaacgaaa acacagttat ttatctaaag ccgtccagga aacaagagct agccgaaggc   1620

tggttgctct gttccgtgcg tgtgccgcct acttatccac ttggtatcgc aacgatcaag   1680

gaactaggga tccatgtgga tggtacagaa acagtgctat ttaggctggg tctccttaca   1740

attatacccc ttggagatgc gccgtctgcg ctttccagaa ttacccaggt ccagcttcaa   1800

agggatgagg atatccatag taaatgtcca tcctcctcat gcgaactttg ggccacactc   1860

tcgtggatga tggaacacaa ctcaaaagag gactgggacc aggtcgatca ctatatgatt   1920

ttcttcaaaa atgttgattc caaggcagaa cctattttcc ttggcaccag cttcagtacc   1980

gagtacagaa tatcaggcct ggagatcaag aaacacggaa attccatcga gatatgggca   2040

gtaaatcgct taggaaccgt cattgcacgg caagacatcg atatccaata g            2091
```

```
<210> SEQ ID NO 11
<211> LENGTH: 2109
<212> TYPE: DNA
<213> ORGANISM: Artificial Sequence
<220> FEATURE:
<223> OTHER INFORMATION: Optimized DNA sequence for expression of
      Endo-Rp2 in E. coli

<400> SEQUENCE: 11

atgccgagcc tggaactgca gcaggcagca gatacccgtc tgtttgaaag catgccgctg     60

cagaccatga atgaactggg tagctgggaa ccgagcaatg caagccgtgc aaatattgca    120

accattccgc tgcatcagcg tagcaatctg gatccggcag aaccgcgtct gattgttacc    180

catgatatgg caggcggtta taaagaagat agcaatattc agggcaacac ctatgatacc    240

atttatagct gtcagtattg gcagtatgtg gacaccttta tctattttag ccatcaccgt    300

gttaccattc ctccggttaa ttggattaat gcctgtcatc gtaatggtgt taaaaccctg    360

ggcaccttta ttgttgaagg taccgcaggt atgtttgcac tggaacgttt tgtttatggt    420
```

ccggaaccgg gtcagcgtaa tagctggtca ccgtattatg cagataaact ggttgatatc 480
gccgagtttt atggttttga tggttggctg ctgaacatcg aaagcgattt ttttccgctg 540
tatcgtaatc cgagcctgaa agcaattcat ctggcaaaac tgctgcgcta tctgaaaaat 600
gcaatgcatg cacgtgttcc gggtagcgaa attatctggt atgatagcat gaccaccaat 660
ggtagcgttc agtggcagaa taacattacc ccgaaaaaca gcatcttttt tgaagcagcc 720
gatggcatct ttctgaatta ttggtggaat gcaaccgttc ctccgctggc actgcaggtt 780
gcacatcgtc tgggtcgtca gggtagtgat gtttattttg gcaccgatgt ttggggtcgt 840
ggcacctttg gtggtggtgg ctttgatagt tatctggcag ttggcaccgc acgtgcattt 900
aaaaccagca gcgcactgtt tggtacagca tggatttatg aacacttcgg caaaaaagac 960
ttcgaactga tggatcgtct gctgtggctg ggtggtgatc agagcgaata tccggcacaa 1020
gaaggtgaac agaatcgtac cgttaaagtt accagccatc tgggtcgcca tccgggtatt 1080
gcagatgtta gtccggttcg tagcgcaccg ggtaaaacct ggtttgcaac atggtttgat 1140
cgtggttatg gcaccggttt ctattatcag ggtaaaaaac tgctgagcca gccgtggtca 1200
catctgagcc atcagagcat tccgcctaat ctgattgcac gcctgcagcg tgaagaaaat 1260
catggcctga gctattttct ggcagatgat gatgcatata ttggtggcac cagcctgctg 1320
attgcagcag aaattaccca agaacgtcag ctgcctctgt atcagctgga atatgatgtt 1380
accgaaggtt gcgaagtgca gttcatctat aaaagccctg aaccggatat gcagggcaaa 1440
attgatatct atctgaatct gcaggttacc gatatcctgc cggatgaact ggcattttat 1500
tggcaggacg ttaccgatgc aagcagccag gcagatgcaa ccaccgcaat gcgtctgtat 1560
ctgaatgaaa ataccgtgat ttatctgaaa ccgagccgta aacaagaact ggcggaaggc 1620
tggctgctgt gtagcgttcg tgttccgcct acctatccgc tgggtattgc caccattaaa 1680
gaactgggca ttcatgtgga tggtaccgaa accgttctgt ttcgcctggg tctgctgacc 1740
attatcccgc tgggtgatgc accgagcgca ctgagccgta ttacccaggt tcagctgcaa 1800
cgtgatgaag atattcatag caaatgtccg agcagcagct gtgaactgtg ggcaaccctg 1860
agctggatga tggaacataa tagcaaagaa gattgggatc aggtcgatca ctacatgatc 1920
tttttcaaaa acgtggatag caaagccgaa ccgatttttc tgggcaccag ctttagcacc 1980
gaatatcgta ttagcggtct ggaaatcaaa aaacatggca acagcattga aatctgggca 2040
gttaatcgcc tgggcacagt tattgcacgt caggatattg atattcagca tcatcaccat 2100
caccattaa 2109

<210> SEQ ID NO 12
<211> LENGTH: 2091
<212> TYPE: DNA
<213> ORGANISM: Rhizomucor pusillus

<400> SEQUENCE: 12
atgccttcac tcgaactaca gcaagctgct gacacgagac ttttcgagtc tatgccactt 60
cagactatga atgagcttgg ttcttgggaa cctagcaatg cctcgcgagc caacattgca 120
actattcctt tgcatcagcg atccaatctt gatccggcag agccgcgctt gatcgtaact 180
cacgatatgg ctggaggcta caaggaagac tcaaatattc agggcaatac gtatgataca 240
atttatagct gtcaatattg gcaatatgtg gatactttta tctatttctc gcatcatcga 300
gttacgatac ctcctgtcaa ttggataaat gcatgccaca gaaacggtgt caaaacgcta 360

```
ggaacattca tcgtggaagg agctgcgggc atgtttgcct tggagagatt cgtctacgga    420

cctgagcctg gacagagaaa cagctggagc ccttactatg ctgataagct ggtggacata    480

gccgagtttt acggtttcga cggctggctg cttaacattg agagtgattt cttcccttta    540

tatcgaaatc cgtctctgaa agcgatccat ctagcaaagc tgctgcgata tctgaagaat    600

gcaatgcacg ccagagtgcc aggttcagag atcatctggt atgacagcat gacgacaaac    660

ggaagtgtgc agtggcaaaa caatatcacg cccaaaaatt ccatattttt tgaagctgca    720

gatggcatat ttttaaatta ttggtggaac gcgacggttc cgccgttggc tttgcaagta    780

gcacatcgtc taggacgtca aggatctgat gtatactttg gaacggatgt ttggggacga    840

ggaacattcg gtggtggcgg attcgattca tatctcgctg ttggcactgc gagggcattc    900

aaaacatcat ctgcgctttt cggcacagca tggatctatg agcattttgg gaagaaagat    960

tttgagctta tggatagact tttgtggtta ggtggtggtc aatcagaata tccagctcag   1020

gaaggagagc agaatcgcac agtaaaagtt acatcccatc ttggaagaca tcctggtatc   1080

gccgatgtgt caccggtgcg aagtgctcca gggaaaacat ggttcgcaac gtggtttgat   1140

agaggttacg gaacaggttt ctattatcag ggcaagaaac tattatcaca gccgtggtcg   1200

catttatcgc atcaatctat cccgccgaat cttatagcca gattacagag agaagaaaat   1260

cacggccttt cgtatttcct ggcagacgac gatgcatacc tcgggggaac ttcgttgtta   1320

atagcagccg aaatcactca agaacgccaa ttgccgctct atcaactaga gtatgacgtt   1380

actgaaggct gcgaggtgca gtttatatac aagtctccgg aaccagatat gcaaggaaaa   1440

atagatatat atttgaactt gcaagttaca gacatactgc ctgatgagct agccttttac   1500

tggcaagatg ttacggatgc ttcctcccag gccgatgcaa cgacagccat gcgtttatat   1560

ctaaacgaaa acacagttgt ttatctaaag ccatccagga aacaagagct agccgaaggc   1620

tggttgctct gttccgtgcg tgtgccacct acttatccac ttggtatcgc aacgatcaag   1680

gaactaggga tccacgtgga cggtacagaa acagtgctat ttaggctggg tctccttaca   1740

attatacccc ttggagatgc gccgtctgcg ctttccagaa ttacccaggt ccagcttcaa   1800

agggatgagg atatccatag taaatgttca tcctcctcat gcgaactttg ggccacactc   1860

tcgtggatga tggaacgcaa ttcaaaagag gactgggacc aggtcgatca ctatatgatt   1920

ttcttcaaaa atgttgattc caaggcagaa cctattttcc ttggcaccag cttcagtacc   1980

gagtacagaa tatcaggcct ggagatcaag aaacacggaa attccatcga gatatgggca   2040

gtaaatcgct taggaaccgt cattgcacgg caagacatcg atatccaata g            2091
```

<210> SEQ ID NO 13
<211> LENGTH: 2109
<212> TYPE: DNA
<213> ORGANISM: Artificial Sequence
<220> FEATURE:
<223> OTHER INFORMATION: Optimized DNA sequence for expression of Endo-Rp3 in E. coli

<400> SEQUENCE: 13

```
atgccgagcc tggaactgca gcaggcagca gatacccgtc tgtttgaaag catgccgctg     60

cagaccatga atgaactggg tagctgggaa ccgagcaatg caagccgtgc aaatattgca    120

accattccgc tgcatcagcg tagcaatctg gatccggcag aaccgcgtct gattgttacc    180

catgatatgg caggcggtta taaagaagat agcaatattc agggcaacac ctatgatacc    240

atttatagct gtcagtattg gcagtatgtg gacaccttta tctattttag ccatcaccgt    300
```

-continued

```
gttaccattc ctccggttaa ttggattaat gcctgtcatc gtaatggtgt taaaaccctg    360
ggcaccttta ttgttgaagg tgcagcaggt atgtttgcac tggaacgttt tgtttatggt    420
ccggaaccgg gtcagcgtaa tagctggtca ccgtattatg cagataaact ggttgatatc    480
gccgagtttt atggttttga tggttggctg ctgaacatcg aaagcgattt ttttccgctg    540
tatcgtaatc cgagcctgaa agcaattcat ctggcaaaac tgctgcgcta tctgaaaaat    600
gcaatgcatg cacgtgttcc gggtagcgaa attatctggt atgatagcat gaccaccaat    660
ggtagcgttc agtggcagaa taacattacc ccgaaaaaca gcatcttttt tgaagcagcc    720
gatggcatct ttctgaatta ttggtggaat gcaaccgttc ctccgctggc actgcaggtt    780
gcacatcgtc tgggtcgtca gggtagtgat gtttattttg gcaccgatgt ttggggtcgt    840
ggcacctttg gtggtggtgg ctttgatagt tatctggcag ttggcaccgc acgtgcattt    900
aaaaccagca gcgcactgtt tggtacagca tggatttatg aacacttcgg caaaaaagac    960
ttcgaactga tggatcgtct gctgtggctg ggtggtggtc agagcgaata tccggcacaa   1020
gaaggtgaac agaatcgtac cgttaaagtt accagccatc tgggtcgcca tccgggtatt   1080
gcagatgtta gtccggttcg tagcgcaccg ggtaaaacct ggtttgcaac atggtttgat   1140
cgtggttatg gcaccggttt ctattatcag ggtaaaaaac tgctgagcca gccgtggtca   1200
catctgagcc atcagagcat tccgcctaat ctgattgcac gcctgcagcg tgaagaaaat   1260
catggcctga gctattttct ggcagatgat gatgcatatc tgggtggcac cagcctgctg   1320
attgcagcag aaattaccca agaacgtcag ctgcctctgt atcagctgga atatgatgtt   1380
accgaaggtt gcgaagtgca gttcatctat aaaagccctg aaccggatat gcagggcaaa   1440
attgatatct atctgaatct gcaggttacc gatatcctgc cggatgaact ggcattttat   1500
tggcaggacg ttaccgatgc aagcagccag gcagatgcaa ccaccgcaat gcgtctgtat   1560
ctgaatgaaa ataccgtggt ctatctgaaa ccgagccgta aacaagaact ggcggaaggc   1620
tggctgctgt gtagcgttcg tgttccgcct acctatccgc tgggtattgc caccattaaa   1680
gaactgggca ttcatgtgga tggtaccgaa accgttctgt ttcgcctggg tctgctgacc   1740
attatcccgc tgggtgatgc accgagcgca ctgagccgta ttacccaggt tcagctgcaa   1800
cgtgatgaag atattcatag caaatgtagc agcagcagct gtgaactgtg ggcaaccctg   1860
agctggatga tggaacgtaa tagcaaagaa gattgggatc aggtcgatca ctacatgatc   1920
tttttcaaaa acgtggatag caaagccgaa ccgatttttc tgggcaccag ctttagcacc   1980
gaatatcgta ttagcggtct ggaaatcaaa aaacatggca acagcattga aatctgggca   2040
gttaatcgcc tgggcacagt tattgcacgt caggatattg atattcagca tcatcaccat   2100
caccattaa                                                           2109
```

<210> SEQ ID NO 14
<211> LENGTH: 2091
<212> TYPE: DNA
<213> ORGANISM: Rhizomucor pusillus

<400> SEQUENCE: 14

```
atgccttcac tcgaactaca gcaagctgct gacacgagac ttttcgagtc tatgccactt     60
cagactatga atgagcttgg ttcttgggaa cctagcaatg cctcgcgagc caacattgca    120
actattcctt tgcatcagcg atccaatctt gatccggcag agccgcgctt gatcgtaact    180
cacgatatgg ctggaggcta caaggaagac tcaaatattc agggcaatac gtatgataca    240
atttatagct gtcaatattg gcaatatgtg gatactttta tctatttctc gcatcatcga    300
```

```
gttacgatac ctcctgtcaa ttggataaat gcatgccaca gaaacggtgt caaaacgcta    360

ggaacattca ttgtggaagg agctgcgggc atgtttgcct tggagagatt cgtctacgga    420

cctgagcctg gacagagaaa cagctggagc ccttactatg ctgataagct ggtggacata    480

gccgagtttt acggtttcga cggctggctg cttaacattg agagtgattt tttcccttta    540

tatcgaaatc cgtctctgaa agcgatccat ctagcaaagc tgctgcgata tctgaagaat    600

gcaatgcacg ccagagtgcc aggttcagag atcatctggt atgacagcat gacgacaaac    660

ggaagtgtgc agtggcaaaa caatatcacg cccaaaaatt ccatattttt tgaagctgca    720

gatggcatat ttttaaatta ttggtggaac gcgacggttc cgccgttggc tttgcaagta    780

gcacatcgtc taggacgtca aggatctgat gtatactttg gaacggatgt ttggggacga    840

ggaacattcg gtggtggcgg attcgattca tatctcgctg ttggcactgc gagggcattc    900

aaaacatcat ctgcgctttt cggcacagca tggatctatg agcattttgg gaagaaagat    960

tttgagctta tggatagact tttgtggtta ggtggtgatc aatcagaata tccagctcag   1020

gaaggagagc agaatcgcac agtaaaagtt acatcccatc ttggaagaca tcctggtatc   1080

gccgatgtgt caccggtgcg aagtgctcca gggaaaacat ggttcgcaac gtggtttgat   1140

agaggttacg gaacaggttt ctattatcag ggcaagaaac tattatcaca gccgtggtcg   1200

catttatcgc atcaatctat cccgccgaat cttatagcca gattacagag agaagaaaat   1260

cacggccttt cgtatttcct ggcagacgac gatgcataca tcgggggaac ttcgctgtta   1320

atagcagccg aaatcactca agaacgccaa ttgccgctct atcaactaga gtatgacgct   1380

actgaaggct gcgaggtgca gtttatatac aagtctccgg aaccagatat gcaaggaaaa   1440

atagatatat atttgaactt gcaagttaca gacatactgc ctgatgagct agccttttac   1500

tggcaagatg ttacggatgc ttcctcccag gccgatgcaa cgacagccat gcgtttatat   1560

ctaaacgaaa acacagttat ttatctaaag ccgtccagga aacaagagct agccgaaggc   1620

tggttgctct gttccgtgcg tgtgccacct acttatccac ttggtatcgc aacgatcaag   1680

gaactaggga tccatgtgga tggtacagaa acagtgctat ttaggctggg tctccttaca   1740

attatacccc ttggagatgc gccgtctgcg ctttccagaa ttacccaggt ccagcttcaa   1800

agggatgagg atatccatag taaatgtcca tcctcctcat gcgaactttg ggccacactc   1860

tcgtggatga tggaacacaa ctcaaaagag gactgggacc aggtcgatca ctatatgatt   1920

ttcttcaaaa atgttgattc caaggcagaa cctattttcc ttggcaccag cttcagtacc   1980

gagtacagaa tatcaggcct ggagatcaag aaacacggaa attccatcga gatatgggca   2040

gtaaatcgct taggaaccgt cattgcacgg caagacatcg atatccaata g            2091
```

```
<210> SEQ ID NO 15
<211> LENGTH: 2109
<212> TYPE: DNA
<213> ORGANISM: Artificial Sequence
<220> FEATURE:
<223> OTHER INFORMATION: Optimized DNA sequence for expression of
      Endo-Rp4 in E. coli

<400> SEQUENCE: 15

atgccgagcc tggaactgca gcaggcagca gatacccgtc tgtttgaaag catgccgctg     60

cagaccatga atgaactggg tagctgggaa ccgagcaatg caagccgtgc aaatattgca    120

accattccgc tgcatcagcg tagcaatctg gatccggcag aaccgcgtct gattgttacc    180

catgatatgg caggcggtta taaagaagat agcaatattc agggcaacac ctatgatacc    240
```

```
atttatagct gtcagtattg gcagtatgtg gacaccttta tctattttag ccatcaccgt    300
gttaccattc ctccggttaa ttggattaat gcctgtcatc gtaatggtgt taaaaccctg    360
ggcaccttta ttgttgaagg tgcagcaggt atgtttgcac tggaacgttt tgtttatggt    420
ccggaaccgg gtcagcgtaa tagctggtca ccgtattatg cagataaact ggttgatatc    480
gccgagtttt atggttttga tggttggctg ctgaacatcg aaagcgattt ttttccgctg    540
tatcgtaatc cgagcctgaa agcaattcat ctggcaaaac tgctgcgcta tctgaaaaat    600
gcaatgcatg cacgtgttcc gggtagcgaa attatctggt atgatagcat gaccaccaat    660
ggtagcgttc agtggcagaa taacattacc ccgaaaaaca gcatcttttt tgaagcagcc    720
gatggcatct ttctgaatta ttggtggaat gcaaccgttc ctccgctggc actgcaggtt    780
gcacatcgtc tgggtcgtca gggtagtgat gtttattttg gcaccgatgt ttggggtcgt    840
ggcacctttg gtggtggtgg ctttgatagt tatctggcag ttggcaccgc acgtgcattt    900
aaaaccagca gcgcactgtt tggtacagca tggatttatg aacacttcgg caaaaaagac    960
ttcgaactga tggatcgtct gctgtggctg ggtggtgatc agagcgaata tccggcacaa   1020
gaaggtgaac agaatcgtac cgttaaagtt accagccatc tgggtcgcca tccgggtatt   1080
gcagatgtta gtccggttcg tagcgcaccg ggtaaaacct ggtttgcaac atggtttgat   1140
cgtggttatg gcaccggttt ctattatcag ggtaaaaaac tgctgagcca gccgtggtca   1200
catctgagcc atcagagcat tccgcctaat ctgattgcac gcctgcagcg tgaagaaaat   1260
catggcctga gctattttct ggcagatgat gatgcatata ttggtggcac cagcctgctg   1320
attgcagcag aaattaccca agaacgtcag ctgcctctgt atcagctgga atatgatgca   1380
accgaaggtt gcgaagtgca gttcatctat aaaagccctg aaccggatat gcagggcaaa   1440
attgatatct atctgaatct gcaggttacc gatatcctgc cggatgaact ggcattttat   1500
tggcaggacg ttaccgatgc aagcagccag gcagatgcaa ccaccgcaat gcgtctgtat   1560
ctgaatgaaa ataccgtgat ttatctgaaa ccgagccgta aacaagaact ggcggaaggc   1620
tggctgctgt gtagcgttcg tgttccgcct acctatccgc tgggtattgc caccattaaa   1680
gaactgggca ttcatgtgga tggtaccgaa accgttctgt ttcgcctggg tctgctgacc   1740
attatcccgc tgggtgatgc accgagcgca ctgagccgta ttacccaggt tcagctgcaa   1800
cgtgatgaag atattcatag caaatgtccg agcagcagct gtgaactgtg ggcaaccctg   1860
agctggatga tggaacataa tagcaaagaa gattgggatc aggtcgatca ctacatgatc   1920
tttttcaaaa acgtggatag caaagccgaa ccgatttttc tgggcaccag ctttagcacc   1980
gaatatcgta ttagcggtct ggaaatcaaa aaacatggca acagcattga aatctgggca   2040
gttaatcgcc tgggcacagt tattgcacgt caggatattg atattcagca tcatcaccat   2100
caccattaa                                                           2109
```

<210> SEQ ID NO 16
<211> LENGTH: 2091
<212> TYPE: DNA
<213> ORGANISM: Rhizomucor pusillus

<400> SEQUENCE: 16

```
atgccttcac tcgaactaca gcaagctgct gacacgagac ttttcgagtc tatgccactt     60
cagactatga atgagcttgg ttcttgggaa cctagcaatg cctcgcgagc caacattgca    120
actattcctt tgcatcagcg atccaatctt gatccggcag agccgcgctt gatcgtaact    180
```

```
cacgatatgg ctggaggcta caaggaagac tcaaatattc agggcaatac gtatgataca    240

atttatagct gtcaatattg gcaatatgtg gatactttta tctatttctc gcatcatcga    300

gttacgatac ctcctgtcaa ttggataaat gcatgccaca gaaacggtgt caaaacgcta    360

ggaacattca ttgtggaagg agctgcgggc atgtttgcct tggagagatt cgtctacgga    420

cctgagcctg gacagagaaa cagctggagc ccttactatg ctgataagct ggtggacata    480

gccgagtttt acggtttcga cggctggctg cttaacattg agagtgattt cttcccttta    540

tatcgaaatc cgtctctgaa agcgatccat ctagcaaagc tgctgcgata tctgaagaat    600

gcaatgcacg ccagagtgcc aggttcagag atcatctggt atgacagcat gacgacaaac    660

ggaagtgtgc agtggcaaaa caatatcacg cccaaaaatt ccatattttt tgaagctgca    720

gatggcatat ttttaaatta ttggtggaac gcgacggttc cgccgttggc tttgcaagta    780

gcacatcgtc taggacgtca aggatctgat gtatactttg gaacggatgt ttggggacga    840

ggaacattcg gtggtggcgg attcgattca tatctcgctg ttggcactgc gagggcattc    900

aaaacatcat ctgcgctttt cggcacagca tggatctatg agcattttgg gaagaaagat    960

tttgagctta tggatagact tttgtggtta ggtggtgatc aatcagaata tccagctcag   1020

gaaggagagc agaatcgcac agtaaaagtt acatcccatc ttggaagaca tcctggtatc   1080

gccgatgtgt caccggtgcg aagtgctcca gggaaaacat ggttcgcaac gtggtttgat   1140

agaggttacg gaacaggttt ctattatcag ggcaagaaac tattatcaca gccgtggtcg   1200

catttatcgc atcaatctat cccgccgaat cttatagcca gattacagag agaagaaaat   1260

cacggccttt cgtatttcct ggcagacgac gatgcataca tcgggggaac ttcgctgtta   1320

atagcagccg aaatcactca agaacgccaa ttgccgctct atcaactaga gtatgacgtt   1380

actgaaggct gcgaggtgca gtttatatac aagtctccgg aaccagatat gcaaggaaaa   1440

atagatatat atttgaactt gcaagttaca gacatactgc ctgatgagct agccttttac   1500

tggcaagatg ttacggatgc ttcctcccag gccgatgcaa cgacagccat gcgtttatat   1560

ctaaacgaaa acacagttat ttatctaaag ccgtccagga aacaagagct agccgaaggc   1620

tggttgctct gttccgtgcg tgtgccacct acttatccac ttggtatcgc aacgatcaag   1680

gaactaggga tccatgtgga tggtacagaa acagtgctat ttaggctggg tctccttaca   1740

attatacccc ttggagatgc gccgtctgcg ctttccagaa ttacccaggt ccagcttcaa   1800

agggatgagg atatccatag taaatgtcca tcctcctcat gcgaactttg ggccacactc   1860

tcgtggatga tggaacacaa ctcaaaagag gactgggacc aggtcgatca ctatatgatt   1920

ttcttcaaaa atgttgattc caaggcagaa cctattttcc ttggcaccag cttcagtacc   1980

gagtacagaa tatcaggcct ggagatcaag aaacacggaa attccatcga gatatgggca   2040

gtaaatcgct taggaaccgt cattgcacgg caagacatcg atatccaata g            2091
```

<210> SEQ ID NO 17
<211> LENGTH: 2109
<212> TYPE: DNA
<213> ORGANISM: Artificial Sequence
<220> FEATURE:
<223> OTHER INFORMATION: Optimized DNA sequence for expression of Endo-Rp5 in E. coli

<400> SEQUENCE: 17

```
atgccgagcc tggaactgca gcaggcagca gatacccgtc tgtttgaaag catgccgctg     60

cagaccatga atgaactggg tagctgggaa ccgagcaatg caagccgtgc aaatattgca    120
```

```
accattccgc tgcatcagcg tagcaatctg gatccggcag aaccgcgtct gattgttacc    180
catgatatgg caggcggtta taaagaagat agcaatattc agggcaacac ctatgatacc    240
atttatagct gtcagtattg gcagtatgtg gacaccttta tctattttag ccatcaccgt    300
gttaccattc ctccggttaa ttggattaat gcctgtcatc gtaatggtgt taaaaccctg    360
ggcaccttta ttgttgaagg tgcagcaggt atgtttgcac tggaacgttt tgtttatggt    420
ccggaaccgg gtcagcgtaa tagctggtca ccgtattatg cagataaact ggttgatatc    480
gccgagtttt atggttttga tggttggctg ctgaacatcg aaagcgattt ttttccgctg    540
tatcgtaatc cgagcctgaa agcaattcat ctggcaaaac tgctgcgcta tctgaaaaat    600
gcaatgcatg cacgtgttcc gggtagcgaa attatctggt atgatagcat gaccaccaat    660
ggtagcgttc agtggcagaa taacattacc ccgaaaaaca gcatcttttt tgaagcagcc    720
gatggcatct ttctgaatta ttggtggaat gcaaccgttc ctccgctggc actgcaggtt    780
gcacatcgtc tgggtcgtca gggtagtgat gtttattttg gcaccgatgt ttggggtcgt    840
ggcacctttg gtggtggtgg ctttgatagt tatctggcag ttggcaccgc acgtgcattt    900
aaaaccagca gcgcactgtt tggtacagca tggatttatg aacacttcgg caaaaaagac    960
ttcgaactga tggatcgtct gctgtggctg ggtggtgatc agagcgaata tccggcacaa   1020
gaaggtgaac agaatcgtac cgttaaagtt accagccatc tgggtcgcca tccgggtatt   1080
gcagatgtta gtccggttcg tagcgcaccg ggtaaaacct ggtttgcaac atggtttgat   1140
cgtggttatg gcaccggttt ctattatcag ggtaaaaaac tgctgagcca gccgtggtca   1200
catctgagcc atcagagcat tccgcctaat ctgattgcac gcctgcagcg tgaagaaaat   1260
catggcctga gctattttct ggcagatgat gatgcatata ttggtggcac cagcctgctg   1320
attgcagcag aaattaccca agaacgtcag ctgcctctgt atcagctgga atatgatgtt   1380
accgaaggtt gcgaagtgca gttcatctat aaaagccctg aaccggatat gcagggcaaa   1440
attgatatct atctgaatct gcaggttacc gatatcctgc cggatgaact ggcattttat   1500
tggcaggacg ttaccgatgc aagcagccag gcagatgcaa ccaccgcaat gcgtctgtat   1560
ctgaatgaaa ataccgtgat ttatctgaaa ccgagccgta aacaagaact ggcggaaggc   1620
tggctgctgt gtagcgttcg tgttccgcct acctatccgc tgggtattgc caccattaaa   1680
gaactgggca ttcatgtgga tggtaccgaa accgttctgt ttcgcctggg tctgctgacc   1740
attatcccgc tgggtgatgc accgagcgca ctgagccgta ttacccaggt tcagctgcaa   1800
cgtgatgaag atattcatag caaatgtccg agcagcagct gtgaactgtg ggcaaccctg   1860
agctggatga tggaacataa tagcaaagaa gattgggatc aggtcgatca ctacatgatc   1920
tttttcaaaa acgtggatag caaagccgaa ccgatttttc tgggcaccag ctttagcacc   1980
gaatatcgta ttagcggtct ggaaatcaaa aaacatggca acagcattga aatctgggca   2040
gttaatcgcc tgggcacagt tattgcacgt caggatattg atattcagca tcatcaccat   2100
caccattaa                                                           2109
```

<210> SEQ ID NO 18
<211> LENGTH: 2094
<212> TYPE: DNA
<213> ORGANISM: Rhizomucor miehei

<400> SEQUENCE: 18

```
atgccctcac tcgaacttca gcaagccgtg gacacaagac tcttcgagtc aacaccactt     60
atgactatgg atgagcttgg ctcctgggat cctagcaatg ctttgcgagc cagcattgcg    120
```

```
acagttcctc tgcatccgcg accaagcatc gatccgacag aaccacgctt gattgtgaca    180

cacgatatgg caggaggcta caaggaagac tttagtattc agggcaatgc atatgacacc    240

gtttacacct gccaatattg gcaatacgtg gacattttta tctacttctc gcatcatcga    300

gttacgatac cacccgtaaa ctggacgaat gcttgccaca ggaacggtgt caaaagtctc    360

ggaacattta ttgttgaagg agcagcaggc atgtttgccc tggagaggtt cgtgtatggc    420

cctaaccctg ggcaaaggaa gagctggagc ccatattatg cagataagct agtggacatt    480

gccgaatttt atggtttcga tggatggttg atcaatattg aaagcgattt tttccctctg    540

tatcgaagcc cgtcaatgaa ggcgaaacat ttggcaaagc tgctgctata tctcaggaat    600

gctatgcatg ccagagtacc gggttcgcag atcatctggt atgacagcat gaccacaagt    660

ggatacgttc aatggcaaaa caatattaca cctcagaatg agatattctt tgaggctgcc    720

gatggtatat tttgaatta ctggtggaat gcaacatacc caccttttgc catgcaggta    780

gcgcattatc tgggtcgcca aggatccgat gtatactttg gttctgacat ttggggacga    840

ggaacttttg gtggtggtgg cttcgattca tacctggcag ttgctaccgc gagtgctttt    900

aagacgtcat ctgcactttt cggcacagca tggacttatg aacattttga aaagaaggac    960

tttgagctga tggataggct actgtggtta ggcggtgatc aatcagagta tccagctcaa   1020

gcagaagggc aggaaagcat agcaaagtct gggtcgcgac tcggaagaca cccaggcatt   1080

accgatgtgg ctgcagttcg tagcgctcca ggtcgaagat ggtttgtaac ttggttcgat   1140

agaggacatg gaaccggttt ctatcatcaa ggaaagaaac tactatcaca accatggtcc   1200

catttgtctc atcaatctat accgcccaat ctcgtcgcca gactgcaaag gaaagaagat   1260

gacggcgttt cgtacttctt ggccgacgat gatgcttaca ttggaggaac gtctctatta   1320

atagcagcag agggtaccca agaacgtcag ataccacttt atcaactgaa ttatgacgcc   1380

acaaacggat gtgaagtgca gtttgtttat aagtccccag agccggatat gcaaagcaaa   1440

gtgcagatat atttgaacct cagagtgaca gatgttctac ctgacgaact cgcttactac   1500

tggcacgacg ttgcagctac ctctccccag cctcaggcaa caacagcctc gcgtttgaac   1560

atcaacgaag acaccagtgt ttatttgaat acttcgaaga cgcaagaatt ggcagaaggc   1620

tgggtgttgt gctccgttcg agtgccatct gttcacccgc taggcgaagc tgcaattgaa   1680

gaattaggaa tctatttgga cggaactgag gatgtgctgt tcagattggg gcttttgact   1740

atcgtgccct acacagatac gtcatctact cttgcaagca aaataactca catccagctt   1800

caaagggatg cagacgtcag cagtaaatgc ttatcatctt cgtgcgaact ctgggctacg   1860

ttatcctgga tgatggagtc gaattctagt gaggaatgga accaagtcga tcactatctc   1920

atttcctacg gagatatcaa tgctgatggt gcagctacat ttctcggtac tactttcact   1980

acagagtata ggatatcagg tctggagatg aagaatgaca tcgactatat ccaaatttcg   2040

gcagtgagcc gcctaggcaa tatacttgca cagcaaacga tcggcataca gtag         2094
```

<210> SEQ ID NO 19
<211> LENGTH: 2112
<212> TYPE: DNA
<213> ORGANISM: Artificial Sequence
<220> FEATURE:
<223> OTHER INFORMATION: Optimized DNA sequence for expression of
Endo-Rm in E. coli

<400> SEQUENCE: 19

```
atgccgagcc tggaactgca gcaggcagtt gatacccgtc tgtttgaaag cacaccgctg     60
```

atgaccatgg atgaactggg tagctgggat ccgagcaatg cactgcgtgc aagcattgca 120
accgttccgc tgcatccgcg tccgagcatt gatccgaccg aaccgcgtct gattgttacc 180
catgatatgg caggcggtta taaagaagat tttagcattc agggcaacgc ctatgatacc 240
gtttatacct gtcagtattg gcagtatgtg gacatcttta tctattttag ccatcaccgt 300
gttaccattc cgcctgttaa ttggaccaat gcatgtcatc gtaatggtgt taaaagcctg 360
ggcaccttta ttgttgaagg tgcagcaggt atgtttgcac tggaacgttt tgtttatggt 420
ccgaatccgg gtcagcgtaa aagctggtca ccgtattatg cagataaact ggttgatatc 480
gccgagtttt atggttttga tggttggctg attaacatcg agagcgattt ttttccgctg 540
tatcgtagcc cgagcatgaa agcaaaacat ctggcaaaac tgctgctgta tctgcgtaat 600
gcaatgcatg cccgtgttcc gggtagccag attatttggt atgatagcat gaccaccagt 660
ggttatgttc agtggcagaa taacattaca ccgcagaacg aaatcttttt tgaagcagcc 720
gatggcatct ttctgaatta ttggtggaat gcaacctatc cgccttttgc aatgcaggtt 780
gcacattatc tgggtcgtca gggtagtgat gtttattttg gtagcgatat ttggggtcgt 840
ggcacctttg gtggtggtgg ctttgatagt tatctggcag ttgcaaccgc aagcgcattt 900
aaaaccagca gcgcactgtt tggcaccgca tggacctatg aacattttga gaaaaaagac 960
ttcgagctga tggatcgtct gctgtggctg ggtggtgatc agagcgaata tccggcacag 1020
gcagaaggtc aagaaagcat tgccaaaagc ggtagccgtc tgggtcgcca tccgggtatt 1080
accgatgttg cagcagttcg tagcgcaccg ggtcgtcgtt ggtttgttac ctggtttgat 1140
cgtggtcatg gcaccggttt ttatcatcag ggtaaaaaac tgctgagcca gccgtggtca 1200
catctgagcc atcagagcat tcctccgaat ctggttgcac gtctgcagcg caaagaagat 1260
gacggcgtta gctattttct ggcagatgat gatgcatata ttggtggcac cagcctgctg 1320
attgcagcag aaggcaccca agaacgtcag attcctctgt atcagctgaa ttatgatgca 1380
accaatggtt gtgaagtgca gttcgtgtat aaaagtccgg aaccggatat gcagagcaaa 1440
gttcagattt atctgaatct gcgtgtgacc gatgttctgc cggatgagct ggcatattat 1500
tggcatgatg ttgccgcaac cagtccgcag ccgcaggcaa ccaccgcaag ccgtctgaat 1560
attaacgaag ataccagcgt gtatctgaac accagcaaaa cacaagaact ggccgaaggt 1620
tgggttctgt gtagcgttcg tgttccgagc gttcatccgc tgggtgaagc agcaattgaa 1680
gaactgggca tttatctgga tggcaccgaa gatgttctgt ttcgcctggg tctgctgacc 1740
attgttccgt ataccgatac cagcagcacc ctggcaagca aaatcaccca tattcagctg 1800
cagcgtgatg cagatgttag cagcaaatgt ctgagcagca gctgtgaact gtgggcaacc 1860
ctgagctgga tgatggaaag caatagcagc gaagaatgga atcaggtgga tcattatctg 1920
attagctatg gcgatattaa tgcagatggt gcagccacct ttctgggcac cacctttacc 1980
accgaatatc gtattagcgg tctggaaatg aaaaacgaca tcgattacat tcagattagc 2040
gcagttagtc gtctgggtaa tattctggcc cagcagacca ttggtattca gcatcatcac 2100
catcaccact aa 2112

<210> SEQ ID NO 20
<211> LENGTH: 2106
<212> TYPE: DNA
<213> ORGANISM: Artificial Sequence
<220> FEATURE:
<223> OTHER INFORMATION: The assumed DNA sequence derived from publicly available genomic DNA sequence of Rhizomucor pusillus strain CBS 183.67, which has been assumed to encode endo-beta-N-acetylglucosaminidase.

<400> SEQUENCE: 20

```
atgccttcac tcgaactaca gcaagctgct gacacgagac ttttcgagtc tatgccactt     60
cagactatga atgagcttgg ttcttgggaa cctagcaatg cctcgcgagc caacattgca    120
actattcctt tgcatcagcg atccaatctt gatccggcag agccgcgctt gatcgtaact    180
cacgatatgg ctggaggcta caaggaagac tcaaatattc agggcaatac gtatgataca    240
atttatagct gtcaatattg gcaatatgtg gatactttta tctatttctc gcatcatcga    300
gttacgatac ctcctgtcaa ttggataaat gcatgccaca gaaacggtgt caaaacgcta    360
ggaacattca ttgtggaagg agctgcgggc atgtttgcct tggagagatt cgtctacgga    420
cctgagcctg gacagagaaa cagctggagc ccttactatg ctgataagct ggtggacata    480
gccgagtttt acggtttcga cggctggctg cttaacattg agagtgattt cttcccttta    540
tatcgaaatc cgtctctgaa agcgatccat ctagcaaata catattatat aaggctgctg    600
cgatatctga agaatgcaat gcacgccaga gtgccaggtt cagagatcat ctggtatgac    660
agcatgacga caaacggaag tgtgcagtgg caaaacaata tcacgcccaa aaattccata    720
ttttttgaag ctgcagatgg catattttta aattattggt ggaacgcgac ggttccgccg    780
ttggctttgc aagtagcaca tcgtctagga cgtcaaggat ctgatgtata ctttggaacg    840
gatgtttggg gacgaggaac attcggtggt ggcggattcg attcatatct cgctgttggc    900
actgcgaggg cattcaaaac atcatctgcg cttttcggca cagcatggat ctatgagcat    960
tttgggaaga aagattttga gcttatggat agacttttgt ggttaggtgg tgatcaatca   1020
gaatatccag ctcaggaagg agagcagaat cgcacagtaa aagttacatc ccatcttgga   1080
agacatcctg gtatcgccga tgtgtcaccg gtgcgaagtg ctccagggaa aacatggttc   1140
gcaacgtggt ttgatagagg ttacggaaca ggtttctatt atcagggcaa gaaactatta   1200
tcacagccgt ggtcgcattt atcgcatcaa tctatcccgc cgaatcttat agccagatta   1260
cagagagaag aaaatcacgg cctttcgtat ttcctggcag acgacgatgc atacatcggg   1320
ggaacttcgc tgttaatagc agccgaaatc actcaagaac gccaattgcc gctctatcaa   1380
ctagagtatg acgttactga aggctgcgag gtgcagttta tatacaagtc tccggaacca   1440
gatatgcaag gaaaaataga tatatatttg aacttgcaag ttacagacat actgcctgat   1500
gagctagcct tttactggca agatgttacg gatgcttcct cccaggccga tgcaacgaca   1560
gccatgcgtt tatatctaaa cgaaaacaca gttatttatc taaagccgtc caggaaacaa   1620
gagctagccg aaggctggtt gctctgttcc gtgcgtgtgc cacctactta tccacttggt   1680
atcgcaacga tcaaggaact agggatccat gtggatggta cagaaacagt gctatttagg   1740
ctgggtctcc ttacaattat accccttgga gatgcgccgt ctgcgctttc cagaattacc   1800
caggtccagc ttcaaaggga tgaggatatc catagtaaat gtccatcctc ctcatgcgaa   1860
ctttgggcca cactctcgtg gatgatggaa cacaactcaa aagaggactg ggaccaggtc   1920
gatcactata tgattttctt caaaaatgtt gattccaagg cagaacctat tttccttggc   1980
accagcttca gtaccgagta cagaatatca ggcctggaga tcaagaaaca cggaaattcc   2040
atcgagatat gggcagtaaa tcgcttagga accgtcattg cacggcaaga catcgatatc   2100
caatag                                                              2106
```

<210> SEQ ID NO 21

<211> LENGTH: 2124
<212> TYPE: DNA
<213> ORGANISM: Artificial Sequence
<220> FEATURE:
<223> OTHER INFORMATION: Optimized DNA sequence for expression of the assumed amino acid sequence of SEQ ID NO:7 in E. coli

<400> SEQUENCE: 21

```
atgccgagcc tggaactgca gcaggcagca gatacccgtc tgtttgaaag catgccgctg     60

cagaccatga atgaactggg tagctgggaa ccgagcaatg caagccgtgc aaatattgca    120

accattccgc tgcatcagcg tagcaatctg gatccggcag aaccgcgtct gattgttacc    180

catgatatgg caggcggtta taaagaagat agcaatattc agggcaacac ctatgatacc    240

atttatagct gtcagtattg gcagtatgtg gacaccttta tctattttag ccatcaccgt    300

gttaccattc ctccggttaa ttggattaat gcctgtcatc gtaatggtgt taaaaccctg    360

ggcaccttta ttgttgaagg tgcagcaggt atgtttgcac tggaacgttt tgtttatggt    420

ccggaaccgg gtcagcgtaa tagctggtca ccgtattatg cagataaact ggttgatatc    480

gccgagtttt atggttttga tggttggctg ctgaacatcg aaagcgattt ttttccgctg    540

tatcgtaatc cgagcctgaa agcaattcat ctggcaaaca cctattatat ccgtctgctg    600

cgctatctga aaaatgcaat gcatgcacgt gttccgggta gcgaaattat ctggtatgat    660

agcatgacca ccaatggtag cgttcagtgg cagaataaca ttaccccgaa aaacagcatc    720

tttttgaag cagccgatgg catctttctg aattattggt ggaatgcaac cgttcctccg    780

ctggcactgc aggttgcaca tcgtctgggt cgtcagggta gtgatgttta ttttggcacc    840

gatgtttggg gtcgtggcac ctttggtggt ggtggctttg atagttatct ggcagttggc    900

accgcacgtg catttaaaac cagcagcgca ctgtttggta cagcatggat ttatgaacac    960

ttcggcaaaa aagacttcga actgatggat cgtctgctgt ggctgggtgg tgatcagagc   1020

gaatatccgg cacaagaagg tgaacagaat cgtaccgtta aagttaccag ccatctgggt   1080

cgccatccgg gtattgcaga tgttagtccg gttcgtagcg caccgggtaa aacctggttt   1140

gcaacatggt ttgatcgtgg ttatggcacc ggtttctatt atcagggtaa aaaactgctg   1200

agccagccgt ggtcacatct gagccatcag agcattccgc ctaatctgat tgcacgcctg   1260

cagcgtgaag aaaatcatgg cctgagctat tttctggcag atgatgatgc atatattggt   1320

ggcaccagcc tgctgattgc agcagaaatt acccaagaac gtcagctgcc tctgtatcag   1380

ctggaatatg atgttaccga aggttgcgaa gtgcagttca tctataaaag ccctgaaccg   1440

gatatgcagg gcaaaattga tatctatctg aatctgcagg ttaccgatat cctgccggat   1500

gaactggcat tttattggca ggacgttacc gatgcaagca gccaggcaga tgcaaccacc   1560

gcaatgcgtc tgtatctgaa tgaaaatacc gtgatttatc tgaaaccgag ccgtaaacaa   1620

gaactggcgg aaggctggct gctgtgtagc gttcgtgttc cgcctaccta tccgctgggt   1680

attgccacca ttaaagaact gggcattcat gtggatggta ccgaaaccgt tctgtttcgc   1740

ctgggtctgc tgaccattat cccgctgggt gatgcaccga gcgcactgag ccgtattacc   1800

caggttcagc tgcaacgtga tgaagatatt catagcaaat gtccgagcag cagctgtgaa   1860

ctgtgggcaa ccctgagctg gatgatggaa cataatagca aagaagattg ggatcaggtc   1920

gatcactaca tgatcttttt caaaaacgtg gatagcaaag ccgaaccgat tttctgggc   1980

accagcttta gcaccgaata tcgtattagc ggtctggaaa tcaaaaaaca tggcaacagc   2040

attgaaatct gggcagttaa tcgcctgggc acagttattg cacgtcagga tattgatatt   2100
```

cagcatcatc accatcacca ttaa 2124

<210> SEQ ID NO 22
<211> LENGTH: 26
<212> TYPE: DNA
<213> ORGANISM: Artificial Sequence
<220> FEATURE:
<223> OTHER INFORMATION: PCR primer for cloning of Endo-Rp gene

<400> SEQUENCE: 22
atgccttcac tcgaactaca gcaagc 26

<210> SEQ ID NO 23
<211> LENGTH: 696
<212> TYPE: PRT
<213> ORGANISM: Artificial Sequence
<220> FEATURE:
<223> OTHER INFORMATION: Possible mutations in Endo-Rp amino acid
sequence, which are confirmed to work in working examples.
<220> FEATURE:
<221> NAME/KEY: mutation
<222> LOCATION: (128)..(128)
<223> OTHER INFORMATION: The position can be various amino acid,
preferably Ala or Thr
<220> FEATURE:
<221> NAME/KEY: mutation
<222> LOCATION: (172)..(172)
<223> OTHER INFORMATION: The position can be various amino acid,
preferably Asn, Asp, Gln, Glu, Ala, Cys, His, Phe, Gly, Leu, Ile,
Lys, Met, Pro, Ser, Thr or Val.
<220> FEATURE:
<221> NAME/KEY: mutation
<222> LOCATION: (176)..(176)
<223> OTHER INFORMATION: The position can be various amino acid,
preferably Asp or Arg.
<220> FEATURE:
<221> NAME/KEY: mutation
<222> LOCATION: (214)..(214)
<223> OTHER INFORMATION: The position can be various amino acid with
large side chain, preferably Tyr or Phe.
<220> FEATURE:
<221> NAME/KEY: mutation
<222> LOCATION: (216)..(216)
<223> OTHER INFORMATION: The position can be various amino acid with
small side chain, preferably Ser, Ala or Val.
<220> FEATURE:
<221> NAME/KEY: mutation
<222> LOCATION: (245)..(245)
<223> OTHER INFORMATION: The position can be various amino acid,
preferably Leu or Ser.
<220> FEATURE:
<221> NAME/KEY: mutation
<222> LOCATION: (246)..(246)
<223> OTHER INFORMATION: The position can be various amino acid,
preferably Asn or Asp.
<220> FEATURE:
<221> NAME/KEY: mutation
<222> LOCATION: (275)..(275)
<223> OTHER INFORMATION: The position can be various amino acid,
preferably Thr or Ile.
<220> FEATURE:
<221> NAME/KEY: mutation
<222> LOCATION: (278)..(278)
<223> OTHER INFORMATION: The position can be various amino acid with
hydrophobic side chain, preferably, Phe, Tyr, Ala, Leu or Ile.
<220> FEATURE:
<221> NAME/KEY: mutation
<222> LOCATION: (283)..(283)
<223> OTHER INFORMATION: The position can be various amino acid,
preferably Phe or Ser.
<220> FEATURE:
<221> NAME/KEY: mutation
<222> LOCATION: (306)..(306)
<223> OTHER INFORMATION: The position can be various amino acid,
preferably Leu or Ile.
<220> FEATURE:

<221> NAME/KEY: mutation
<222> LOCATION: (307)..(307)
<223> OTHER INFORMATION: The position can be various amino acid, preferably Phe, Tyr or His.
<220> FEATURE:
<221> NAME/KEY: mutation
<222> LOCATION: (310)..(310)
<223> OTHER INFORMATION: The position can be various amino acid with poler or charged side chain, preferably Asp, Glu,
<220> FEATURE:
<221> NAME/KEY: mutation
<222> LOCATION: (314)..(314)
<223> OTHER INFORMATION: The position can be various amino acid, preferably Glu or Gln.
<220> FEATURE:
<221> NAME/KEY: mutation
<222> LOCATION: (333)..(333)
<223> OTHER INFORMATION: The position can be various amino acid, preferably Asp or Gly.
<220> FEATURE:
<221> NAME/KEY: mutation
<222> LOCATION: (434)..(434)
<223> OTHER INFORMATION: The position can be various amino acid, preferably Ile or Leu.
<220> FEATURE:
<221> NAME/KEY: mutation
<222> LOCATION: (460)..(460)
<223> OTHER INFORMATION: The position can be various amino acid, preferably Val or Ala.
<220> FEATURE:
<221> NAME/KEY: mutation
<222> LOCATION: (527)..(527)
<223> OTHER INFORMATION: The position can be various amino acid, preferably Ile or Val.
<220> FEATURE:
<221> NAME/KEY: mutation
<222> LOCATION: (569)..(569)
<223> OTHER INFORMATION: The position an be various amino acid, preferably Lys or Thr
<220> FEATURE:
<221> NAME/KEY: mutation
<222> LOCATION: (610)..(610)
<223> OTHER INFORMATION: The position can be various amino acid, preferably Phe or Ser.
<220> FEATURE:
<221> NAME/KEY: mutation
<222> LOCATION: (626)..(626)
<223> OTHER INFORMATION: The position can be various amino acid, preferably His or Arg.

<400> SEQUENCE: 23

```
Met Pro Ser Leu Glu Leu Gln Gln Ala Ala Asp Thr Arg Leu Phe Glu
1               5                   10                  15

Ser Met Pro Leu Gln Thr Met Asn Glu Leu Gly Ser Trp Glu Pro Ser
            20                  25                  30

Asn Ala Ser Arg Ala Asn Ile Ala Thr Ile Pro Leu His Gln Arg Ser
        35                  40                  45

Asn Leu Asp Pro Ala Glu Pro Arg Leu Ile Val Thr His Asp Met Ala
    50                  55                  60

Gly Gly Tyr Lys Glu Asp Ser Asn Ile Gln Gly Asn Thr Tyr Asp Thr
65                  70                  75                  80

Ile Tyr Ser Cys Gln Tyr Trp Gln Tyr Val Asp Thr Phe Ile Tyr Phe
                85                  90                  95

Ser His His Arg Val Thr Ile Pro Pro Val Asn Trp Ile Asn Ala Cys
            100                 105                 110

His Arg Asn Gly Val Lys Thr Leu Gly Thr Phe Ile Val Glu Gly Xaa
        115                 120                 125

Ala Gly Met Phe Ala Leu Glu Arg Phe Val Tyr Gly Pro Glu Pro Gly
    130                 135                 140
```

```
Gln Arg Asn Ser Trp Ser Pro Tyr Tyr Ala Asp Lys Leu Val Asp Ile
145                 150                 155                 160

Ala Glu Phe Tyr Gly Phe Asp Gly Trp Leu Leu Xaa Ile Glu Ser Xaa
                165                 170                 175

Phe Phe Pro Leu Tyr Arg Asn Pro Ser Leu Lys Ala Ile His Leu Ala
            180                 185                 190

Lys Leu Leu Arg Tyr Leu Lys Asn Ala Met His Ala Arg Val Pro Gly
        195                 200                 205

Ser Glu Ile Ile Trp Xaa Asp Xaa Met Thr Thr Asn Gly Ser Val Gln
    210                 215                 220

Trp Gln Asn Asn Ile Thr Pro Lys Asn Ser Ile Phe Phe Glu Ala Ala
225                 230                 235                 240

Asp Gly Ile Phe Xaa Xaa Tyr Trp Trp Asn Ala Thr Val Pro Pro Leu
                245                 250                 255

Ala Leu Gln Val Ala His Arg Leu Gly Arg Gln Gly Ser Asp Val Tyr
            260                 265                 270

Phe Gly Xaa Asp Val Xaa Gly Arg Gly Thr Xaa Gly Gly Gly Gly Phe
        275                 280                 285

Asp Ser Tyr Leu Ala Val Gly Thr Ala Arg Ala Phe Lys Thr Ser Ser
    290                 295                 300

Ala Xaa Xaa Gly Thr Xaa Trp Ile Tyr Xaa His Phe Gly Lys Lys Asp
305                 310                 315                 320

Phe Glu Leu Met Asp Arg Leu Leu Trp Leu Gly Gly Xaa Gln Ser Glu
                325                 330                 335

Tyr Pro Ala Gln Glu Gly Glu Gln Asn Arg Thr Val Lys Val Thr Ser
            340                 345                 350

His Leu Gly Arg His Pro Gly Ile Ala Asp Val Ser Pro Val Arg Ser
        355                 360                 365

Ala Pro Gly Lys Thr Trp Phe Ala Thr Trp Phe Asp Arg Gly Tyr Gly
    370                 375                 380

Thr Gly Phe Tyr Tyr Gln Gly Lys Lys Leu Leu Ser Gln Pro Trp Ser
385                 390                 395                 400

His Leu Ser His Gln Ser Ile Pro Pro Asn Leu Ile Ala Arg Leu Gln
                405                 410                 415

Arg Glu Glu Asn His Gly Leu Ser Tyr Phe Leu Ala Asp Asp Asp Ala
            420                 425                 430

Tyr Xaa Gly Gly Thr Ser Leu Leu Ile Ala Ala Glu Ile Thr Gln Glu
        435                 440                 445

Arg Gln Leu Pro Leu Tyr Gln Leu Glu Tyr Asp Xaa Thr Glu Gly Cys
    450                 455                 460

Glu Val Gln Phe Ile Tyr Lys Ser Pro Glu Pro Asp Met Gln Gly Lys
465                 470                 475                 480

Ile Asp Ile Tyr Leu Asn Leu Gln Val Thr Asp Ile Leu Pro Asp Glu
                485                 490                 495

Leu Ala Phe Tyr Trp Gln Asp Val Thr Asp Ala Ser Ser Gln Ala Asp
            500                 505                 510

Ala Thr Thr Ala Met Arg Leu Tyr Leu Asn Glu Asn Thr Val Xaa Tyr
        515                 520                 525

Leu Lys Pro Ser Arg Lys Gln Glu Leu Ala Glu Gly Trp Leu Leu Cys
    530                 535                 540

Ser Val Arg Val Pro Pro Thr Tyr Pro Leu Gly Ile Ala Thr Ile Lys
545                 550                 555                 560

Glu Leu Gly Ile His Val Asp Gly Xaa Glu Thr Val Leu Phe Arg Leu
```

-continued

```
                565                 570                 575

Gly Leu Leu Thr Ile Ile Pro Leu Gly Asp Ala Pro Ser Ala Leu Ser
            580                 585                 590

Arg Ile Thr Gln Val Gln Leu Gln Arg Asp Glu Asp Ile His Ser Lys
        595                 600                 605

Cys Xaa Ser Ser Ser Cys Glu Leu Trp Ala Thr Leu Ser Trp Met Met
    610                 615                 620

Glu Xaa Asn Ser Lys Glu Asp Trp Asp Gln Val Asp His Tyr Met Ile
625                 630                 635                 640

Phe Phe Lys Asn Val Asp Ser Lys Ala Glu Pro Ile Phe Leu Gly Thr
                645                 650                 655

Ser Phe Ser Thr Glu Tyr Arg Ile Ser Gly Leu Glu Ile Lys Lys His
            660                 665                 670

Gly Asn Ser Ile Glu Ile Trp Ala Val Asn Arg Leu Gly Thr Val Ile
        675                 680                 685

Ala Arg Gln Asp Ile Asp Ile Gln
    690                 695
```